(12) United States Patent
Guo et al.

(10) Patent No.: US 9,403,794 B2
(45) Date of Patent: *Aug. 2, 2016

(54) IMAGING BETA-AMYLOID PEPTIDES AND INHIBITION OF BETA-AMYLOID PEPTIDE AGGREGATION

(71) Applicant: Hong Kong Baptist University, Hong Kong (HK)

(72) Inventors: Lei Guo, Hong Kong (HK); Di Xu, Hong Kong (HK); See-Lok Ho, Hong Kong (HK); Chung-Yan Poon, Hong Kong (HK); Olivia T. W. Ng, Hong Kong (HK); Hung Wing Li, Hong Kong (HK); Ken K. L. Yung, Hong Kong (HK); Daniel W. J. Kwong, Hong Kong (HK); Ricky M. S. Wong, Hong Kong (HK)

(73) Assignee: HONG KONG BAPTIST UNIVERSITY, Kowloon Tong, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/231,724

(22) Filed: Mar. 31, 2014

(65) Prior Publication Data

US 2014/0213614 A1    Jul. 31, 2014

Related U.S. Application Data

(63) Continuation-in-part of application No. 13/447,127, filed on Apr. 13, 2012.

(51) Int. Cl.
*A61K 49/10* (2006.01)
*A61K 49/00* (2006.01)
*C07D 401/06* (2006.01)
*A61K 49/08* (2006.01)
*A61K 31/4709* (2006.01)
*A61K 45/06* (2006.01)

(52) U.S. Cl.
CPC .......... *C07D 401/06* (2013.01); *A61K 31/4709* (2013.01); *A61K 45/06* (2013.01); *A61K 49/0002* (2013.01); *A61K 49/0021* (2013.01); *A61K 49/0026* (2013.01); *A61K 49/085* (2013.01); *A61K 49/10* (2013.01)

(58) Field of Classification Search
CPC ....... A61K 49/00; A61K 49/10; A61K 49/08; A61K 31/4735
See application file for complete search history.

(56) References Cited

U.S. PATENT DOCUMENTS 7,700,616 B2 * 4/2010 Tamagnan et al. ............ 514/299

OTHER PUBLICATIONS

Xin Jiang Feng et. al., Cyanines as New Fluorescent Probes for DNA Detection and Two-Photon Excited Bioimaging, Organic Letters, 2010, vol. 112(10), 2194-2197.*

* cited by examiner

*Primary Examiner* — Michael G Hartley
*Assistant Examiner* — Jagadishwar Samala
(74) *Attorney, Agent, or Firm* — Ella Cheong Hong Kong; Sam T. Yip

(57) ABSTRACT

The present invention is in the field of pharmaceuticals and chemical industries. In particular, the present invention relates to methods for labeling, imaging and detecting the beta-amyloid (Aβ) peptides, oligomers, and fibrils in vitro by using carbazole-based fluorophores. A further aspect of the present invention relates to a method of reducing and preventing aggregation of beta-amyloid peptides for Alzheimer's disease (AD) as well as of treating and/or preventing Alzheimer's disease by using carbazole-based fluorophores.

7 Claims, 44 Drawing Sheets

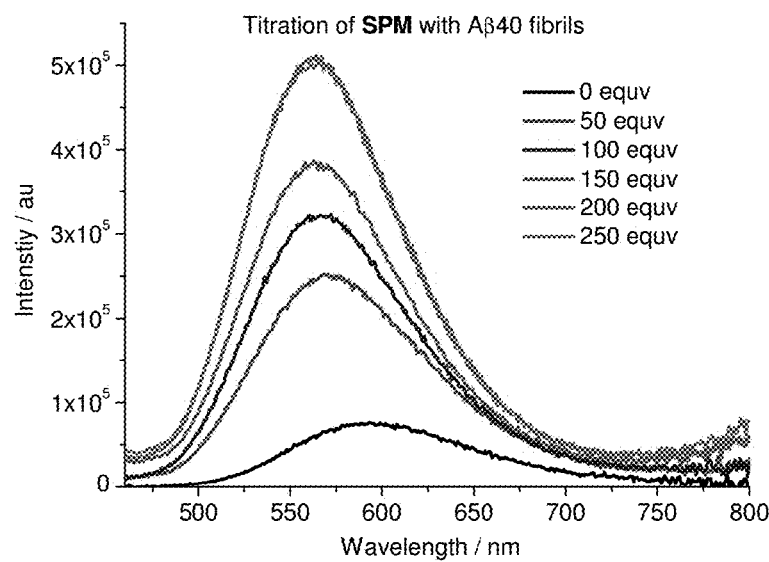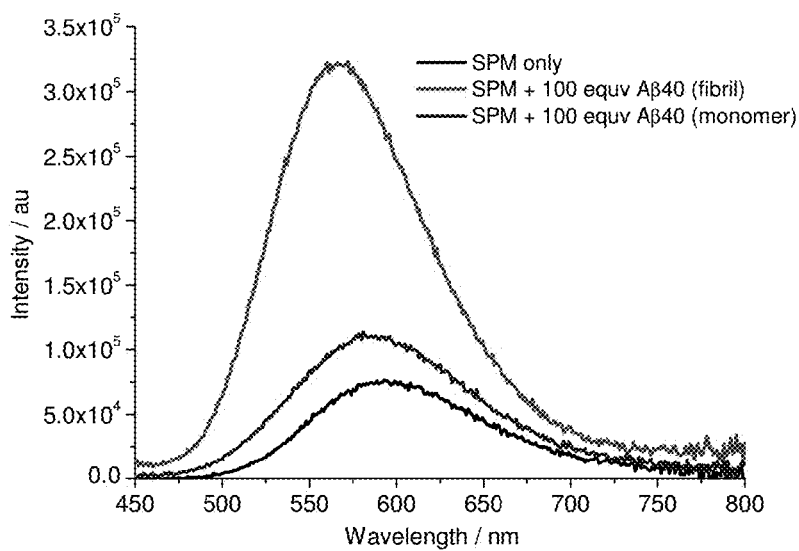
Figure 1

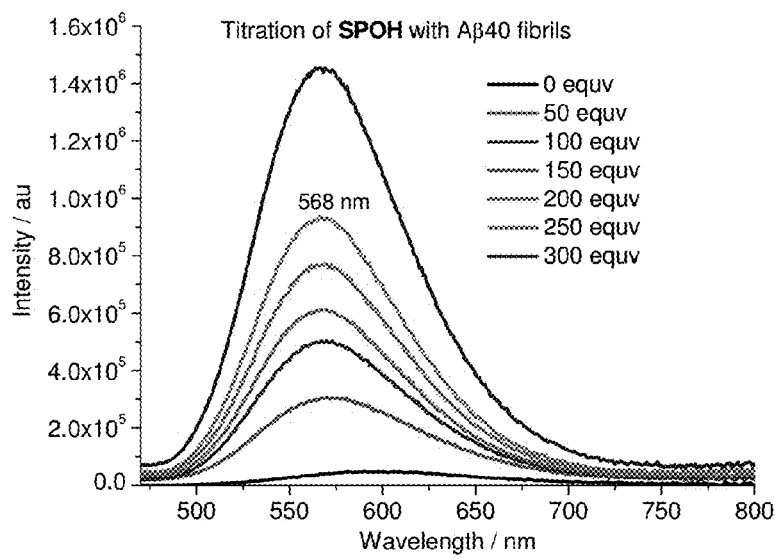
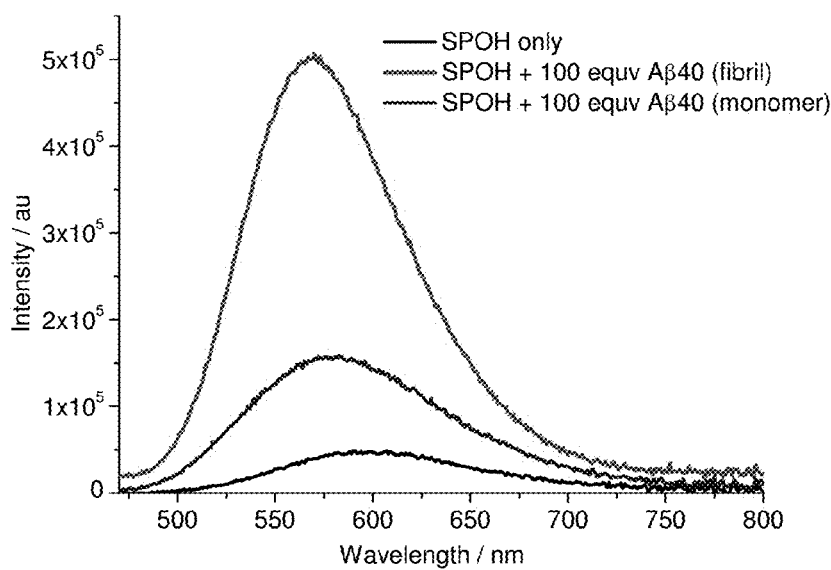
Figure 1

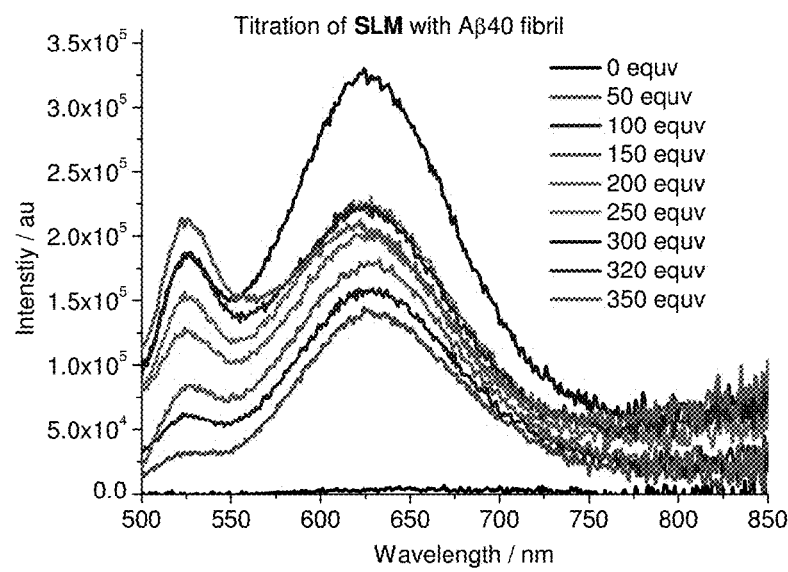
Figure 1E
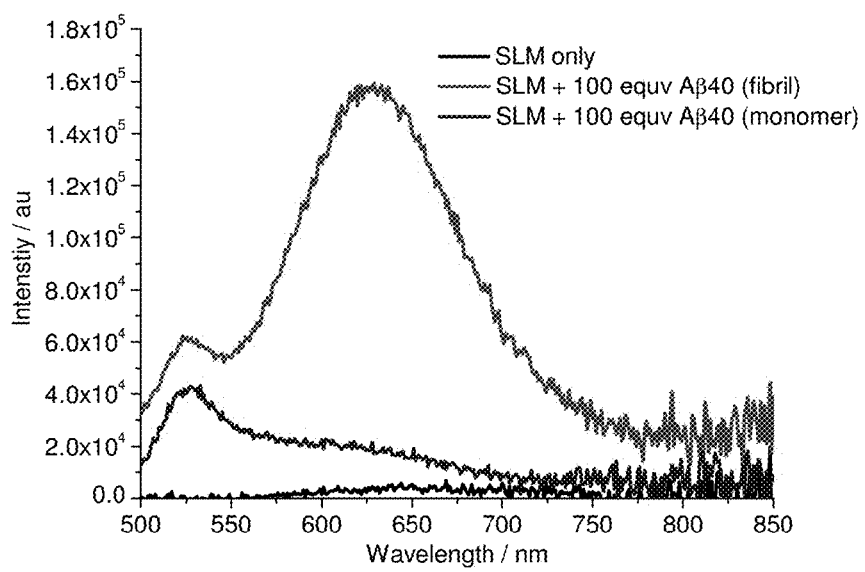
Figure 1F
Figure 1

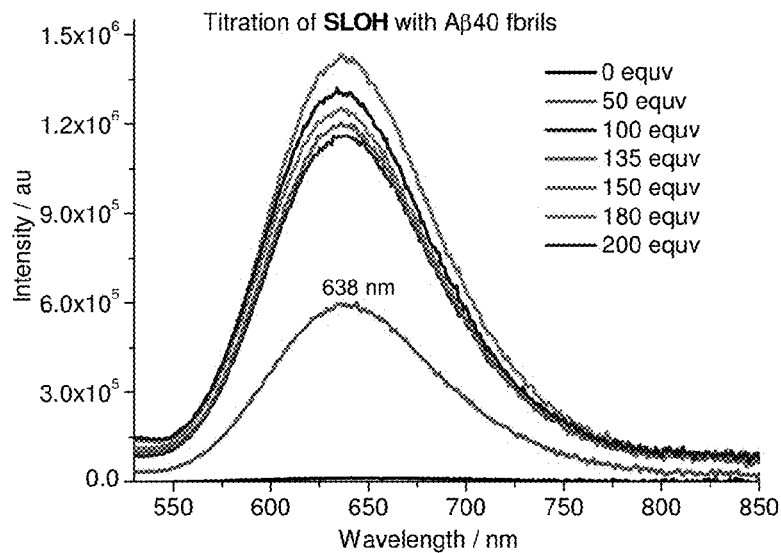
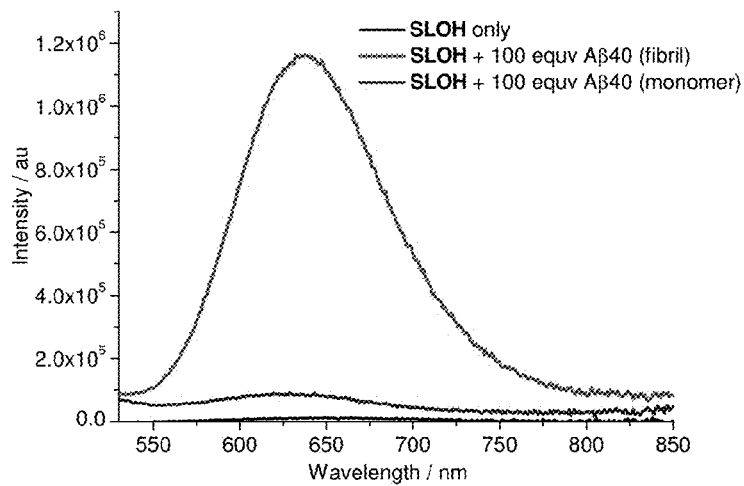
Figure 1

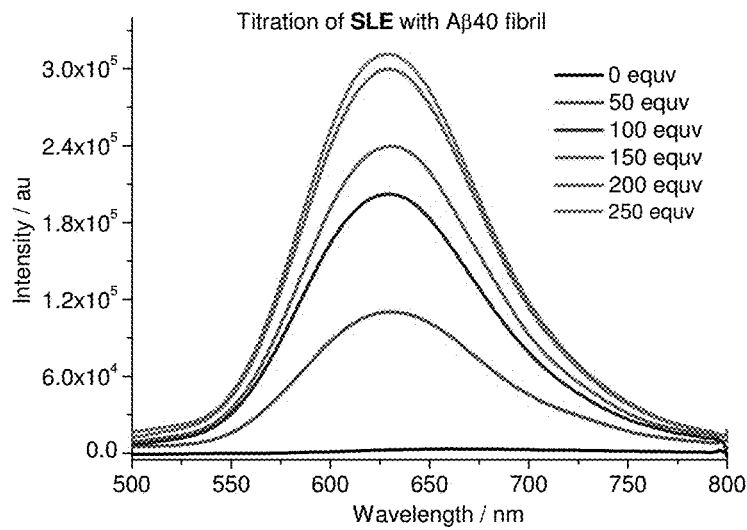
Figure 1I
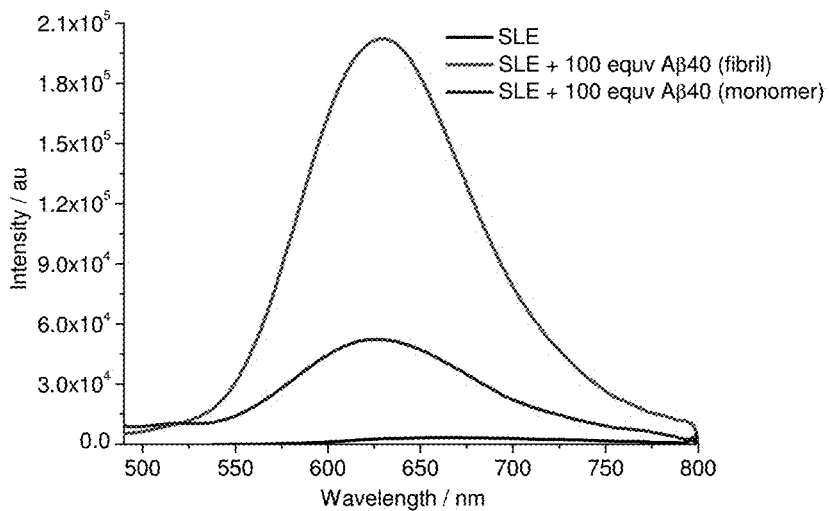
Figure 1J
Figure 1

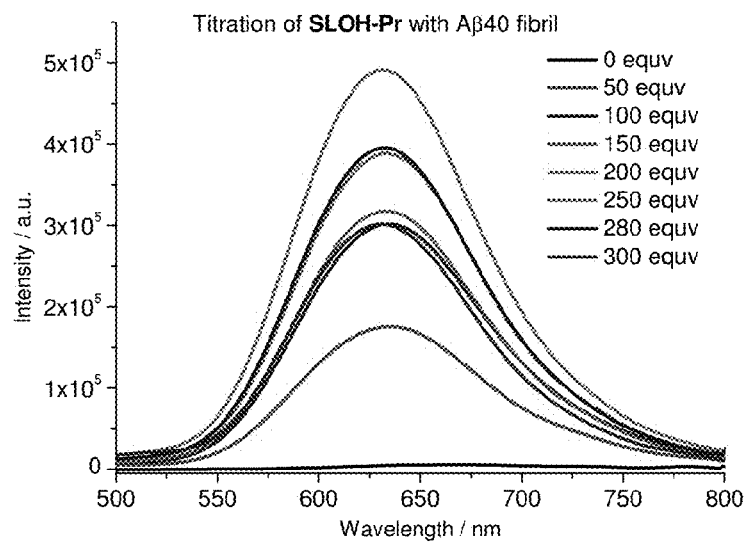
Figure 1K
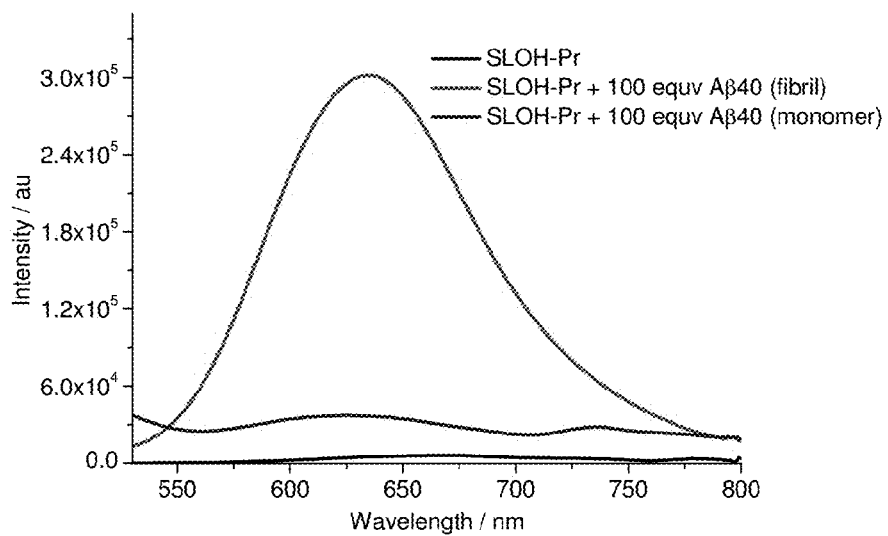
Figure 1L
Figure 1

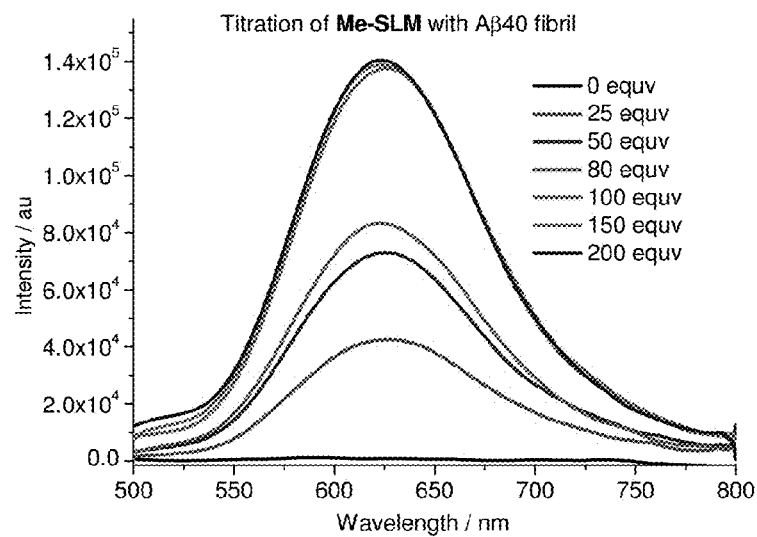
Figure 1M
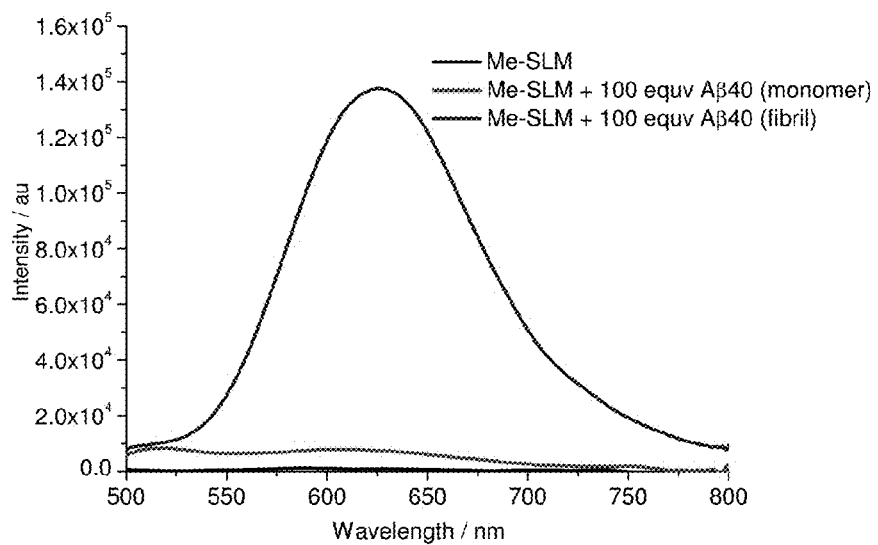
Figure 1N
Figure 1

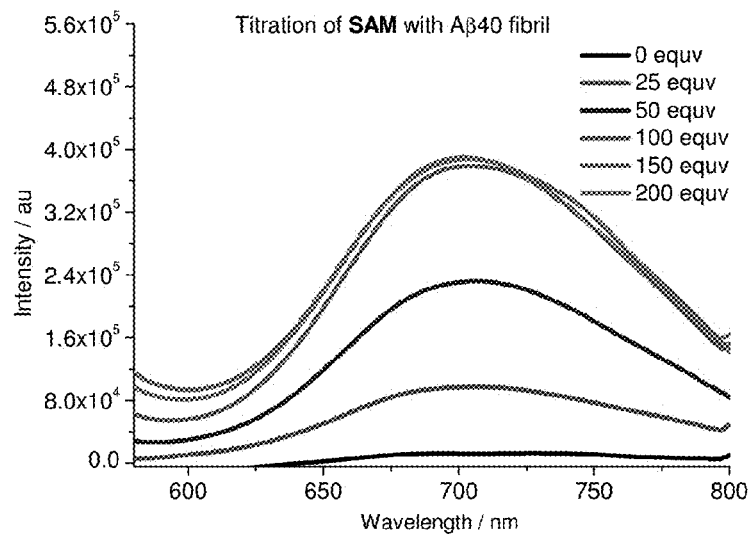
Figure 1O
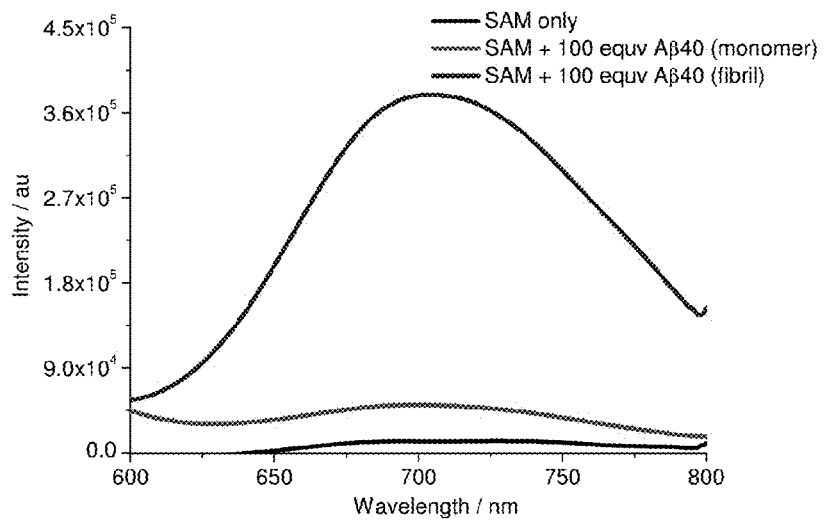
Figure 1P
Figure 1

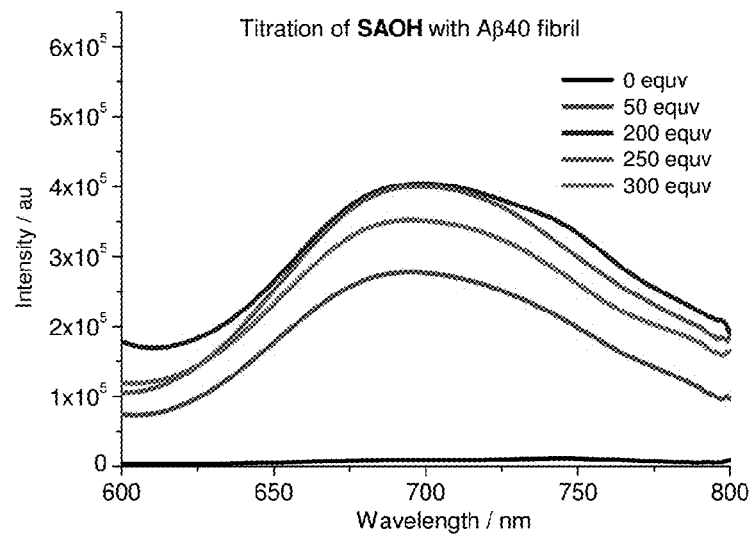
Figure 1Q
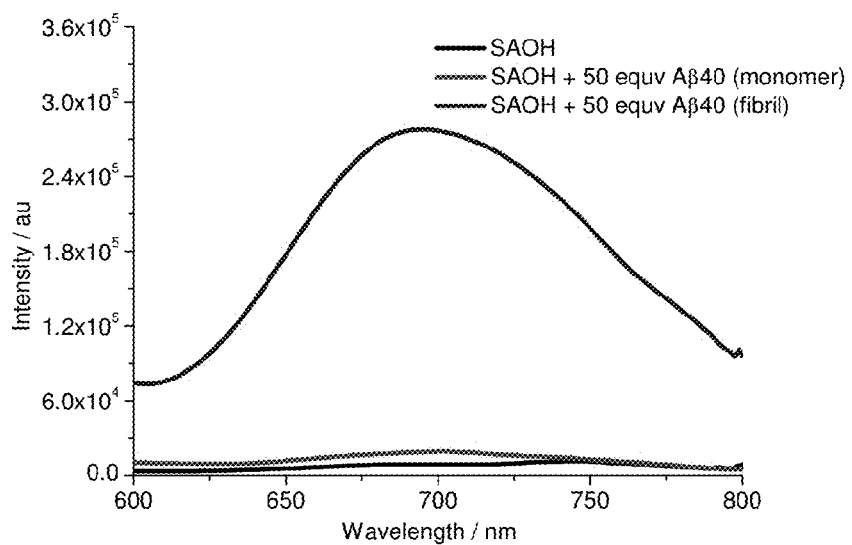
Figure 1R
Figure 1

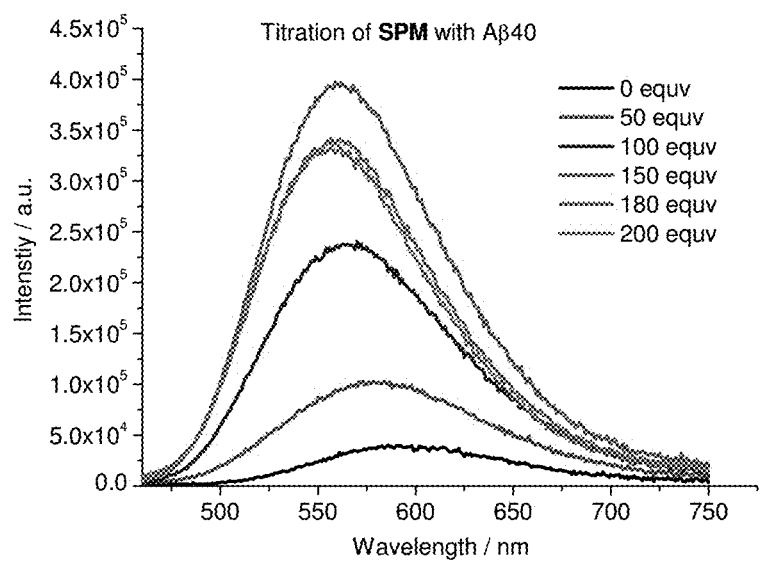
Figure 2A
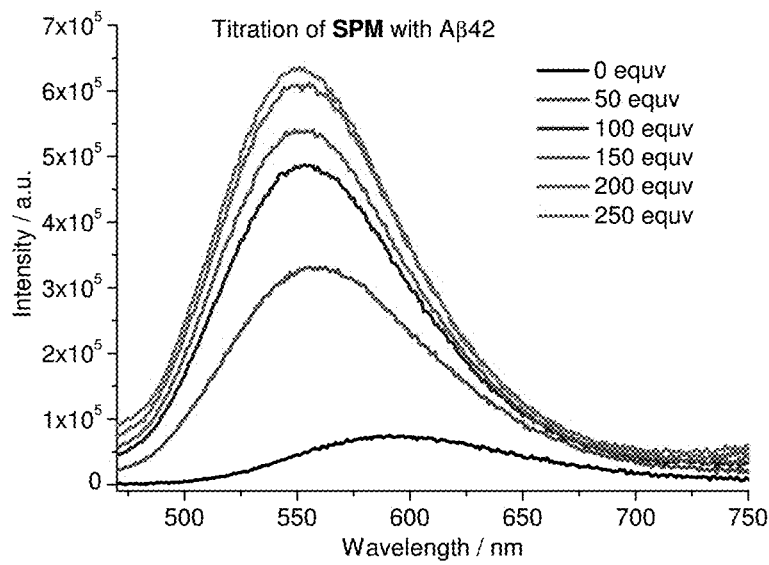
Figure 2B
Figure 2

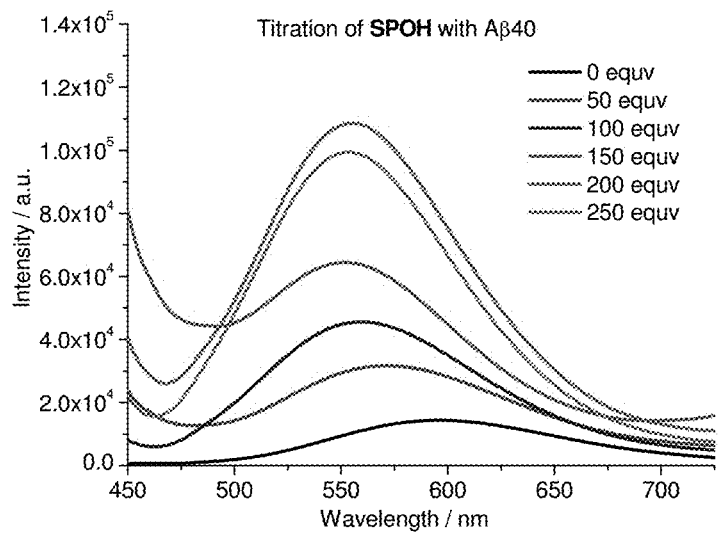
Figure 2C
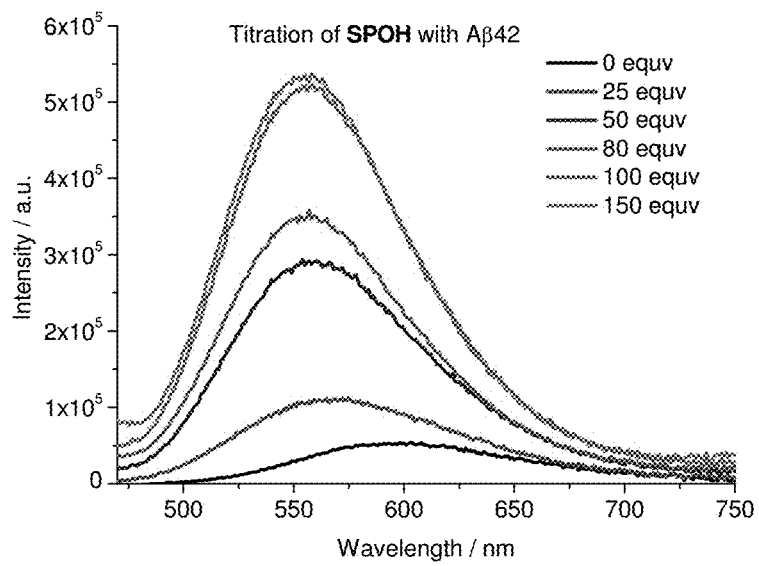
Figure 2D
Figure 2

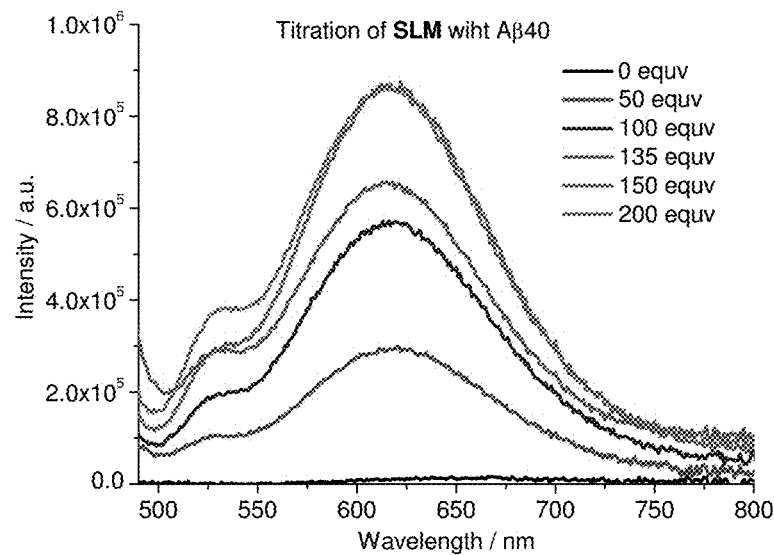
Figure 2E
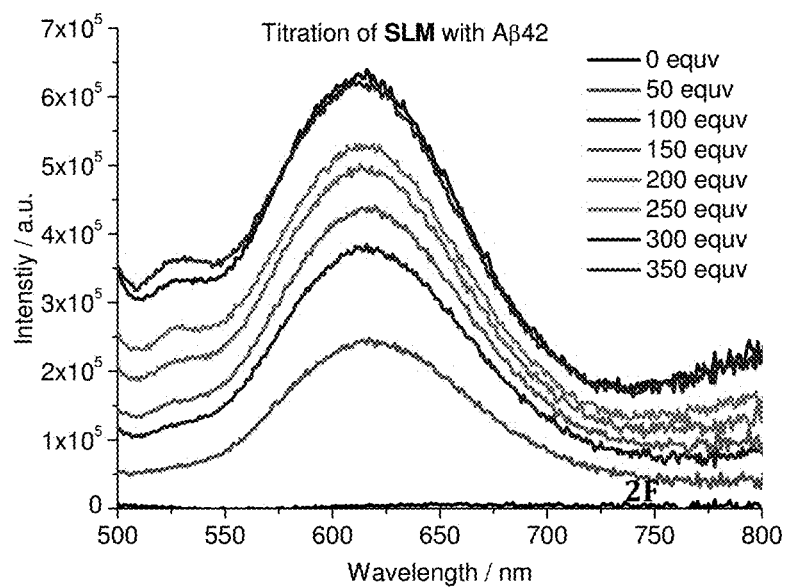
Figure 2F
Figure 2

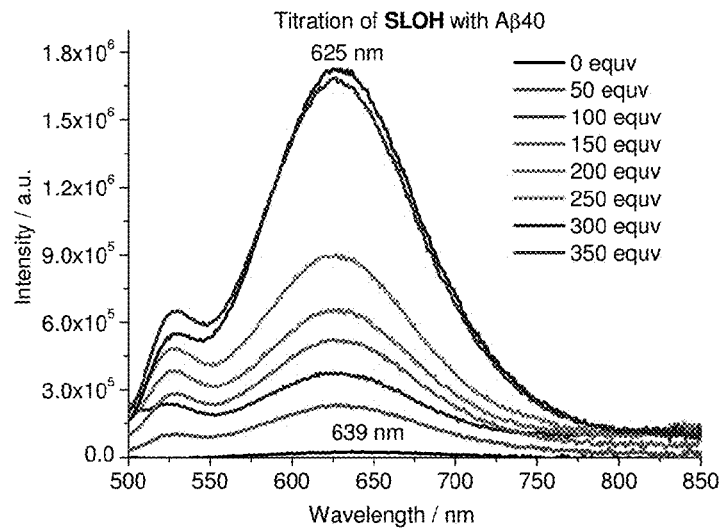
Figure 2G
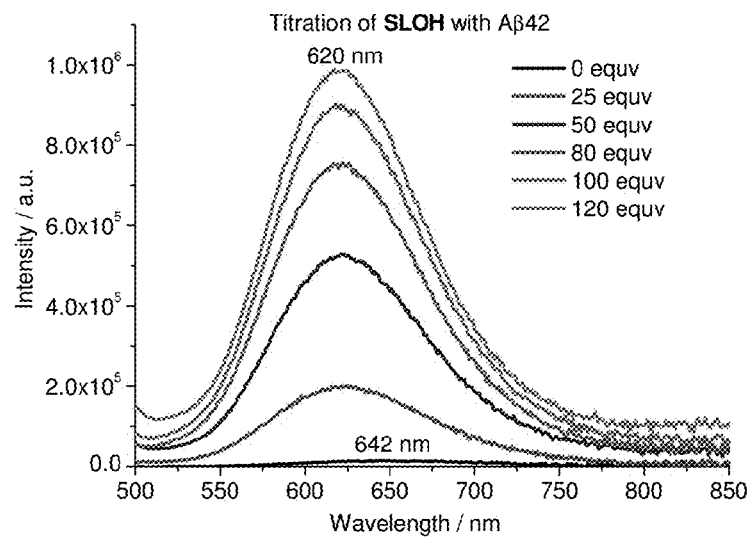
Figure 2H
Figure 2

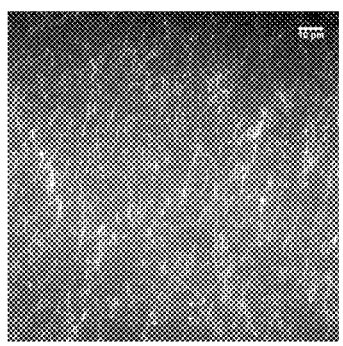 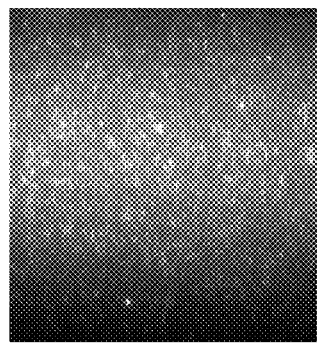 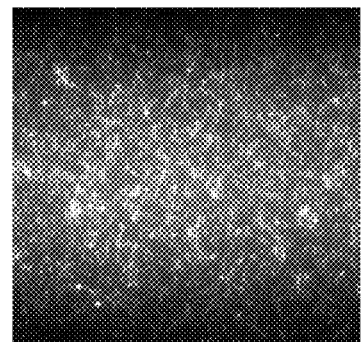
Figure 3A        Figure 3B        Figure 3C
Figure 3

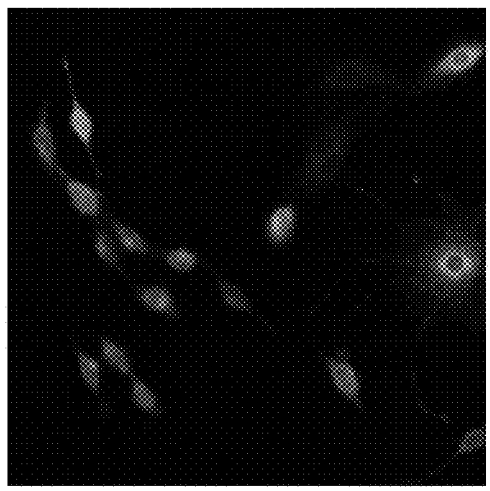 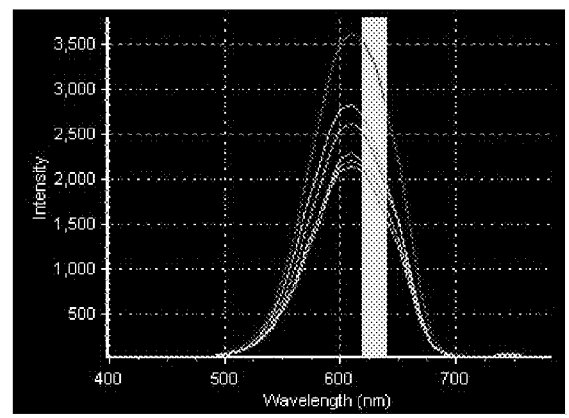
Figure 4A   Figure 4B
Figure 4

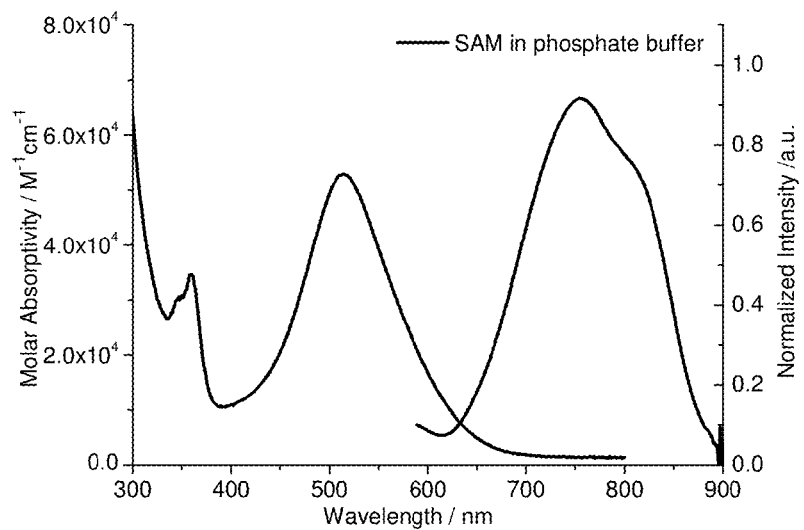
Figure 5A
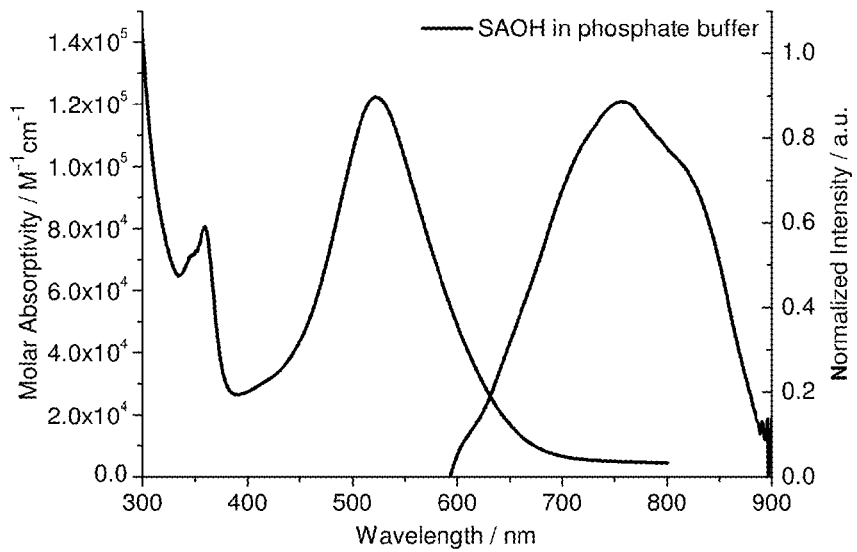
Figure 5B
Figure 5

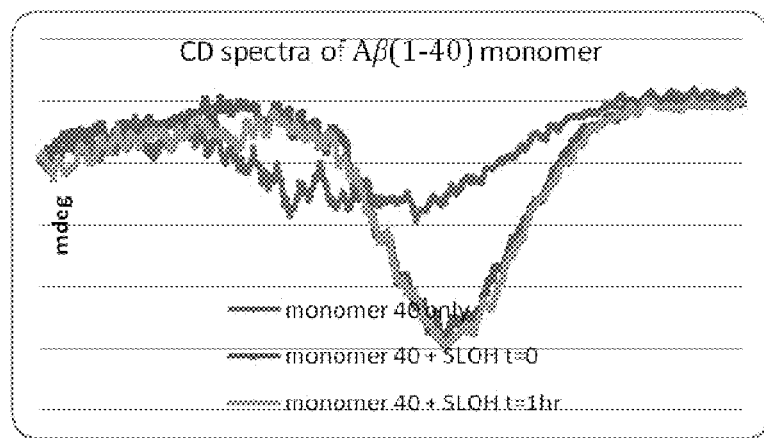
Figure 6A
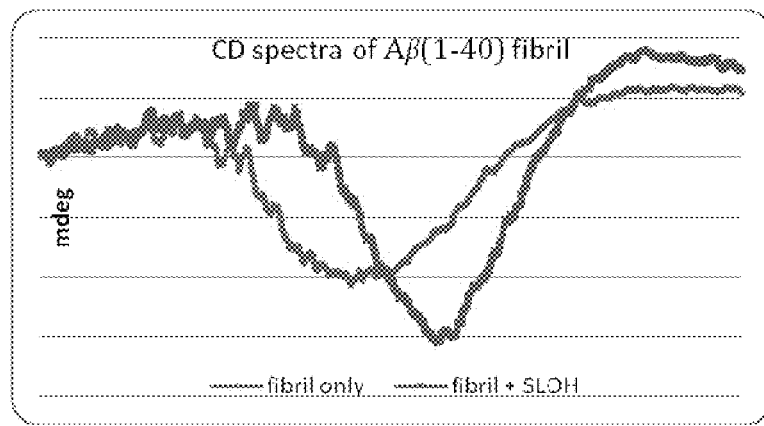
Figure 6B
Figure 6

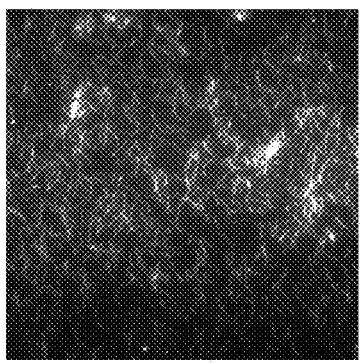
Figure 7A
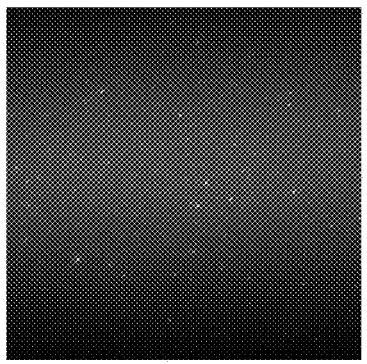
Figure 7B
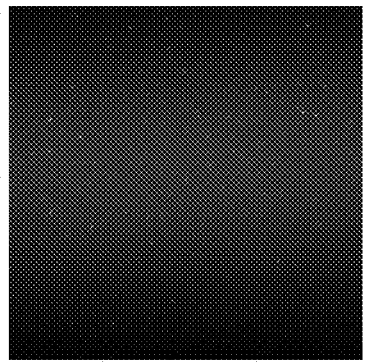
Figure 7C
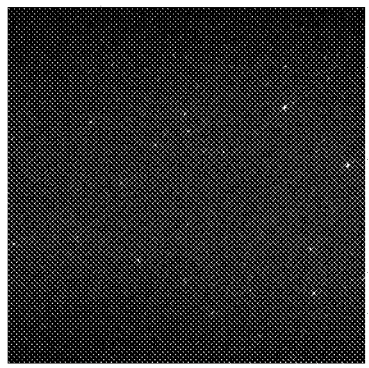
Figure 7D
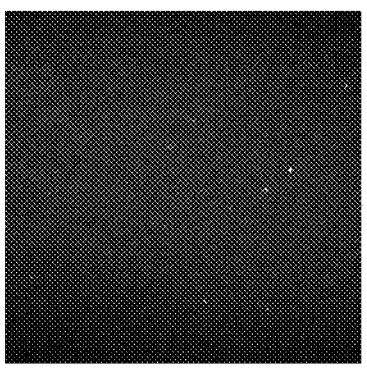
Figure 7E
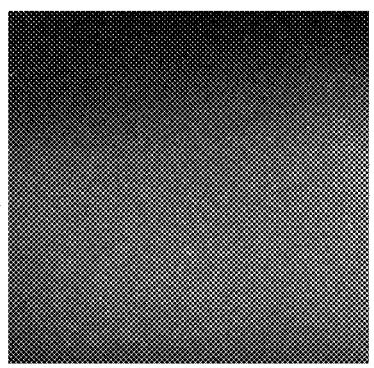
Figure 7F
Figure 7

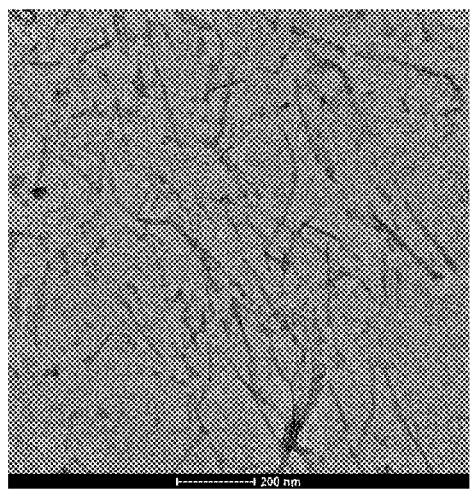 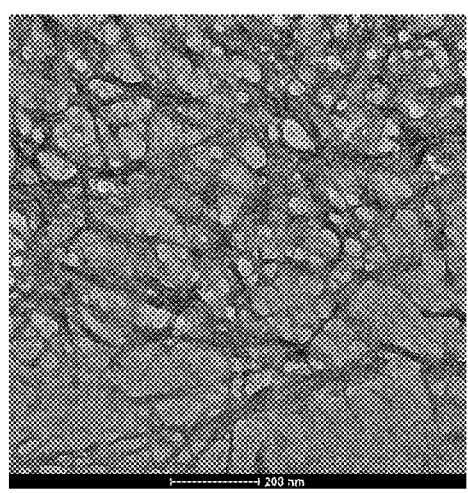
Figure 8A  Figure 8B
Figure 8

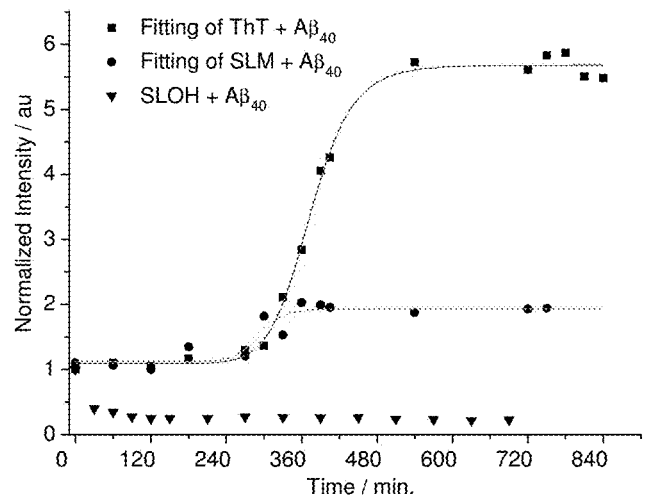
Figure 9A
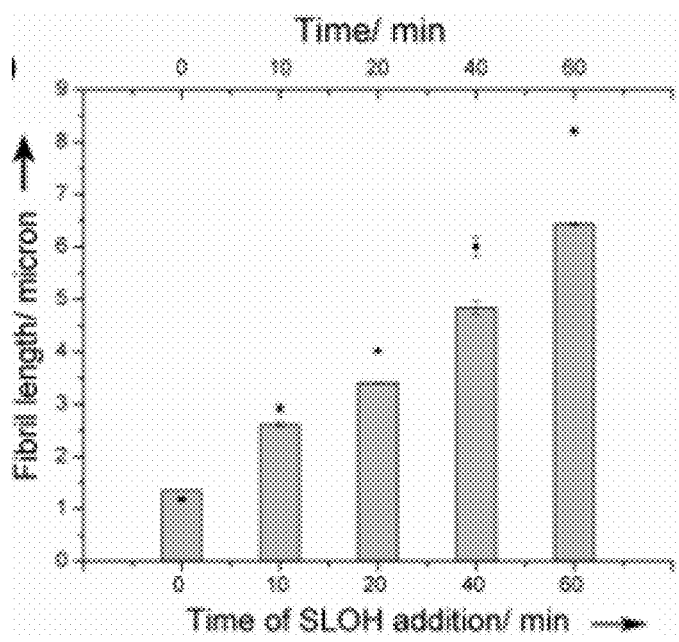
Figure 9B
Figure 9

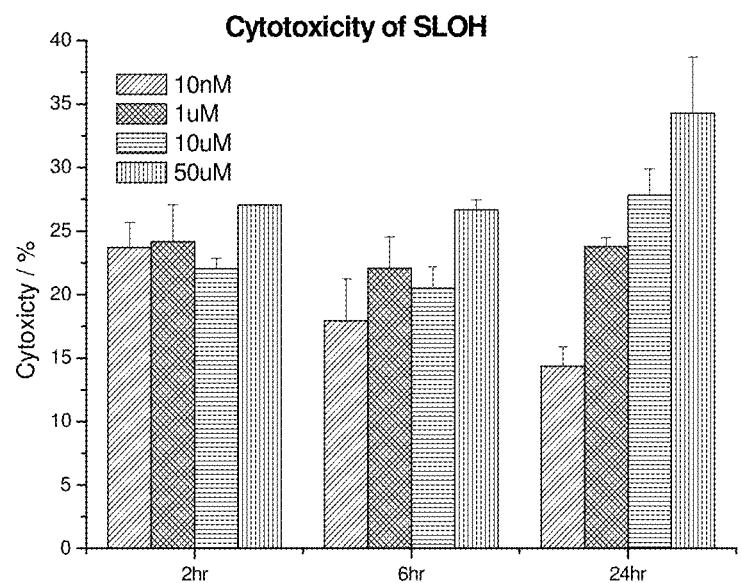
Figure 10A
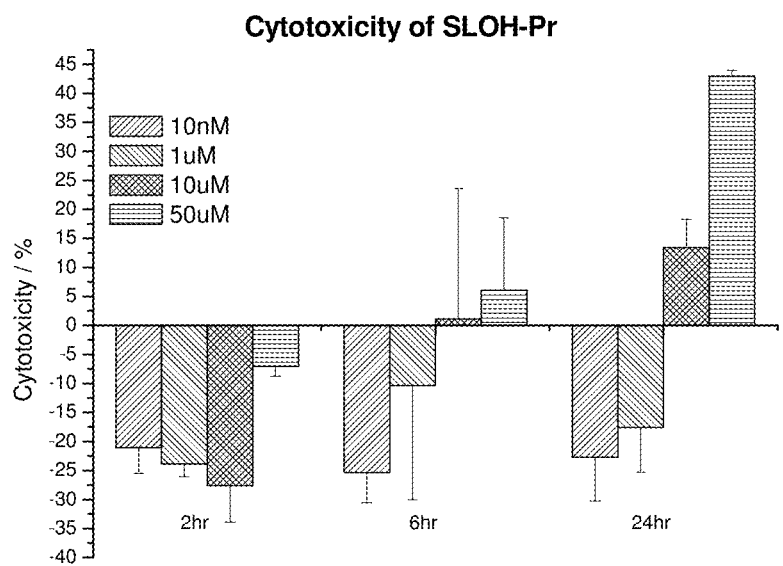
Figure 10B
Figure 10

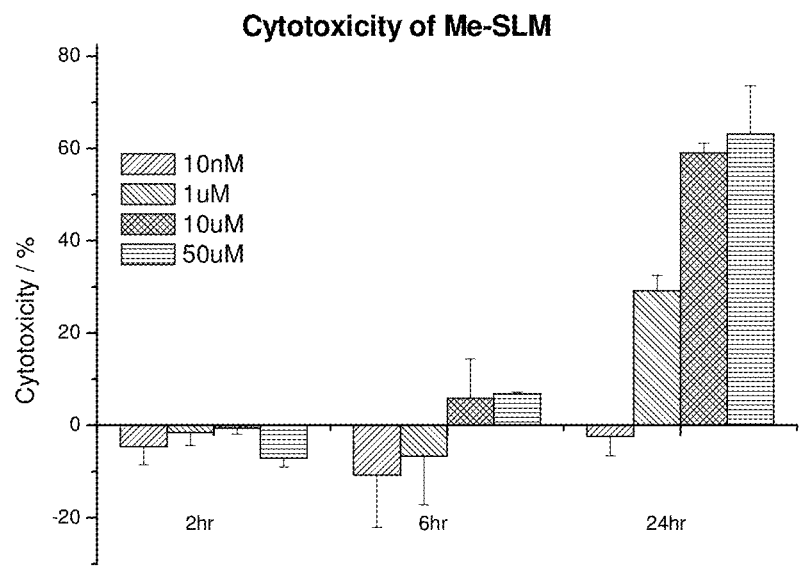
Figure 10C
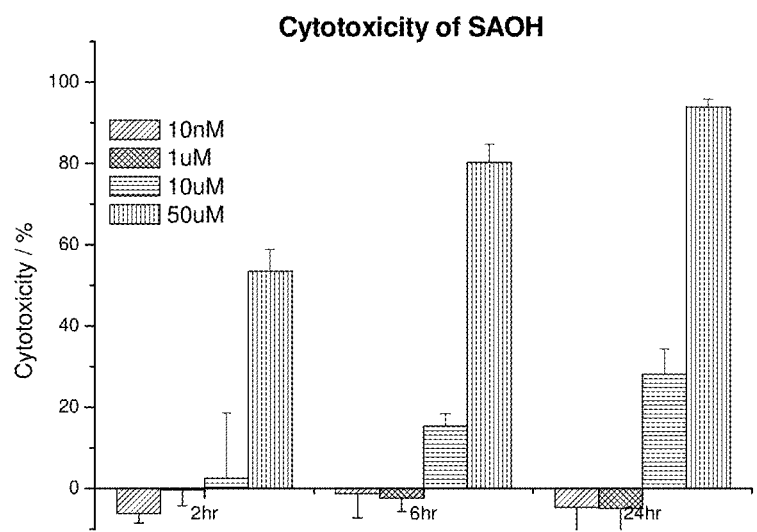
Figure 10D
Figure 10

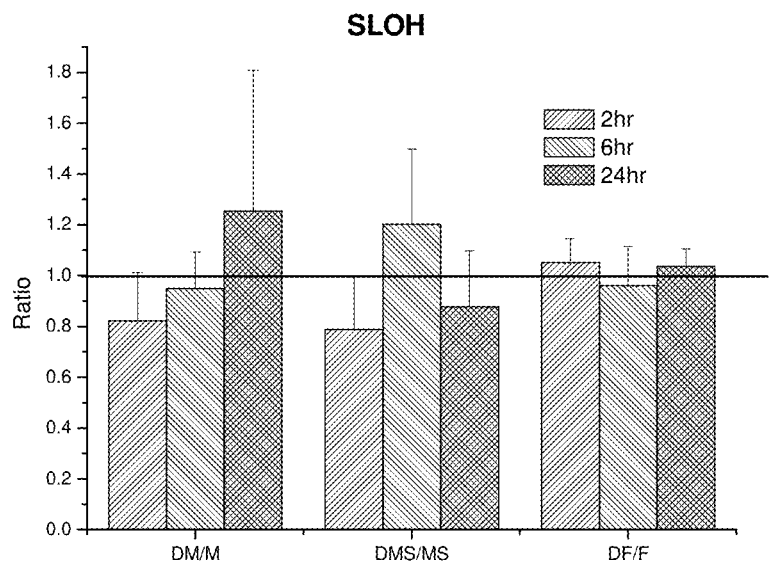
Figure 11A
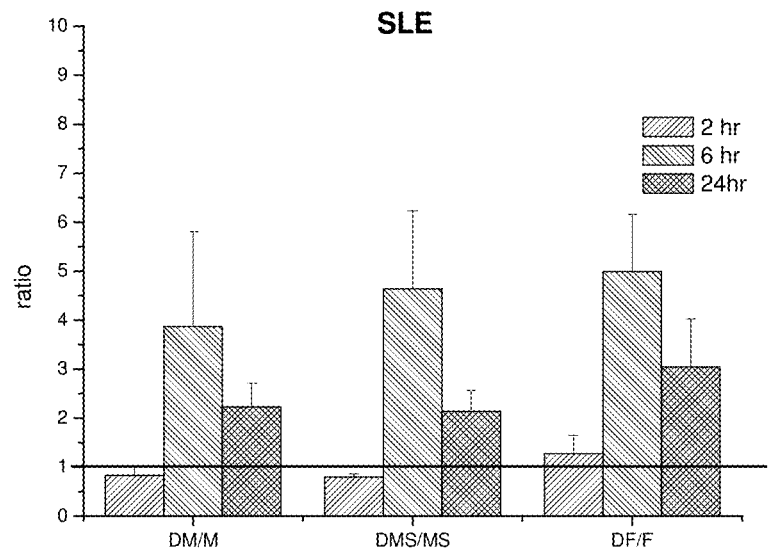
Figure 11B
Figure 11

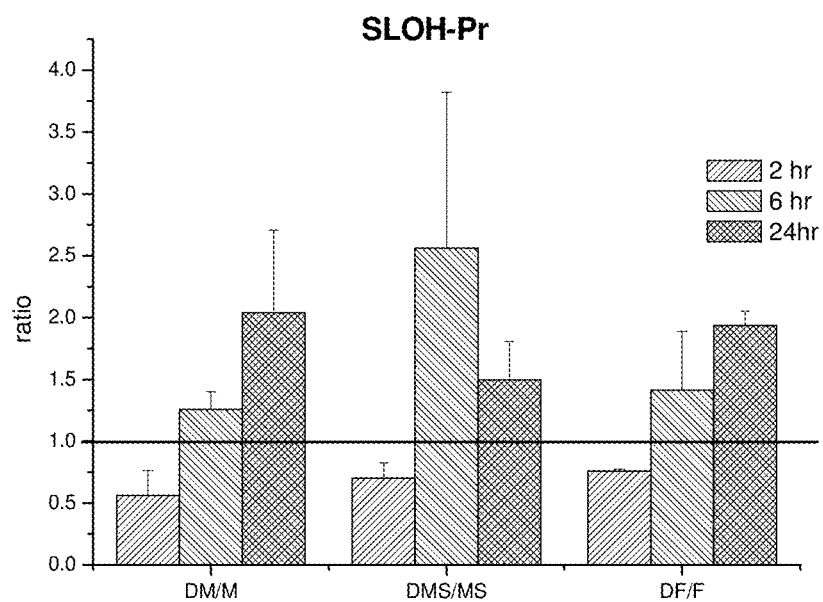
Figure 11C
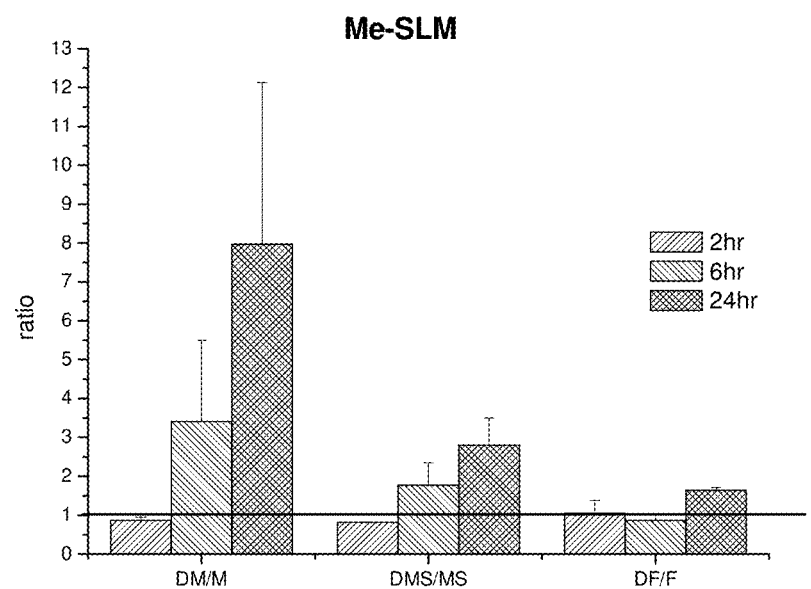
Figure 11D
Figure 11

Figure 12A
Figure 12B
Figure 12C
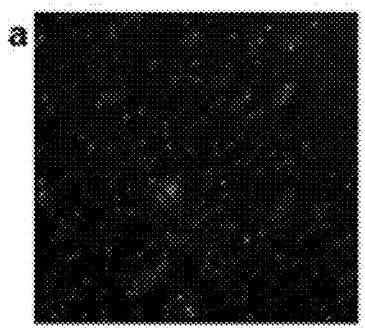
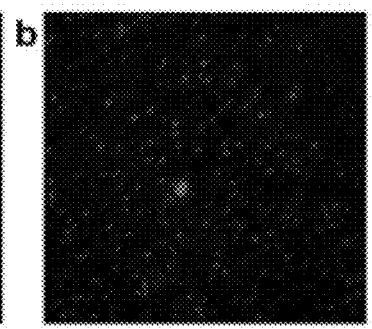
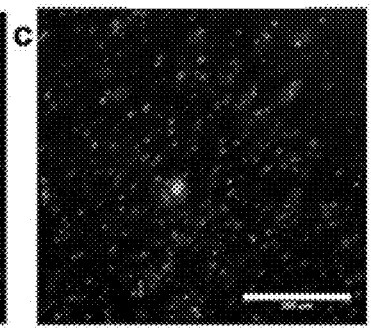
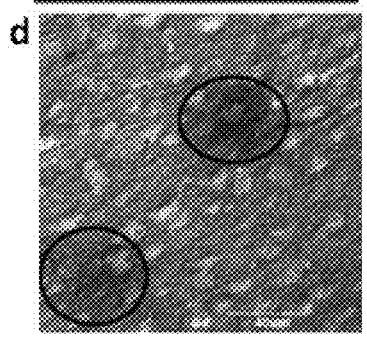
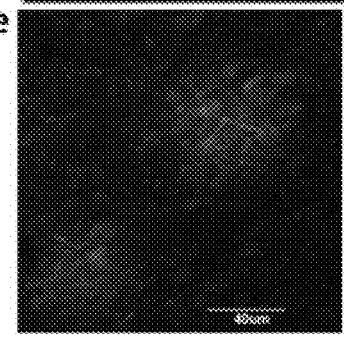
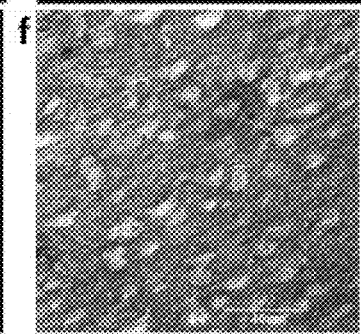
Figure 12D
Figure 12E
Figure 12F
Figure 12

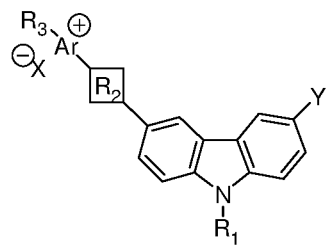

S series

Ar = heteroaromatic ring
such as

 or 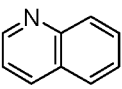 or 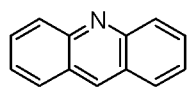 or 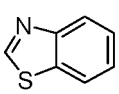 or 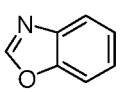

$R_1$ = polyethylene glycol chain
such as $(CH_2CH_2O)_2CH_3$ or
alkyl chain such as methyl, hexyl or
peptide chain or
glycosidic group or
$\underset{\underset{O}{\|}}{C}NHCH((CH_2CH_2O)_2CH_3)_2$ $\boxed{R_2}$ = HC=CH or
C≡C or
N=N or
HC=N X = anion such as
$F^-$ or
$Cl^-$ or
$Br^-$ or
$I^-$ or
$HSO_4^-$ or
$HPO_4^-$ or
$HCO_3^-$ or
$OTs^-$ or
$OMs^-$ $R_3$ = HO-alkyl or
alkyl-COOalkyl or
alkyl-$CONH_2$ or
alkyl-CONHalkyl or
polyethylene glycol chain
such as $(CH_2CH_2O)_2CH_3$ Y = H or
F or
Cl or
OH or
$OCH_3$

Figure 14

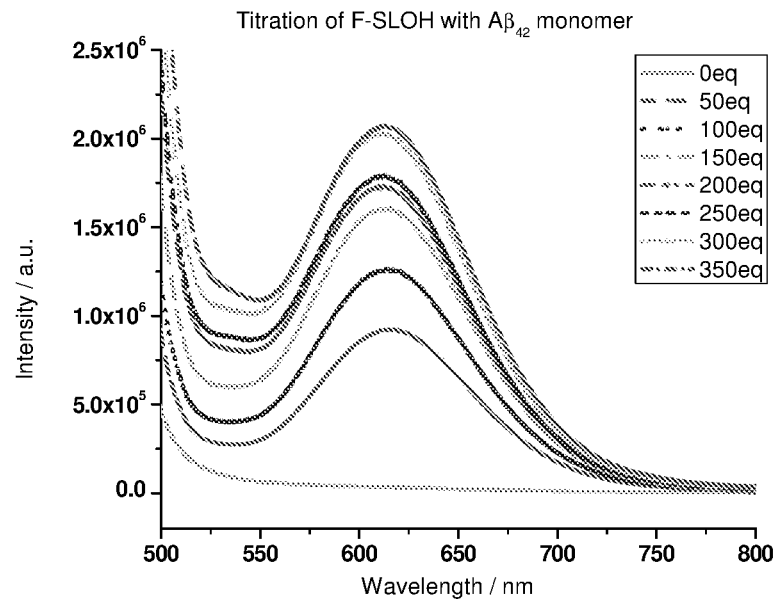
Figure 16A
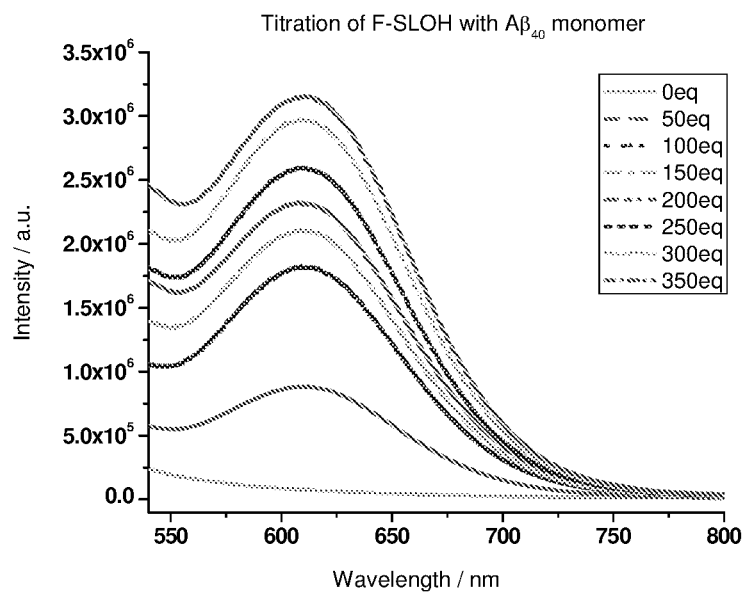
Figure 16B
Figure 16

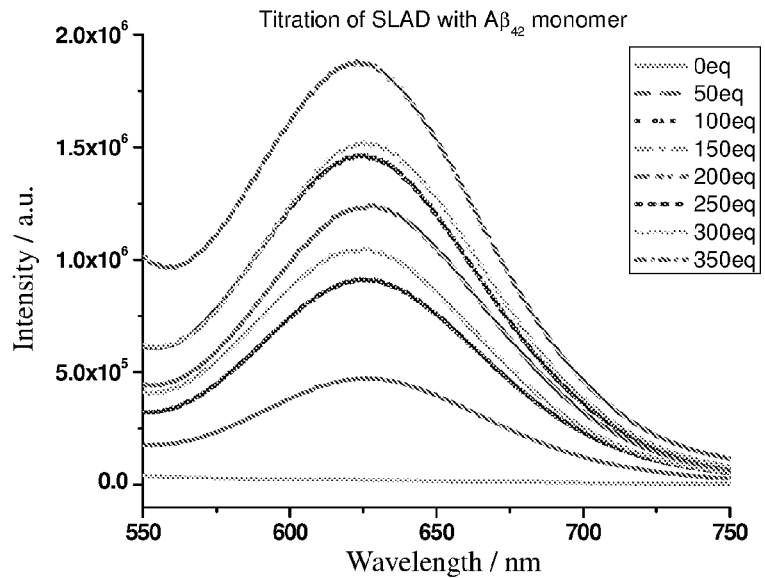
Figure 16D
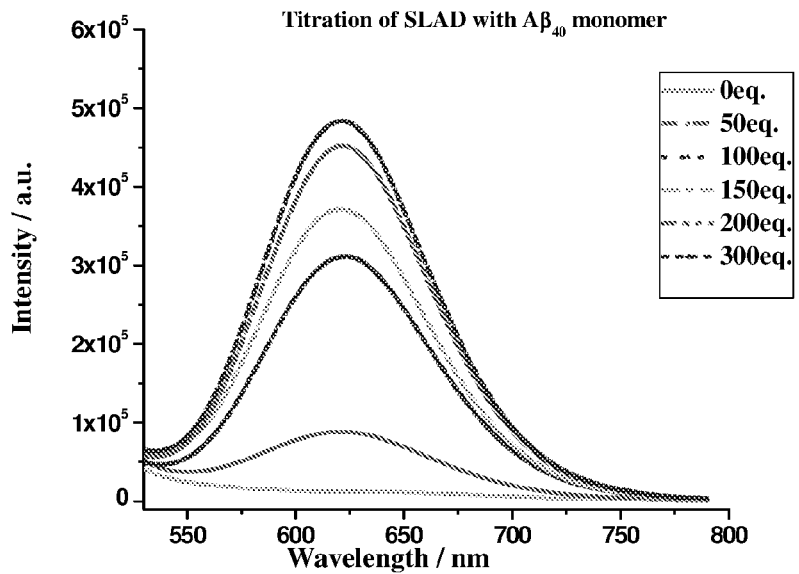
Figure 16E
Figure 16

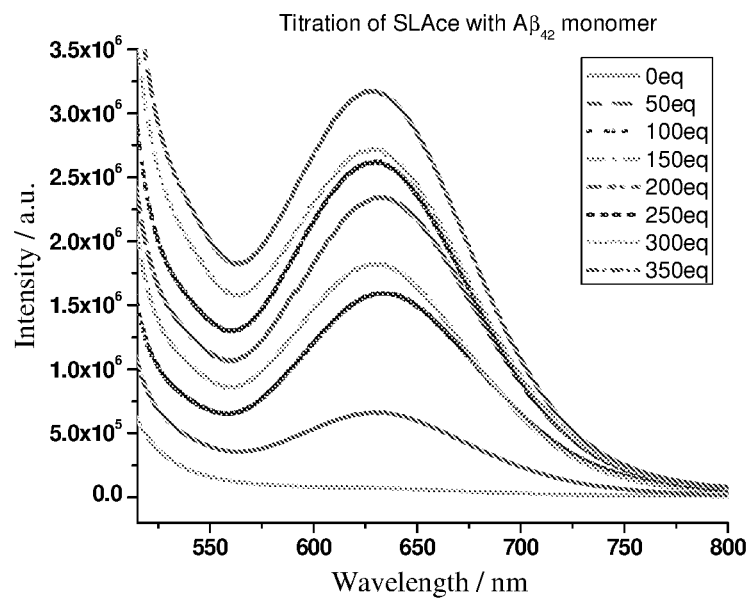
Figure 16G
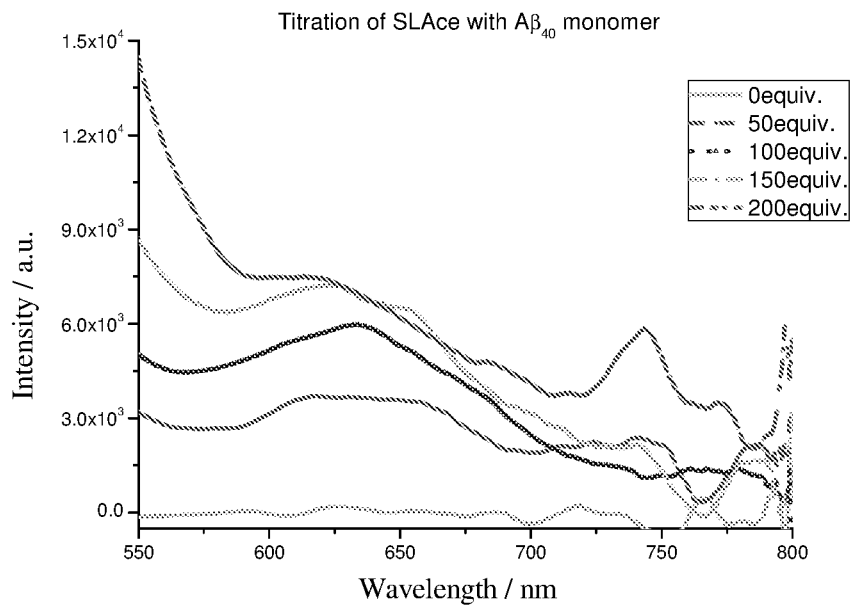
Figure 16H
Figure 16

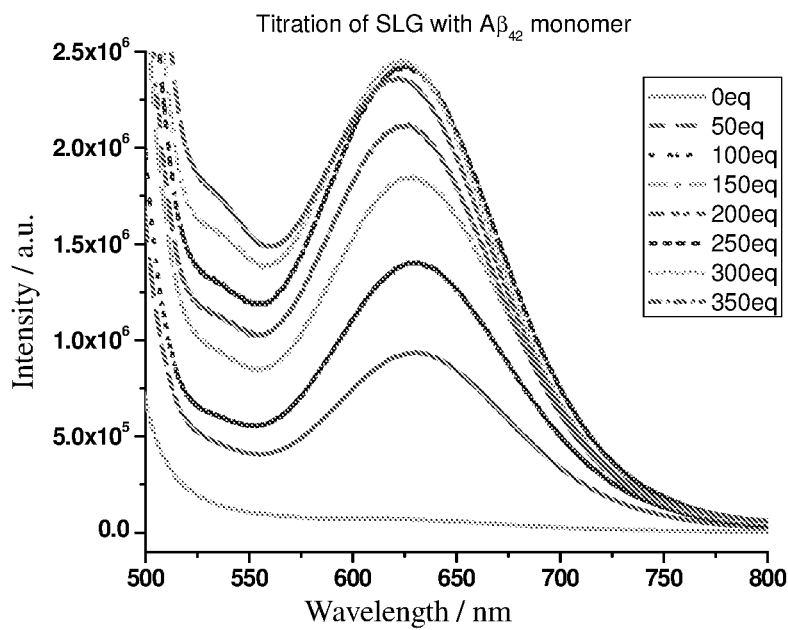
Figure 16J
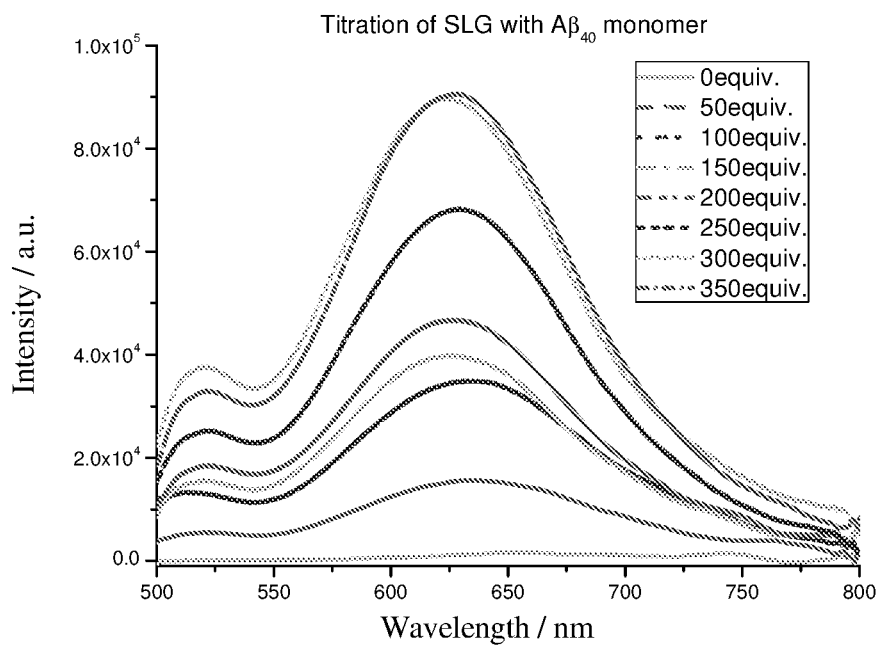
Figure 16K
Figure 16

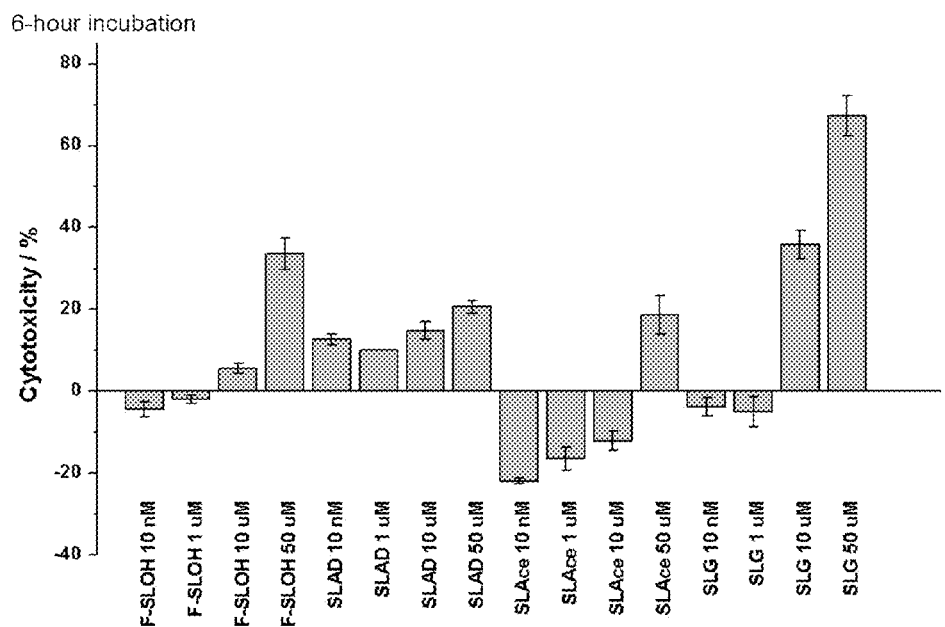
Figure 18B
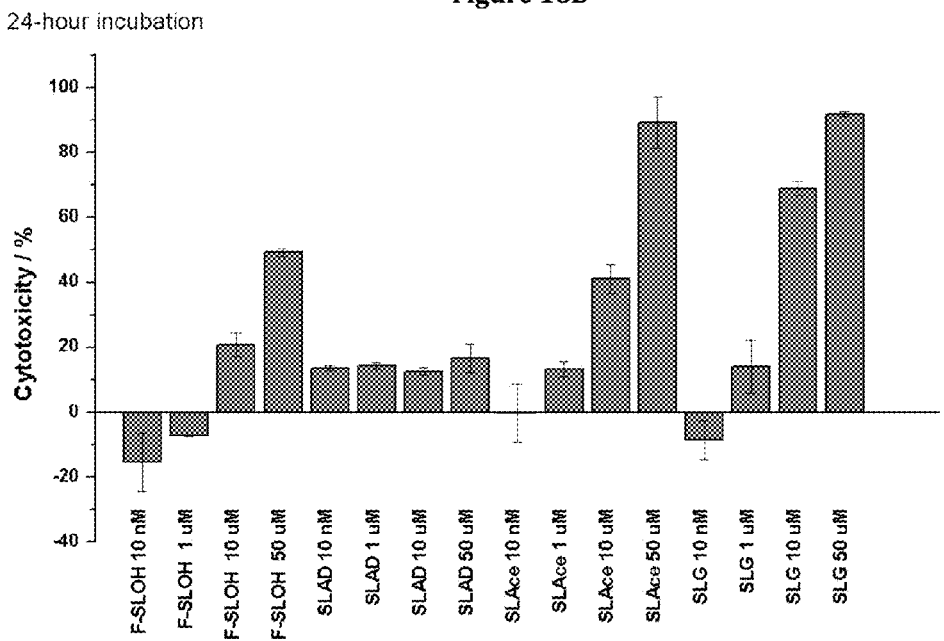
Figure 18C
Figure 18

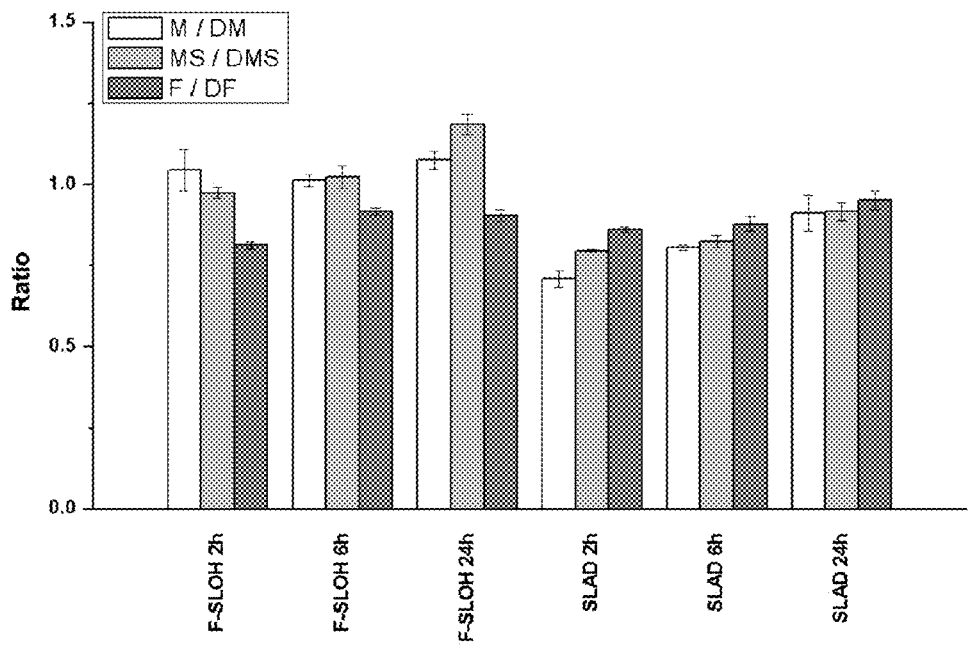
Figure 19A
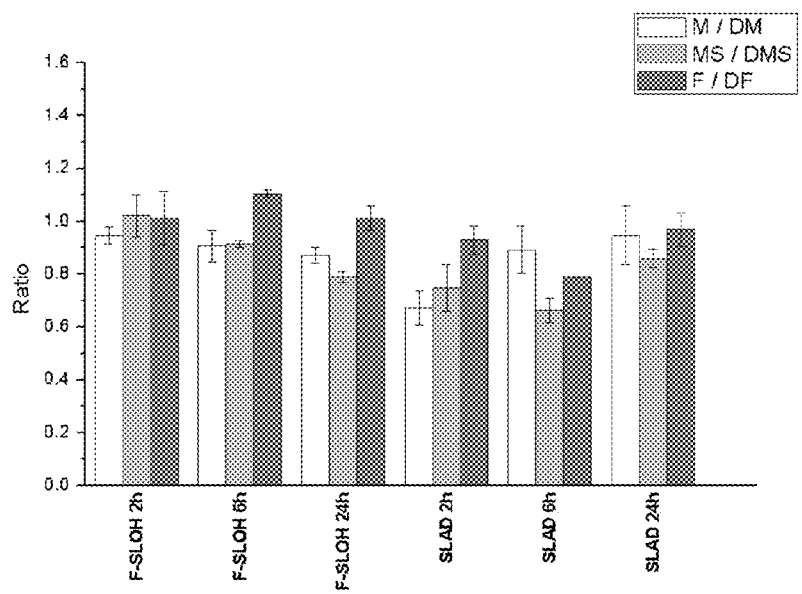
Figure 19B
Figure 19

Figure 20A  Figure 20B  Figure 20C
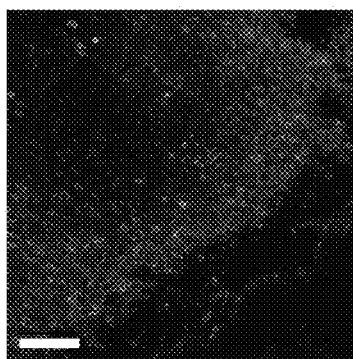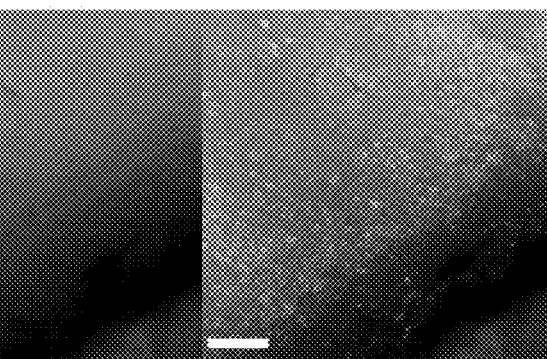
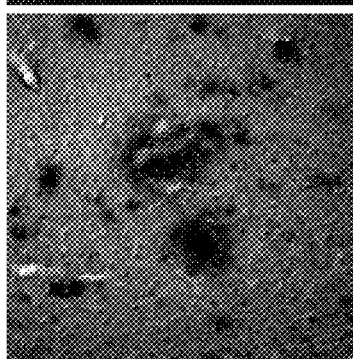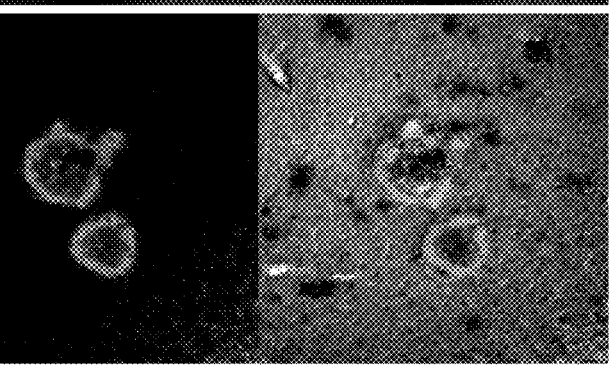
Figure 20D  Figure 20E  Figure 20F
Figure 20

IMAGING BETA-AMYLOID PEPTIDES AND INHIBITION OF BETA-AMYLOID PEPTIDE AGGREGATION

CROSS-REFERENCE TO RELATED APPLICATIONS

The present application is a continuation-in-part application of the US non-provisional patent application Ser. No. 13/447,127 filed Apr. 13, 2012, which claims priority of U.S. provisional application No. 61/477,614 filed Apr. 21, 2011, and which the disclosure is hereby incorporated by reference in its entirety.

FIELD OF INVENTION

The present invention relates to methods of detecting and monitoring aggregation of beta-amyloid peptides which are associated with neurodegenerative diseases as well as treating and/or preventing the neurodegenerative diseases by using carbazole-based fluorophores. In particular, the present invention provides methods for labeling and imaging the beta-amyloid (Aβ) peptides, oligomers, and fibrils in vitro and/or in vivo, as well as treating and/or preventing Alzheimer's disease by using the carbazole-based fluorophores of the present invention.

BACKGROUND OF INVENTION

Loss of memory and cognitive functions are often associated with aging. This is the result of neurodegeneration. However, in some cases, this process of neurodegeneration becomes accelerated due to premature cell death in the brain, leading to a variety of cognitive impairments or dementia. Among these neurodegenerative disorders, Alzheimer's disease (AD) is most prevalent in recent years. It has also attracted considerable attention locally because Prof. Charles K. Kao, former president of the Chinese University of Hong Kong and Nobel Laureate in Physics, 2009, was stricken with this devastating disease.

More than 36 million people worldwide were estimated to suffer from Alzheimer's disease (AD) in 2009 and the patient number was expected to increase to 115 million in 2050. The incidence rate of AD is known to increase with age. At age over 65, the incidence rate is about 5% in the general population. At age over 80, the incidence rate increases to about 20%, i.e., one in five. Current drug treatments can only improve symptoms and produce no profound cure. In recent years, several approaches aimed at inhibiting disease progression have advanced to clinical trials. Among them, strategies targeting the production and clearance of the Aβ peptide, which is thought to be a critical protein involved in the pathogenesis of the disease, are the most advanced.

Aβ peptide is the principal protein component of the Aβ plaques, which are found in the brains of AD patients during autopsy. The occurrence of the Aβ plaques, considered a cardinal feature of AD, provides the only confirmed diagnosis of the disease. Extensive researches in past decades have indicated a central role for the Aβ peptide in the disease process where the Aβ peptides assemble (aggregate) into Aβ fibrils which exert a cytotoxic effect towards the neurons and initiate the pathogenic cascade. Recent studies showed that oligomeric, prefibrillar and diffusible assemblies of Aβ peptides are also deleterious. The ability of this peptide to form Aβ fibrils seems to be largely sequence-independent, and many proteins can form structures with the characteristic cross-β stacking perpendicular to the long axis of the fiber.

Although a consensus mechanism for the pathogenic oligomeric assembly has yet to emerge, the idea of finding some brain-penetrating small molecules that can interfere with the interactions among the Aβ peptide monomers and thus inhibit the formation of the neurotoxic oligomers and the resulting Aβ plaques is an attractive approach to treating/preventing the disease. The use of agents that stabilize the monomer, interfere with the aggregation process (amyloidogenesis) and allow for the isolation of the intermediate species will help to elucidate the molecular mechanism of Aβ fibril formation. In addition, imaging agents that can specifically bind Aβ fibrils and plaques in vitro and in vivo are of paramount importance for studying the pathological events of the disease, disease diagnosis and monitoring of therapeutic treatment.

We have previously shown that carbazole-based fluorophores are highly sensitive fluorescent light-up probe for double strand DNA and strongly active two-photon absorption dyes for two-photon excited bioimaging, the disclosure of which is incorporated by reference herein. Recently, the mono-cyanine fluorophore has also been found to exhibit binding affinity towards beta amyloid (Aβ) peptide concomitant with strong fluorescent enhancement. These findings provide us the lead molecular structure to design and synthesize novel functional carbazole-based fluorophores for imaging and inhibition the aggregation of Aβ peptides.

Citation or identification of any reference in this section or any other section of this application shall not be construed as an admission that such reference is available as prior art for the present application.

SUMMARY OF INVENTION

Accordingly, the first objective of the presently claimed invention relates to a method of reducing and preventing aggregation of beta-amyloid peptides for Alzheimer's disease (AD) as well as of treating and/or preventing Alzheimer's disease by using carbazole-based fluorophores.

In the first aspect of the present invention there is provided a method for treatment and/or prevention of beta-amyloid (Aβ) peptides aggregation-associated diseases by using carbazole-based fluorophores comprising a formula S series:

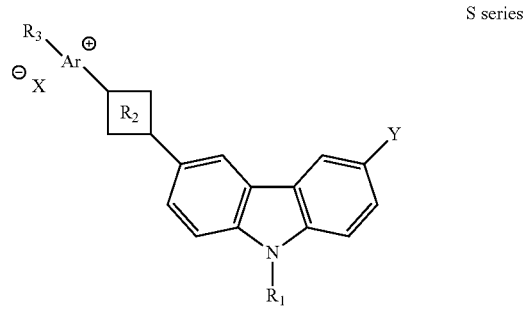

S series wherein said method comprising:
binding said carbazole-based fluorophores to Aβ peptides, oligomers and/or fibrils thereof;
inhibiting the growth and/or aggregation of said Aβ peptides, oligomers and/or fibrils upon said binding; and
protecting neuronal cells against the neurotoxic activities of the Aβ oligomers and/or fibrils;
wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;

$R_1$ is a radical selected from the group consisting of polyethylene glycol chain, alkyl, substituted alkyl, peptide chain, glycosidyl, and $C(O)NHCH((CH_2CH_2O)_2CH_3)_2$;

$R_2$ is selected from the group consisting of ethenyl, ethynyl, azo and azomethinyl.

$R_3$ is a radical selected from the group consisting of HO-alkyl, alkyl-COOalkyl, alkyl-CONH$_2$, alkyl-CONHalkyl, polyethylene glycol chain;

X is an anion selected from the group consisting of F, Cl, Br, I, HSO$_4$, H$_2$PO$_4$, HCO$_3$, tosylate, and mesylate;

Y is selected from the group consisting of H, F, Cl, OH, and OCH$_3$.

In a first embodiment of the first aspect of the present invention there is provided a method wherein Ar is selected from a quinolinyl or substituted quinolinyl; said $R_1$ is a 2-(2-methoxyethoxy)ethoxy; said $R_2$ is an ethenyl; $R_3$ is a 2-hydroxyethyl or acetamide or acetate or 2-(2-methoxyethoxy)ethoxy; said X is a chloride or bromide or iodide and said Y is a H or F which are represented by the formula F-SLOH, SLAD, SLAce, and SLG:

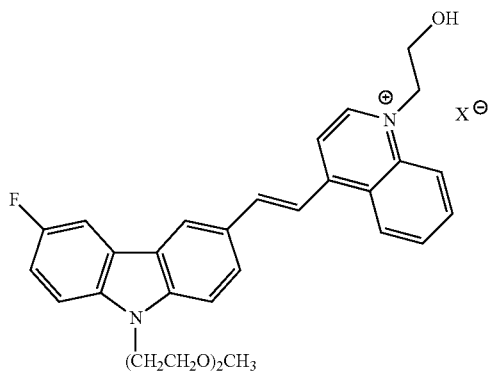

In a second embodiment of the first aspect of the present invention there is provided a method wherein the carbazole-based fluorophores are non-toxic and/or are able to pass through the blood-brain barrier.

In a third embodiment of the first aspect of the present invention there is provided a method wherein the carbazole-based fluorophores are administered in vitro and/or in vivo.

Throughout this specification, unless the context requires otherwise, the word "include" or "comprise" or variations such as "includes" or "comprises" or "comprising", will be understood to imply the inclusion of a stated integer or group of integers but not the exclusion of any other integer or group of integers. It is also noted that in this disclosure and particularly in the claims and/or paragraphs, terms such as "included", "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF DRAWINGS

The above and other objects and features of the present invention will become apparent from the following description of the present invention, when taken in conjunction with the accompanying drawings, in which:

FIG. 1 shows the fluorescence spectra of SPM, SPOH, SLM, SLOH, SLE, SLOH-Pr, Me-SLM, SAM, and SAOH (1 µM) in phosphate buffer upon addition of various concentrations of Aβ(1-40) fibrils prepared from Aβ$_{40}$ with seed incubated at 37° C. for an hour in buffer (left column). FIG. 1A shows the fluorescence spectra of SPM in various concentrations of Aβ(1-40) fibrils. FIG. 1C shows the fluorescence spectra of SPOH in various concentrations of Aβ(1-40) fibrils. FIG. 1E shows the fluorescence spectra of SLM in various concentrations of Aβ(1-40) fibrils. FIG. 1G shows the fluorescence spectra of SLOH in various concentrations of Aβ(1-40) fibrils. FIG. 1I shows the fluorescence spectra of SLE in various concentrations of Aβ(1-40) fibrils. FIG. 1K shows the fluorescence spectra of SLOH-Pr in various concentrations of Aβ(1-40) fibrils. FIG. 1M shows the fluorescence spectra of Me-SLM in various concentrations of Aβ(1-40) fibrils. FIG. 1O shows the fluorescence spectra of SAM in various concentrations of Aβ(1-40) fibrils. FIG. 1Q shows the fluorescence spectra of SAOH in various concentrations of Aβ(1-40) fibrils. FIG. 1 also shows the fluorescence spectra of SPM, SPOH, SLM, SLOH, SLE, SLOH-Pr, Me-SLM, SAM, and SAOH (1 µM) in phosphate buffer itself, in the presence of 100 equv of Aβ$_{40}$ in monomeric form, and in the presence of 100 equv of Aβ$_{40}$ in fibril state in phosphate buffer (right column). FIG. 1B shows the fluorescence spectra of SPM on its own and in the presence of two different forms of Aβ$_{40}$. FIG. 1D shows the fluorescence spectra of SPOH on its own and in the presence of two different forms of Aβ$_{40}$. FIG. 1F shows the fluorescence spectra of SLM on its own and in the presence of two different forms of Aβ$_{40}$. FIG. 1H shows the fluorescence spectra of SLOH on its own and in the presence of two different forms of Aβ$_{40}$. FIG. 1J shows the fluorescence spectra of SLE on its own and in the presence of two different forms of Aβ$_{40}$. FIG. 1L shows the fluorescence spectra of SLOH-Pr on its own and in the presence of two different forms of Aβ$_{40}$. FIG. 1N shows the fluorescence spectra of Me-SLM on its own and in the presence of two different forms of Aβ$_{40}$. FIG. 1P shows the fluorescence spectra of SAM on its own and in the presence of two different forms of Aβ$_{40}$. FIG. 1R shows the fluorescence spectra of SAOH on its own and in the presence of two different forms of Aβ$_{40}$.

FIG. 2 shows the fluorescence spectra of SPM, SPOH, SLM and SLOH in phosphate buffer (1 µM) upon addition of various concentrations of Aβ(1-40) and Aβ(1-42), respectively. FIG. 2A shows the fluorescence spectra of SPM in various concentrations of Aβ(1-40). FIG. 2B shows the fluorescence spectra of SPM in various concentrations of Aβ(1-42). FIG. 2C shows the fluorescence spectra of SPOH in various concentrations of Aβ(1-40). FIG. 2D shows the fluorescence spectra of SPOH in various concentrations of Aβ(1-42). FIG. 2E shows the fluorescence spectra of SLM in various concentrations of Aβ(1-40). FIG. 2F shows the fluorescence spectra of SLM in various concentrations of Aβ(1-42). FIG. 2G shows the fluorescence spectra of SLOH in various concentrations of Aβ(1-40). FIG. 2H shows the fluorescence spectra of SLOH in various concentrations of Aβ(1-42).

FIG. 3 shows TIRFM images of Aβ fibrils after incubation with the carbazole-based fluorophores, SPM (FIG. 3A) excited at 445 nm and SLM (FIG. 3B) and SLOH (FIG. 3C) excited at 488 nm, respectively.

FIG. 4 shows in vitro fluorescence imaging of neuronal cells by using the carbazole-based fluorophore, SLOH (FIG. 4A) The lambda scans of the images match well with the fluorescence spectrum of the SLOH (FIG. 4B).

FIG. 5 shows absorption and fluorescence spectra of the carbazole-based fluorophores, SAM (FIG. 5A) and SAOH (FIG. 5B) in phosphate buffer solution.

FIG. 6 shows CD spectra of Aβ(1-40) peptide (FIG. 6A) and fibrils (FIG. 6B) in the absence and presence of SLOH (1:1) (20 µM).

FIG. 7 shows TIRFM images of Aβ fibrils (FIG. 7A) and Aβ peptide after incubation with the carbazole-based fluorophore, SLOH (FIG. 7B), SAOH (FIG. 7C), SLE (FIG. 7D), SLOH-Pr (FIG. 7E), and Me-SLM (FIG. 7F). FIGS. 7B, 7C, 7E and 7F show an inhibition of Aβ fibril formation from the Aβ monomer by SLOH and SAOH. These images were obtained by an addition of ThT dye excited at 445 nm.

FIG. 8 shows TEM images of Aβ fibril growth from Aβ peptide (50 µM) seeded for 1 hr at 37° C. in the absence (FIG. 8A) and the presence of SLOH (FIG. 8B).

FIG. 9 shows ThT, SLM and SLOH fluorescence binding assays for 50 µM Aβ$_{40}$ fibrillation (FIG. 9A). Average length of 1 h incubated Aβ40-fibril measured from TIRFM images after 1 h seed-mediated incubation of Aβ40 monomer with (bottom axis, bars) and without (top axis, scatter point) SLOH (50 µM) added at different time points (0, 10, 20, 40 and 60 min) within an one hour-incubation. (FIG. 9B).

FIG. 10 shows cytotoxicities of the carbazole-based SLOH (FIG. 10A), SLOH-Pr (FIG. 10B), Me-SLM (FIG. 10C) and SAOH (FIG. 10D) towards the SH-SY5Y neuronal cell with MTT assays.

FIG. 11 shows cytotoxicities of Aβ peptide monomer (DM/M), oligomers (DM S/MS) and fibrils (DF/F) towards the SH-SY5Y neuronal cell in the absence and the presence of SLOH (50 µM) (FIG. 11A), SLE (FIG. 11B), SLOH-Pr (FIG. 11C), Me-SLM (FIG. 11D) after 2 hr, 6 hr, and 24 hr incubations.

FIG. 12 shows fluorescence images of transgenic mice brain with tail vein injection of SLOH and co-stained with the Aβ labeling dye, ThT or Aβ antibody with DAB stain. Fluorescence image corresponding to SLOH fluorescence captured at 550-630 nm under excitation at 488 nm (FIG. 12A); ThT fluorescence captured at 470-550 nm under excitation at 458 nm (FIG. 12B); and overlapped images of previous two images (FIG. 12C). The overlapped image revealed the colocalization of fluorescence signals of SLOH and ThT in cellular components. Differential Interference Contrast (DIC) image of DAB stained brain slide of transgenic mice (FIG. 12D). Fluorescence image of same slide corresponding to SLOH fluorescence captured at 550-630 nm under excitation at 488 nm (FIG. 12E); and overlapped images of previous two images (FIG. 12F). The overlapped image revealed the colocalization of fluorescence signals of SLOH and Aβ antibody in cellular components.

FIG. 14 shows the general chemical structures of carbazole-based fluorophores, including S series.

FIG. 19 shows (FIG. 19A) the influence of F-SLOH, and SLAD suppression on the toxicity level against various species of Aβ-induced cytotoxicity towards primary cortical neural cells; (FIG. 19B) shows the reduction of the ROS induced by the Aβ species in primary cortical neural cells.

FIG. 20 shows the fluorescence images of mice brain with tail vein injection of SLAD (upper panel) and co-stained with the Aβ labeling dye, and Aβ antibody with DAB stain. Fluorescence image corresponding to SLAD fluorescence captured at 550-630 nm under excitation at 488 nm (FIG. 20A); Differential Interference Contrast (DIC) image (FIG. 20B); and overlapped images of previous two images (FIG. 20C). Differential Interference Contrast (DIC) image of DAB stained brain slide of transgenic mice (FIG. 20D). Fluorescence image of same slide corresponding to SLAD fluorescence captured at 550-630 nm under excitation at 488 nm (FIG. 20E); and overlapped images of previous two images (FIG. 20F). The overlapped image revealed the colocalization of fluorescence signals of SLAD and Aβ antibody in cellular components.

DETAILED DESCRIPTION OF THE INVENTION

Figures 13, 13A:
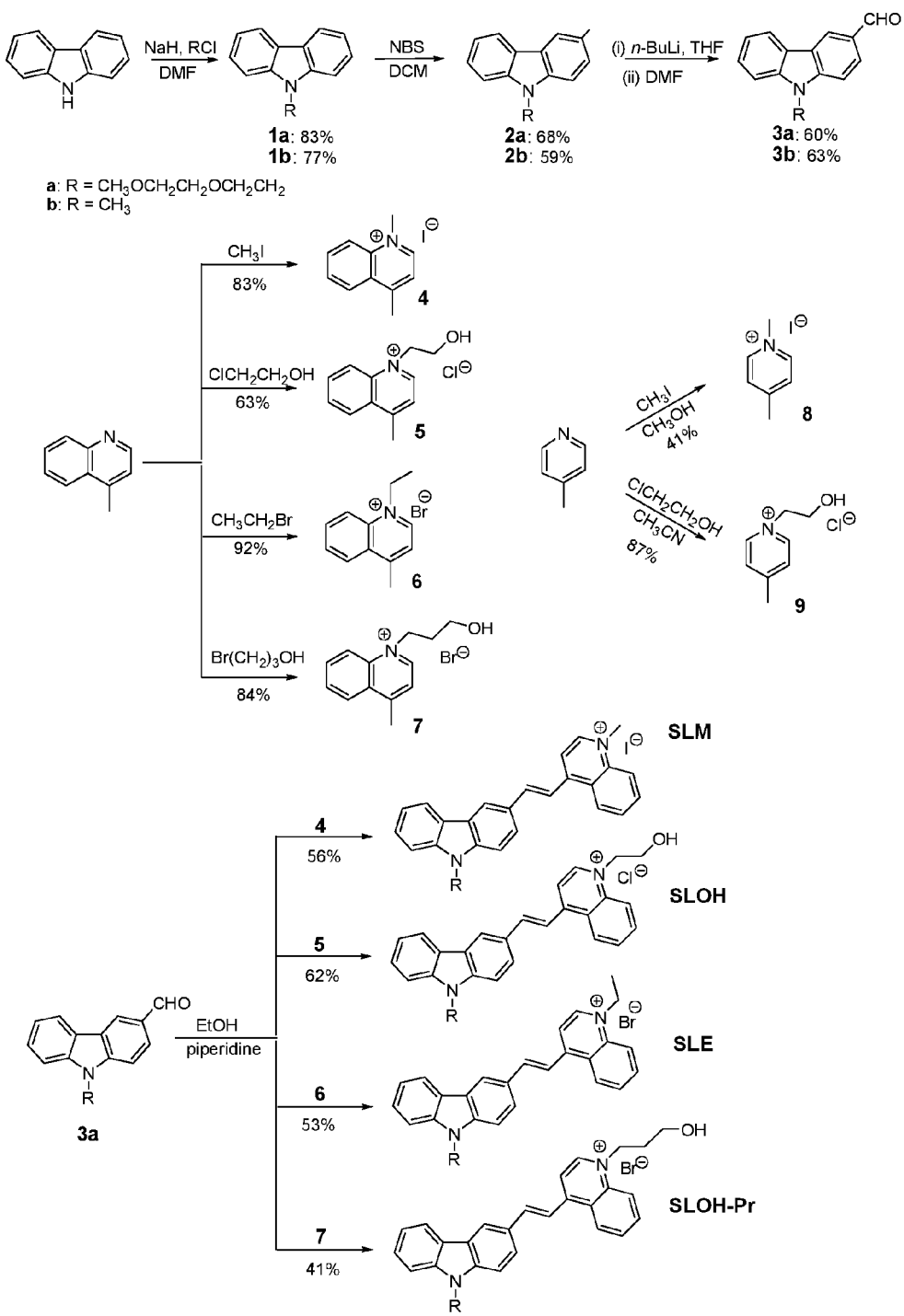
FIG. 13 shows synthesis of carbazole-based fluorophores, SLM, SLOH, SLE, SLOH-Pr (FIG. 13A) and SPM, SPOH, Me-SLM, SAM, and SAOH (FIG. 13B).
Figures 13, 13B:
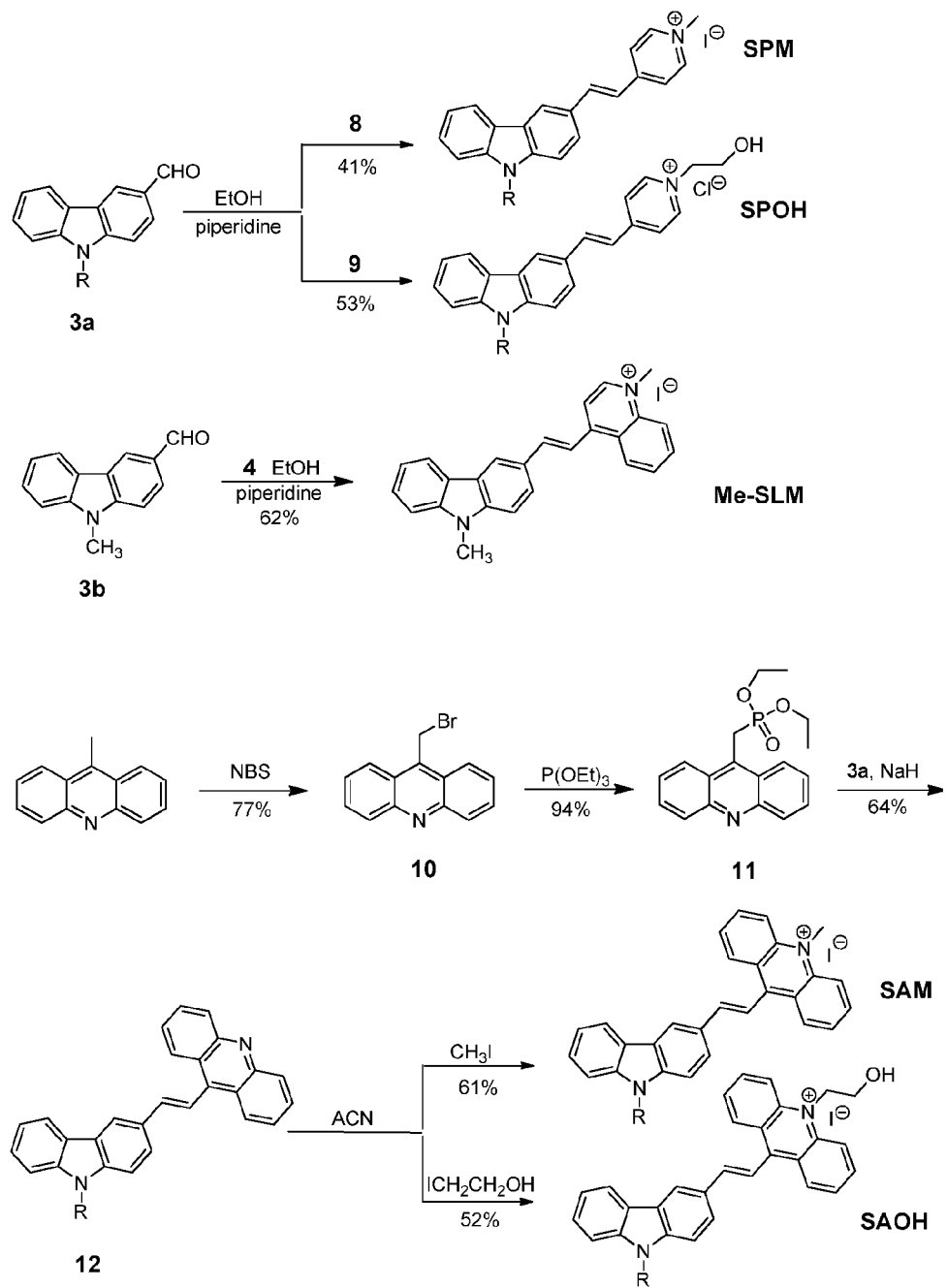

The presently claimed invention is further illustrated by the following experiments or embodiments which should be understood that the subject matters disclosed in the experiments or embodiments may only be used for illustrative purpose but are not intended to limit the scope of the presently claimed invention:

The general chemical structures of carbazole-based fluorophores, including S or V series, are shown as follows:

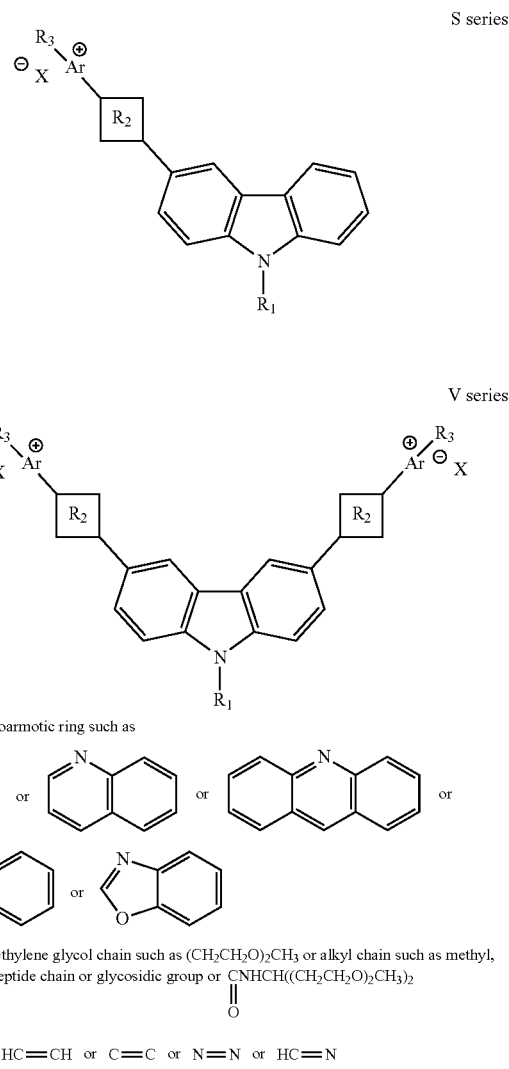

wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; $R_1$ is a radical selected from the group consisting of polyethylene glycol chain, alkyl, substituted alkyl, peptide chain, glycosidyl, and C(O)NHCH ((CH$_2$CH$_2$O)$_2$CH$_3$)$_2$; $R_2$ is selected from the group consisting of ethenyl, ethynyl, azo and azomethinyl; $R_3$ is a radical selected from the group consisting of alkyl, HO-alkyl, HS-alkyl, H$_2$N-alkyl, HNalkyl-alkyl, HOOC-alkyl, (alkyl)$_3$N$^+$-alkyl, and (Ph)$_3$P$^+$-alkyl; X is an anion selected from the group consisting of F, Cl, Br, I, HSO$_4$, H$_2$PO$_4$, HCO$_3$, tosylate, and mesylate.

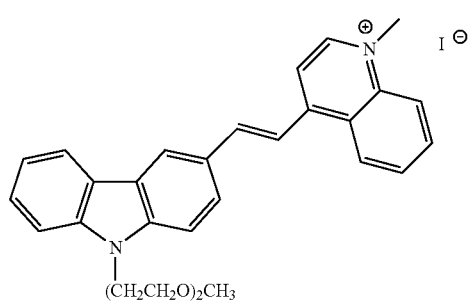

SLM

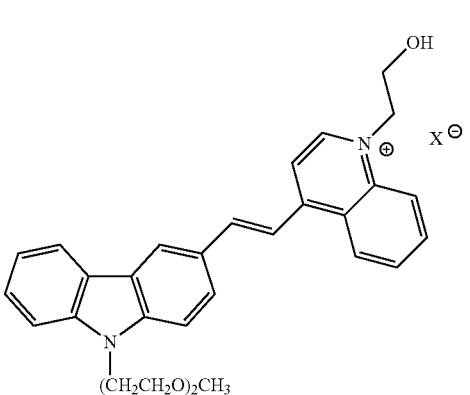

SLOH

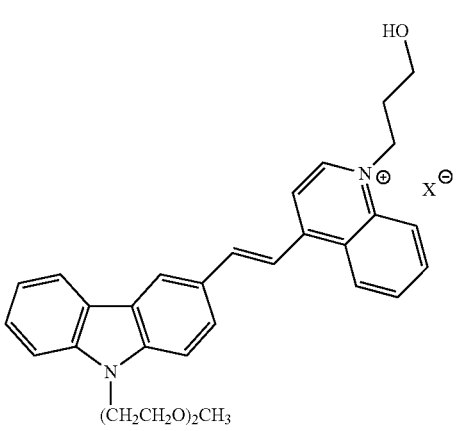

SLE

SLOH-Pr

In one embodiment, Ar is a quinolinyl or substituted quinolinyl; $R_1$ is a 2-(2-methoxyethoxy)ethoxy; $R_2$ is an ethenyl; $R_3$ is a methyl, 2-hydroxyethyl, ethyl or 3-hydroxypropyl; and X is a chloride, bromide or iodide, and the compounds of which are represented by the above formula "SLM", "SLOH", "SLE" and "SLOH-Pr", respectively.

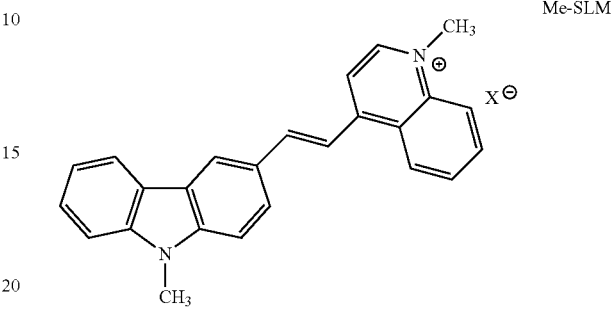

Me-SLM

In another embodiment, Ar is a quinolinyl or substituted quinolinyl; $R_1$ is a methyl; $R_2$ is an ethenyl; $R_3$ is a methyl; and X is a chloride, bromide or iodide, the compounds of which are represented by the above formula Me-SLM.

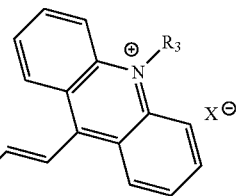

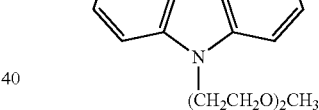

SAM: $R_3$ = $CH_3$
SAOH: $R_3$ = $CH_2CH_3OH$

In a further embodiment, Ar is an acridinyl or substituted acridinyl; $R_1$ is a 2-(2-methoxy-ethoxy)ethoxy; $R_2$ is an ethenyl; $R_3$ is a methyl or 2-hydroxyethyl; and X is selected from a chloride, bromide or iodide, and the fluorophores of which are represented by the above formula SAM and SAOH, respectively, where the difference between the compounds of SAM and SAOH is the substitutent at $R_3$.

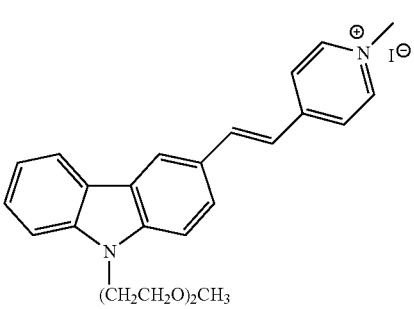

SPM

-continued

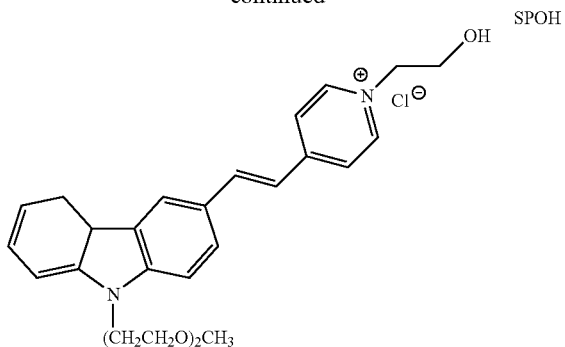
SPOH

In other embodiment, Ar is selected from a pyridinyl or substituted pyridinyl, $R_1$ is a 2-(2-methoxyethoxy)ethoxy; $R_2$ is an ethenyl; $R_3$ is selected from a methyl or 2-hydroxyethyl; and X is selected from a chloride, bromide or iodide, the compounds of which are represented by the formula SPM and SPOH, respectively.

A novel series of water-soluble carbazole-based fluorophores has been designed and developed. These molecules were found to bind to Aβ(1-40) and Aβ(1-42) peptides and, more specifically, their oligomers, and fibrils with strong fluorescence enhancement, therefore allowing direct imaging and detection for the Aβ peptides, oligomers and their fibrils (FIG. 1). Upon binding with Aβ peptides, there is about 8- to about 82-fold increase in fluorescence intensity concomitant with the substantial blue shifts (Δλ=14-22 nm) in the emission spectra of the fluorophores (FIG. 2). Interestingly, the fluorescence enhancement is much stronger for fibrils than peptides. (e.g. $F_{fibril}/F_{SLOH}$=81.5 vs. $F_{peptide}/F_{SLOH}$=6.3). Because of such strong increase in fluorescence, the signal-to-noise ratio is so high that imaging of single fibrils is possible. (FIG. 3) Compared to common commercial labeling dyes for Aβ such as Thioflavin-T and Congo Red, the carbazole-based fluorophores of the present invention provide an advantage of a wide range of excitation and emission tuning in visible to infra-red region (FIG. 4). Some of these molecules, e.g., SAM and SAOH, even emit at ~760 nm (FIG. 5), which can potentially be used for near infra-red fluorescence imaging. In addition to fluorescence titration, the binding of Aβ peptide and fibril with the carbazole-based fluorophores of the present invention were further confirmed by circular dichroism spectroscopy (FIG. 6), and electrospray ionization-mass spectrometry (ESI-MS). Total Internal Reflection Fluorescence Microscope (TIRFM) technique developed by us was used to investigate the inhibition effects of these functional fluorophores on Aβ fibril formation (FIG. 7). Remarkably, some of these molecules, e.g., SLOH, SLE, SLOH-Pr, Me-SLM, SAM, and SAOH, were found to inhibit Aβ peptide aggregation and prevent fibril growth (FIG. 7). Such inhibitory effect was further confirmed by Transmission Electron Microscopy (TEM) study (FIG. 8).

The inhibitory effect of the carbazole-based fluorophores of the present invention on Aβ fibril growth was further investigated by measuring the (average) length of the Aβ fibrils formed after incubation of the Aβ monomers for 60 min with additions of SLOH at different time points during this period (FIG. 9). Parallel experiments conducted without any addition of SLOH were used as controls. FIG. 9 shows that an addition of SLOH to the Aβ monomer strongly arrests its fibril growth. These results clearly indicate that the inhibitory effect of these carbazole-based fluorophores on Aβ aggregation is instantaneous.

To ascertain its potential clinical application, the cytotoxicities of these carbazole-based molecules, SLOH, SLOH-Pr, Me-SLM, and SAOH towards the neuronal cell, i.e., SH-SY5Y cell line, were investigated by MTT [3-(4,5-dimethylthiazol-2-yl)-2,5-diphenyltetrazolium bromide] reduction assay. The results obtained (FIG. 10) showed that these molecules were essentially non-toxic (≤20%) to the neuronal cell particularly at low dosage.

Since it is the Aβ oligomers and fibrils that are neurotoxic, further experiments with these carbazole-based molecules conducted in the presence of the Aβ monomer (non-toxic), the neurotoxic Aβ oligomers and fibrils showed that the neuronal cells became protected from the neurotoxic effects of the Aβ oligomers and fibrils when incubated with carbazole-based molecules SLOH and SAOH for 2 and 6 hours (FIG. 11).

However, in order for the observed neuroprotective effect to be clinically useful, these molecules need to be able to pass through the blood-brain barrier. The ability of these molecules to penetrate the blood-brain barrier was demonstrated in transgenic mice (FIG. 12). In addition, FIGS. 12D-F shows the selectivity of SLOH towards Aβ plaques as confirmed with Aβ antibody which was used to identify the Aβ plaques in transgenic mice's brain.

In summary, carbazole-based fluorophores of the present invention have been shown to bind to $Aβ_{(1-40)}$ and $Aβ_{(1-42)}$ as well as Aβ aggregates with dramatic fluorescence enhancement, thus allowing their direct imaging and labeling as well as the use of TIRFM technique to study the effects of these molecules on Aβ aggregation/fibrillation. Some embodiments of the carbazole-based fluorophores, for instance, SLOH and SAOH, have been shown to be a potent inhibitor of Aβ aggregation, non-toxic and exhibiting a protective effect against the neurotoxic activities of the Aβ oligomers and fibrils towards neuronal cells. These properties, together with the ability to cross the blood-brain barrier and target the Aβ plaques, render the fluorophores of the present invention a potential neuroprotective and, perhaps, therapeutic agent for Alzheimer's disease.

The following compositions according to the invention were prepared and exemplified as shown in FIG. 13. By adapting the convergent approach established previously, the Knoevenagel reaction of carbazolyl-3-aldehyde and the corresponding 4-methylpyridium or 4-methylquinolinium halide was used as the key step to synthesize various carbazole-based cyanines. Alkylation of carbazole with ethylene glycol chloride and methyl iodide in the presence of NaH in DMF gave alkylated carbazole 1a and 1b respectively. Monobromination of 1a and 1b in the presence of NBS gave alkylated 3-bromocarbazole, 2a and 2b, respectively. Formylation of 2a and 2b via lithiation bromide exchange at low temperature followed by the subsequent quenching with DMF afforded carbazolyl-3-aldehyde, 3a and 3b, respectively, in moderate yield. Alkylation of lepidine or picoline was carried out in methanol or acetonitrile affording the corresponding halide, 4-9 in good to high yield. The Knoevenagel reaction of aldehyde 3a or 3b and the corresponding 4-methylpyridium or 4-methylquinolinium halide in the presence of piperidine in ethanol afforded the corresponding carbazole-based cyanines in a moderate yield. For the acridine-based cyanines dyes, 9-methylacridine was first brominated with NBS affording brominated product 10, which gave phosphonate ester 11 by refluxing with triethyl phosphite. Condensation of phosphonate 11 and aldehyde 3a in the presence of NaH afforded 12, which was alkylated with methyl iodide and 2-iodoethanol to give SAM and SAOH, respectively. All the cyanines were fully characterized with spectroscopic techniques and found to be in good agreement with its structure.

All the solvents were dried by the standard methods wherever needed. $^1$H NMR spectra were recorded using a Bruker-400 NMR spectrometer and referenced to the residue CHCl$_3$ 7.26 ppm or DMSO-d$_6$ 2.5 ppm. $^{13}$C NMR spectra were recorded using a Bruker-400 NMR spectrometer and referenced to the CDCl$_3$ 77 ppm or DMSO-d$_6$ 39.5 ppm. Mass Spectroscopy (MS) measurements were carried out by using fast atom bombardment on the API ASTER Pulser I Hybrid Mass Spectrometer or matrix-assisted laser desorption ionization-time-of-flight (MALDI-TOF) technique. Elemental analysis was carried on the CARLO ERBA 1106 Elemental Analyzer. Compound 8 and SPM were synthesized according to previous procedure.

Although the cause and progression of AD are not well understood yet, early detection and diagnosis allows preventive and delaying measures for the progression to AD. Thus, the development of a powerful imaging technique with sensitivity at the molecular level for AD diagnosis is crucial to assess the disease status as well as the evaluation of effectiveness of potential AD drugs. Various imaging techniques including magnetic resonance imaging, positron emission tomography, near-infrared fluorescence imaging and multiphoton excited imaging have been explored for amyloid plaques imaging. All these techniques require a functional probe that can selectively target the Aβ species.

Apart from the use in direct imaging or labeling of Aβ aggregates, the carbazole-based fluorophores of the present invention is also useful as a magnetic resonance imaging (MRI) contrast agent that bind beta amyloid peptides. By conjugating appropriate paramagnetic metal complexes to these carbazole-based fluorophores, these compounds can potentially be developed into beta-amyloid peptide-specific MRI contrast agents. To convert these Aβ fibril-specific carbazole-based fluorophores dyes into MRI contrast agents, we can attach strongly paramagnetic and kinetically inert metal complexes, such as the gadolinium(III), iron(III), and manganese(II) complexes, via the R$_1$ side chain of the carbazole moiety to these fluorophores. Gd(III)-based chelates, such as [Gd(DTPA)(H$_2$O)]$^{2-}$ (DTPA=diethylenetriaminepentaacetic acid), approved for clinical use in 1988 and commercially known as Magnevist, are attractive candidates. Recently, further enhancement of the MRI contrast properties of these Gd(III) complexes was achieved by allowing the coordination of a second inner-sphere water molecule, which raised the relaxivity of the conventional Gd(III) contrast agents from 4-5 mM$^{-1}$ s$^{-1}$ (at 20 MHz field strength) to 10.5 mM$^{-1}$ s$^{-1}$, in the Gd-TREN-1-Me-3,2-HOPO complex, [1] (where TREN=tris(2-aminoethyl), HOPO=hydroxypyridinone, structure shown below).

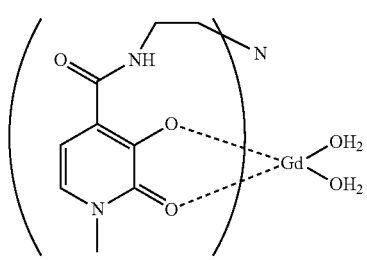

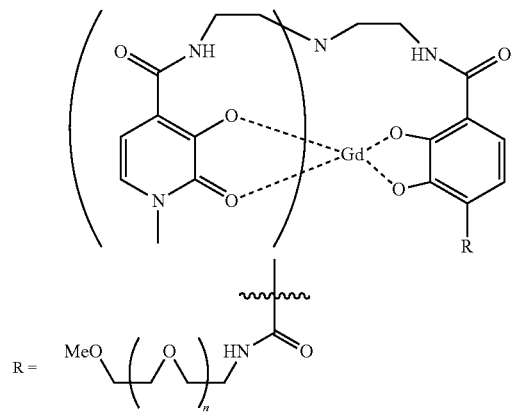

A slight modification of one of the hydroxypyridinone ligands of the Gd(III) complex, shown in [2], allows flexible attachment to the carbazole moiety of Aβ fibril-specific dyes via, for example, a polyethylene glycol (PEG) linkage.

More recently, a series of $^1$H/$^{19}$F dual MR imaging agents based on CF$_3$-labeled lanthanide(III) complexes (Ln=Gd, Tb, Dy, Ho, Er, Tm) with amide-substituted 1,4,7,10-tetraazacyclododecane ligand have been designed. An example of this ligand system bearing a CF$_3$ reporter group is shown in [3].

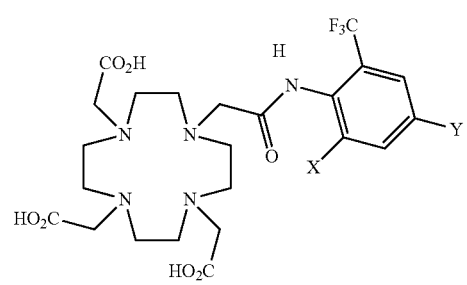

The advantage of $^{19}$F MRI is the exquisite sensitivity of the $^{19}$F shift of the reporter group to its local chemical environment, thus opening up the possibility of responsive MRI to detect changes in local pH, oxygen stress, etc. The fact that standard MRI instruments can be easily tuned from $^1$H to $^{19}$F nuclei, which have very similar magnetic properties, is an added bonus of this technique. This ligand system is also amenable to coupling (e.g., at the —X or —Y positions indicated) to the carbazole moiety of the carbazole-based fluorophores dyes.

Synthesis Examples 9-(2-(2-methoxyethoxy)ethyl)-9H-carbazole (1a)

To a solution of carbazole (3.34 g, 20 mmol) in DMF (80 mL) at 0° C. was added NaH (0.72 g, 30 mmol). After heating to 80° C. for 1.5 h, 1-chloro-2-(2-methoxyethoxy)ethane (3.31 g, 24 mmol) was added dropwise. The resulting mixture was kept at 80° C. overnight. After cooling down to 0° C., the reaction mixture was carefully quenched with water and extracted with ethyl acetate three times. The combined organic phase was washed with water and brine. Then the organic layer was dried over anhydrous sodium sulfate and the solvent was removed. The residue was purified by silica gel chromatography using petroleum ether and ethyl acetate as eluent (EA:PE=1:3) to afford alkylated carbazole 1a (4.46 g) as brown oil in 83% yield. $^1$H NMR (400 MHz, CDCl$_3$) δ 8.09 (d, J=7.6 Hz, 2H), 7.46 (m, 4H), 7.23 (m, 2H), 4.51 (t, J=6.4 Hz, 2H), 3.86 (t, J=6.4 Hz, 2H), 3.52 (m, 2H), 3.42 (m, 2H), 3.31 (s, 3H). $^{13}$C NMR (400 MHz, CDCl$_3$) δ 140.5, 125.6, 122.8, 120.2, 118.9, 108.7, 71.8, 70.7, 69.1, 59.0, 43.0. MS (FAB) m/z Calcd for C$_{17}$H$_{19}$NO$_2$ 269.1. Found 269.2 [M]$^+$.

9-methyl-9H-carbazole (1b)

To a solution of carbazole (3.34 g, 20 mmol) in DMF (80 mL) at 0° C. was added NaH (0.72 g, 30 mmol). After heating at 80° C. for 1.5 h, iodomethane (3.4 g, 24 mmol) was added dropwise. The resulting mixture was kept at 80° C. overnight. After cooling down to 0° C., the reaction mixture was carefully quenched with water and extracted with ethyl acetate three times. The combined organic phase was washed with water and brine. Then the organic layer was dried over anhydrous sodium sulfate and the solvent was removed. The residue was purified by silica gel chromatography using petroleum ether and ethyl acetate as eluent (EA:PE=1:5) to afford methylated carbazole 1b (2.78 g) as yellow oil in 77% yield. $^1$H NMR (400 MHz, CDCl$_3$) δ 8.08 (d, J=8.0 Hz, 2H), 7.46 (t, J=8.0 Hz, 2H), 7.36 (d, J=8.0 Hz, 2H), 7.22 (t, J=8.0 Hz, 2H), 3.79 (s, 3H). $^{13}$C NMR (400 MHz, CDCl$_3$) δ 140.9, 125.6, 122.7, 120.2, 118.8, 108.4, 28.9.

3-bromo-9-(2-(2-methoxyethoxy)ethyl)-9H-carbazole (2a)

To a solution of 1a (2 g, 7.4 mmol) in dichloromethane (60 mL) was added NBS (1.3 g, 7.4 mmol) portionwise in an ice-water bath. After complete addition, the solution mixture was warmed to room temperature and stirred overnight. The resulting solution was washed with water and brine. The organic phase was dried over anhydrous sodium sulfate and the solvent was removed. The residue was purified by silica gel chromatography using ethyl acetate and petroleum ether (EA:PE=1:5) as eluent to afford 2a (1.75 g) in 68% yield as an oil that can turn into solid after standing. $^1$H NMR (400 MHz, CDCl$_3$) δ 8.16 (d, J=2.0 Hz, 1H), 8.01 (d, J=8.0 Hz, 1H), 7.51 (dd, J=8.0 Hz, 2.0 Hz, 1H), 7.44 (m, 2H), 7.34 (d, J=8.4 Hz, 1H), 7.22 (m, 1H), 4.46 (t, J=6.0 Hz, 2H), 3.83 (t, J=6.0 Hz, 2H), 3.48 (m, 2H), 3.39 (m, 2H), 3.28 (s, 3H). $^{13}$C NMR (400 MHz, CDCl$_3$) δ 140.7, 139.2, 128.2, 126.3, 124.5, 122.8, 121.8, 120.4, 119.3, 111.7, 110.4, 109.0, 71.8, 70.7, 69.1, 59.0, 43.2. MS (FAB) m/z Calcd for C$_{17}$H$_{18}$BrNO$_2$ 347.0. Found 347.3 [M]$^+$.

3-bromo-9-methyl-9H-carbazole (2b)

To a solution of 1b (2.5 g, 13.8 mmol) in dichloromethane (80 mL) was added NBS (2.4 g, 13.8 mmol) portion-wise in an ice-water bath. After complete addition, the solution mixture was warmed to room temperature and stirred overnight. The resulting solution was washed with water and brine. The organic phase was dried over anhydrous sodium sulfate and the solvent was removed. The residue was purified by silica gel chromatography using ethyl acetate and petroleum ether (EA:PE=1:10) as eluent to afford 2b (2.11 g) in 59% yield. $^1$H NMR (400 MHz, CDCl$_3$) δ 8.19 (d, J=2.0 Hz, 1H), 8.03 (d, J=8.0 Hz, 1H), 7.54 (dd, J=8.8 Hz, J=2.0 Hz, 1H), 7.50 (td, J=8.0 Hz, J=1.2 Hz, 1H), 7.39 (d, J=8.0 Hz, 1H), 7.27-7.22 (m, 2H), 3.82 (s, 3H).

9-(2-(2-methoxyethoxy)ethyl)-9H-carbazole-3-carbaldehyde (3a)

To a solution of 2a (1.5 g, 4.3 mmol) in dried THF (45 mL) was added n-BuLi (3.5 mL 5.2 mmol) at −78° C. The resulting mixture was stirred at −78° C. for 1 h and then added with dried DMF (3 mL). The reaction mixture was allowed to warm to room temperature and stirred overnight before quenched with aqueous ammonia chloride solution. Water was added and extracted with ethyl acetate three times. The combined organic phase was washed with brine and dried over anhydrous sodium sulfate. After removing the solvent, the residue was purified by silica gel chromatography using ethyl acetate and petroleum ether (EA:PE=1:2) as eluent to afford 3a (0.76 g) as yellow solid in 60% yield. $^1$H NMR (400 MHz, CDCl$_3$) δ 10.07 (s, 1H), 8.58 (d, J=0.8 Hz, 1H), 8.13 (d, J=8.0 Hz, 1H), 7.98 (dd, J=8.8 Hz, 0.8 Hz, 1H), 7.51 (m, 3H), 7.30 (m, 1H), 4.53 (t, J=6.0 Hz, 2H), 3.87 (t, J=6.0 Hz, 2H), 3.49 (m, 2H), 3.38 (m, 2H), 3.26 (s, 3H). $^{13}$C NMR (400 MHz, CDCl$_3$) δ 191.8, 144.3, 141.1, 128.5, 127.1, 126.6, 123.7, 123.0, 122.9, 120.6, 120.4, 109.4, 109.3, 71.8, 70.8, 69.1, 59.0, 43.4. MS (FAB) m/z Calcd for C$_{18}$H$_{19}$NO$_3$ 297.1. Found 297.3 [M]$^+$.

9-methyl-9H-carbazole-3-carbaldehyde (3b)

To a solution of 2b (1.8 g, 6.9 mmol) in dried THF (45 mL) was added n-BuLi (3.3 mL 8.3 mmol) at −78° C. The resulting mixture was stirred at −78° C. for 1 h and then added with dried DMF (8 mL). The reaction mixture was allowed to warm to room temperature and stirred overnight before quenched with aqueous ammonia chloride solution. Water was added and extracted with ethyl acetate three times. The combined organic phase was washed with brine and dried over anhydrous sodium sulfate. After removing the solvent, the residue was purified by silica gel chromatography using ethyl acetate and petroleum ether (EA:PE=1:4) as eluent to afford 3b (0.86 g) in 60% yield. $^1$H NMR (400 MHz, CDCl$_3$) δ 9.58 (s, 1H), 7.79 (s, 1H), 7.49 (d, J=7.6 Hz, 1H), 7.41 (d, J=8.8 Hz, 1H), 7.09 (t, J=7.6 Hz), 6.90 (t, J=7.6 Hz, 1H), 6.77 (d, J=8.0 Hz, 1H), 6.61 (d, J=8.4 Hz, 1H), 3.00 (s, 3H). $^{13}$C NMR (400 MHz, CDCl$_3$) δ 190.9, 143.2, 140.5, 127.4, 125.8, 122.7, 121.7, 119.6, 119.4, 108.3, 107.6, 28.0.

1,4-dimethylquinolinium iodide (4)

A solution mixture of lepidine (0.66 g, 4.65 mmol) and iodomethane (1.32 g, 9.3 mmol) in methanol (30 mL) was heated to reflux in a sealed tube overnight. After cooling to room temperature, methanol was removed under vacuum. Anhydrous acetone was added to the residue and filtered. The resulting solid was washed with acetone and dried to afford iodide 4 (1.1 g) as yellow solid in 83% yield. $^1$H NMR (400 MHz, DMSO-d$_6$) δ 9.35 (d, J=6 Hz, 1H), 8.54 (d, J=8.8 Hz, 1H), 8.49 (d, J=8.8 Hz, 1H), 8.27 (t, J=7.2 Hz, 1H), 8.07 (t, J=4.8 Hz, 1H), 8.05 (d, J=6 Hz, 1H), 4.57 (s, 3H), 3.00 (s, 3H). $^{13}$C NMR (400 MHz, DMSO-d$_6$) δ 158.1, 148.9, 137.6, 134.9, 129.6, 128.4, 126.8, 122.4, 119.5, 44.9, 19.6. MS (FAB) m/z Calcd for C$_{11}$H$_{12}$N$^+$ 158.0. Found 158.2 [M]$^+$.

1-(2-hydroxyethyl)-4-methylquinolinium chloride (5)

A solution mixture of lepidine (0.8 g, 5.6 mmol) and 2-chloroethanol (2.25 g, 28 mmol) in acetonitrile (15 mL) was heated to 120° C. in a sealed tube overnight. After cooling to room temperature, the solvent was removed. The resulting mixture was precipitate from methanol and ethyl acetate to give the desired product 5 (0.79 g) in 63% yield. $^1$H NMR (400 MHz, DMSO-$d_6$) δ 9.24 (d, J=6 Hz, 1H), 8.61 (d, J=7.2 Hz, 1H), 8.55 (d, J=7.2 Hz, 1H), 8.25 (m, 1H), 8.06 (m, 2H), 5.15 (br, 1H), 5.08 (t, J=4.8 Hz, 2H), 3.91 (t, J=4.8 Hz, 2H), 3.01 (s, 3H). $^{13}$C NMR (400 MHz, DMSO-$d_6$) δ 158.8, 149.2, 137.1, 135.1, 129.7, 129.1, 127.2, 122.4, 119.5, 59.4, 59.0, 19.9. MS (FAB) m/z Calcd for $C_{12}H_{14}NO+$ 188.2. Found 188.2 [M]$^+$.

1-ethyl-4-methylquinolinium bromide (6)

A solution mixture of lepidine (0.5 g, 3.5 mmol) and bromoethane (1.96 g, 18 mmol) in acetonitrile (15 mL) was heated to reflux overnight. After cooling to room temperature, the solvent was removed. The resulting mixture was precipitate from methanol and ethyl acetate to give the desired product 6 (0.81 g) in 92% yield. $^1$H NMR (400 MHz, DMSO-$d_6$) δ 9.44 (d, J=6 Hz, 1H), 8.60 (d, J=9.2 Hz, 1H), 8.54 (dd, J=8.4 Hz, J=1.2 Hz, 1H), 8.26 (td, J=8.0 Hz, J=1.6 Hz, 1H), 8.09-8.04 (m, 2H), 5.06 (tr, J=7.2 Hz, 2H), 3.00 (s, 3H), 1.58 (t, J=7.2 Hz, 3H). $^{13}$C NMR (400 MHz, DMSO-$d_6$) δ 158.4, 148.2, 136.6, 135.1, 129.6, 128.9, 127.2, 122.8, 119.2, 52.5, 19.7, 15.2.

1-(3-hydroxypropyl)-4-methylquinolinium bromide (7)

A solution mixture of lepidine (0.5 g, 3.5 mmol) and 3-bromopropanol (1.9 g, 14 mmol) in acetonitrile (15 mL) was heated to reflux overnight. After cooling to room temperature, the solvent was removed. The resulting mixture was precipitate from methanol and ethyl acetate to give the desired product 7 (0.83 g) in 84% yield. $^1$H NMR (400 MHz, DMSO-$d_6$) δ 9.41 (d, J=6 Hz, 1H), 8.58 (d, J=8.8 Hz, 1H), 8.54 (dd, J=8.8 Hz, J=1.2 Hz, 1H), 8.26 (td, J=8.0 Hz, J=1.2 Hz, 1H), 8.08-8.03 (m, 2H), 5.09 (t, J=6.8 Hz, 2H), 3.52 (t, J=5.6 Hz, 2H), 3.01 (s, 3H), 2.15-2.08 (m, 2H). $^{13}$C NMR (400 MHz, DMSO-$d_6$) δ 158.5, 148.8, 136.8, 135.1, 129.5, 128.9, 127.2, 122.6, 119.3, 57.4, 54.8, 32.0, 19.7.

1-(2-hydroxyethyl)-4-methylpyridinium chloride (9)

A solution mixture of picoline (0.93 g, 10 mmol) and 2-chloroethanol (4.03 g, 50 mmol) in acetonitrile (20 mL) was heated to 120° C. in a sealed tube overnight. After cooling to room temperature, the solvent was removed under vacuum. The resulting mixture was precipitate from methanol and ethyl acetate to give the desired product 9 (1.5 g) in 87% yield. $^1$H NMR (400 MHz, DMSO-$d_6$) δ 8.94 (d, J=6.4 Hz, 2H), 7.98 (d, J=6.4 Hz, 2H), 5.55 (br, 1H), 4.64 (t, J=4.8 Hz, 2H), 3.81 (t, J=4.8 Hz, 2H), 2.60 (s, 3H). $^{13}$C NMR (400 MHz, DMSO-$d_6$) δ 158.7, 144.2, 127.9, 62.1, 60.0, 21.4.

(E)-1-(2-hydroxyethyl)-4-(2-(9-(2-(2-methoxyethoxy)ethyl)-9H-carbazol-3-yl)vinyl)pyridinium chloride (SPOH)

A solution mixture of 3a (0.13 g, 0.75 mmol), 9 (0.27 g, 0.9 mmol) and piperidine (0.1 mL) in ethanol (30 mL) was heated to reflux overnight. After cooling down to room temperature, the organic solvent was removed by rotary evaporation. The residue was purified by recrystallization from methanol affording SPOH (0.18 g) as pale red solid in 53% yield. $^1$H NMR (400 MHz, DMSO-$d_6$) δ 8.88 (d, J=6.8 Hz, 2H), 8.55 (s, 1H), 8.19 (m, 4H), 7.84 (d, J=8 Hz, 1H), 7.65 (m, 2H), 7.49 (m, 2H), 7.25 (t, J=7.2 Hz, 1H), 5.66 (s, 1H), 4.57 (m, 4H), 3.79 (m, 4H), 3.43 (m, 2H), 3.27 (m, 2H), 3.08 (s, 3H). $^{13}$C NMR (400 MHz, DMSO-$d_6$) δ 153.4, 144.4, 142.4, 141.7, 140.8, 126.4, 126.3, 126.2, 122.7, 122.6, 122.1, 121.1, 120.3, 120.0, 119.7, 110.4, 110.2, 71.2, 69.8, 68.8, 61.6, 600.1, 58.1, 42.8. HRMS (MALDI-TOF) m/z Calcd for $C_{26}H_{29}N_2O_3$ 417.2172. Found 417.2184 [M$^+$].

(E)-4-(2-(9-(2-(2-methoxyethoxy)ethyl)-9H-carbazol-3-yl)vinyl)-1-methylquinolinium iodide (SLM)

A solution mixture of 3a (0.14 g, 0.5 mmol), 4 (0.18 g, 0.6 mmol) and piperidine (0.1 mL) in ethanol (40 mL) was heated to reflux overnight. After cooling down to room temperature, the organic solvent was removed. The residue was purified by recrystallization from methanol to afford SLM (0.24 g) as red solid in 56% yield. $^1$H NMR (400 MHz, DMSO-$d_6$) δ 9.28 (d, J=6.4 Hz, 1H), 9.14 (d, J=8.4 Hz, 1H), 8.86 (s, 1H), 8.51 (d, J=6.4 Hz, 1H), 8.42 (m, 3H), 8.28 (m, 2H), 8.13 (d, J=8.8 Hz, 1H), 8.08 (t, J=7.2 Hz, 1H), 7.80 (d, J=8.8 Hz, 1H), 7.71 (d, J=8.0 Hz, 1H), 7.53 (t, J=8.0 Hz, 1H), 7.32 (t, J=7.2 Hz, 1H), 4.64 (t, J=5.2 Hz, 2H), 4.52 (s, 3H), 3.84 (t, J=5.2 Hz, 2H), 3.48 (m, 2H), 3.33 (m, 2H), 3.11 (s, 3H). $^{13}$C NMR (400 MHz, DMSO-$d_6$) δ 153.0, 147, 144.9, 142.1, 140.9, 138.8, 134.9, 129.0, 127.3, 126.7, 126.4, 126.1, 122.8, 122.2, 121.7, 120.4, 119.9, 119.3, 116.2, 115.1, 110.5, 110.4, 71.3, 69.8, 68.9, 58.1, 44.2, 42.9. HRMS (MALDI-TOF) m/z Calcd for $C_{29}H_{29}N_2O_2$ 437.2223. Found 437.2207 [M$^+$].

(E)-1-(2-hydroxyethyl)-4-(2-(9-(2-(2-methoxyethoxy)ethyl)-9H-carbazol-3-yl)vinyl)-quinolinium chloride (SLOH)

A solution mixture of 3a (0.12 g, 0.55 mmol), 5 (0.2 g, 0.66 mmol) and piperidine (0.1 mL) in ethanol (35 mL) was heated to reflux overnight. After cooling down to room temperature, the organic solvent was removed. The residue was purified by recrystallization from methanol to afford SLOH (0.17 g) as red solid in 62% yield. $^1$H NMR (400 MHz, DMSO-$d_6$) δ 9.20 (d, J=6.4 Hz, 1H), 9.15 (d, J=8.8 Hz, 1H), 8.87 (s, 1H), 8.56 (d, J=9.2 Hz, 1H), 8.52 (d, J=6.4 Hz, 1H), 8.40 (m, 2H), 8.24 (m, 2H), 8.13 (d, J=8.8 Hz, 1H), 8.05 (t, J=7.6 Hz, 1H), 7.78 (d, J=8.8 Hz, 1H), 7.71 (d, J=8.4 Hz, 1H), 7.52 (t, J=8.0 Hz, 1H), 7.31 (t, J=7.6 Hz, 1H), 5.27 (t, J=5.6 Hz, 1H), 5.05 (t, J=4.8 Hz, 2H), 4.64 (t, J=4.8 Hz, 2H), 3.94 (m, 2H), 3.84 (t, J=5.2 Hz, 2H), 3.47 (m, 2H), 3.31 (m, 2H), 3.11 (s, 3H). $^{13}$C NMR (400 MHz, DMSO-$d_6$) δ 153.3, 147.8, 145.0, 142.1, 140.9, 138.1, 134.7, 128.7, 127.1, 126.8, 126.7, 126.5, 122.8, 122.2, 121.7, 120.3, 119.8, 119.2, 116.3, 114.8, 110.4, 110.3, 71.2, 69.8, 68.8, 58.9, 58.5, 58.0, 42.9. HRMS (MALDI-TOF) m/z Calcd for $C_{30}H_{31}N_2O_3$ 467.2342. Found 467.2340 [M$^+$]. Calcd for $C_{30}H_{31}ClN_2O_3$: C, 71.53; H, 6.21; N, 5.57. Found: C, 71.04; H, 6.23; N, 5.36.

(E)-1-ethyl-4-(2-(9-(2-(2-methoxyethoxy)ethyl)-9H-carbazol-3-yl)vinyl)quinolinium bromide (SLE)

A solution mixture of 6 (0.20 g, 0.8 mmol), 3a (0.33 g, 1.1 mmol) and piperidine (0.1 mL) in ethanol (40 mL) was heated to reflux overnight. After cooling down to room temperature, the organic solvent was removed. The residue was purified by precipitation from methanol and ethyl acetate to afford SLE (0.22 g) in 53% yield. $^1$H NMR (400 MHz, DMSO-$d_6$) δ 9.34 (d, J=8.4 Hz, 1H), 9.15 (d, J=8.4 Hz, 1H), 8.86 (s, 1H), 8.54-8.51 (m, 2H), 8.44 (d, J=16 Hz, 1H), 8.36 (d, J=16 Hz, 1H), 8.28-8.23 (m, 2H), 8.12 (d, J=8.0 Hz, 1H), 8.05 (t, J=7.6 Hz, 1H), 7.77 (d, J=8.4 Hz, 1H), 7.70 (d, J=8.4 Hz, 1H), 7.52 (t, J=7.6 Hz, 1H), 7.31 (t, J=7.6 Hz, 1H), 4.99 (tr, J=6.8 Hz, 2H), 4.63 (t, J=4.8 Hz, 2H), 3.84 (t, J=4.8 Hz, 2H), 3.48 (t, J=4.8 Hz, 2H), 3.31 (t, J=4.8 Hz, 2H), 3.11 (s, 3H), 1.59 (t, J=6.8 Hz, 3H). $^{13}$C NMR (400 MHz, DMSO-d$_6$) δ 153.2, 146.7, 145.1, 142.2, 140.9, 137.7, 135.0, 128.9, 127.4, 126.8, 126.7, 126.5, 126.4, 122.8, 122.2, 121.8, 120.4, 119.9, 119.0, 116.2, 115.5, 110.4, 110.3, 71.3, 69.8, 68.9, 58.1, 51.9, 15.1. HRMS (MALDI-TOF) m/z Calcd for C$_{30}$H$_{31}$N$_2$O$_2$ 451.2380. Found 451.2362 [M]$^+$.

(E)-1-(3-hydroxypropyl)-4-(2-(9-(2-(2-methoxy-ethoxy)ethyl)-9H-carbazol-3-yl)vinyl)-quinolinium bromide (SLOH-Pr)

A solution mixture of 7 (0.17 g, 0.6 mmol), 3a (0.24 g, 0.8 mmol) and piperidine (0.1 mL) in ethanol (40 mL) was heated to reflux overnight. After cooling down to room temperature, the organic solvent was removed. The residue was purified by precipitation from methanol and ethyl acetate to afford SLOH-Pr (0.14 g) in 41% yield. $^1$H NMR (400 MHz, DMSO-d$_6$) δ 9.29 (d, J=6.8 Hz, 1H), 9.15 (d, J=8.4 Hz, 1H), 8.88 (s, 1H), 8.51 (d, J=6.8 Hz, 1H), 8.45 (d, J=16 Hz, 1H), 8.37 (d, J=16 Hz, 1H), 8.28-8.24 (m, 2H), 8.13 (d, J=8.4 Hz, 1H), 8.05 (t, J=8.0 Hz, 1H), 7.77 (d, J=8.8 Hz, 1H), 7.70 (d, J=8.4 Hz, 1H), 7.52 (t, J=7.6 Hz, 1H), 7.31 (t, J=7.2 Hz, 1H), 5.01 (t, J=7.2 Hz, 2H), 4.86 (t, J=5.2 Hz, 1H), 4.63 (t, J=4.8 Hz, 2H), 3.84 (t, J=5.2 Hz, 2H), 3.55 (tr, J=5.2 Hz, 2H), 3.47 (t, J=5.6 Hz, 2H), 3.31 (t, J=4.8 Hz, 2H), 3.11 (s, 3H), 2.13 (t, J=6.0 Hz, 2H). $^{13}$C NMR (400 MHz, DMSO-d$_6$) δ 153.3, 147.3, 145.1, 142.2, 140.9, 137.9, 135.0, 128.8, 127.4, 126.8, 126.7, 126.5, 126.4, 122.8, 122.2, 121.8, 120.4, 119.9, 119.0, 116.3, 115.2, 110.5, 110.4, 71.3, 69.8, 68.9, 58.1, 57.6, 54.2, 42.9, 32.0. HRMS (MALDI-TOF) m/z Calcd for C$_{31}$H$_{33}$N$_2$O$_3$ 481.2485. Found 481.2458 [M]$^+$.

(E)-1-methyl-4-(2-(9-methyl-9H-carbazol-3-yl)vinyl)quinolinium iodide (Me-SLM)

A solution mixture of 1,4-dimethylquinolinium iodide (0.14 g, 0.5 mmol), 3b (0.13 g, 0.6 mmol) and piperidine (0.1 mL) in ethanol (40 mL) was heated to reflux overnight. After cooling down to room temperature, the organic solvent was removed. The residue was purified by precipitation from methanol and ethyl acetate to afford Me-SLM (0.14 g) in 62% yield. $^1$H NMR (400 MHz, DMSO-d$_6$) δ 9.27 (d, J=6.4 Hz, 1H), 9.12 (d, J=8.4 Hz, 1H), 8.86 (s, 1H), 8.49 (d, J=6.4 Hz, 1H), 8.45-8.23 (m, 5H), 8.15 (d, J=8.8 Hz, 1H), 8.06 (t, J=7.6 Hz, 1H), 7.75 (d, J=8.4 Hz, 1H), 7.66 (d, J=8.0 Hz, 1H), 7.55 (t, J=7.6 Hz, 1H), 7.32 (t, J=7.6 Hz, 1H), 4.51 (s, 3H), 3.95 (s, 3H). $^{13}$C NMR (400 MHz, DMSO-d$_6$) δ 152.9, 147.3, 144.8, 142.2, 141.2, 138.7, 134.8, 128.8, 127.4, 126.6, 126.4, 126.3, 126.0, 122.6, 122.0, 121.8, 120.4, 119.7, 119.1, 116.0, 115.0, 109.8, 109.7, 44.3, 29.3. HRMS (MALDI-TOF) m/z Calcd for C$_{25}$H$_{21}$N$_2$ 349.1699. Found 349.1694 [M]$^+$.

9-(bromomethyl)acridine (10)

To a solution of 9-methylacridine (1.93 g, 10 mmol) in dichloromethane (100 mL) was added NBS (1.78 g, 10 mmol) portion-wise in an ice-water bath. After complete addition, the solution mixture was warmed to room temperature and stirred overnight. The resulting solution was washed with water and brine. The organic phase was dried over anhydrous sodium sulfate and the solvent was removed. The residue was purified by silica gel chromatography using ethyl acetate and petroleum ether (EA:PE=1:5) as eluent to afford 10 (2.08 g) in 77% yield. $^1$H NMR (400 MHz, CDCl$_3$) δ 8.27 (d, J=8.8 Hz, 4H), 7.81 (t, J=8.0 Hz, 2H), 7.68 (t, J=8.0 Hz, 2H), 5.42 (s, 2H). $^{13}$C NMR (400 MHz, CDCl$_3$) δ 148.9, 138.7, 130.5, 130.1, 126.8, 123.8, 123.4, 23.1. MS (FAB) m/z Calcd for C$_{14}$H$_{10}$BrN 272.1. Found 2722. [M]$^+$.

Diethyl acridin-9-ylmethylphosphonate (11)

The mixture of 10 (1.5 g, 5.5 mmol) and triethyl phosphite (2 mL) was heated to reflux for 4 h. After cooling down to room temperature, the excess triethyl phosphite was removed under vacuum to afford 11 (1.7 g) in 94% yield. $^1$H NMR (400 MHz, CDCl$_3$) δ 8.23 (d, J=8.8 Hz, 2H), 8.17 (d, J=8.8 Hz, 2H), 7.72 (t, J=7.2 Hz, 2H), 7.54 (t, J=7.2 Hz, 2H), 4.13 (d, J=24 Hz, 2H), 3.92-3.77 (m, 4H), 1.04 (t, J=7.2 Hz, 6H). $^{13}$C NMR (400 MHz, CDCl$_3$) δ 148.4, 148.3, 135.8, 135.7, 129.9, 129.8, 125.8, 125.3, 125.2, 124.9, 124.8, 62.4, 27.5, 26.1, 16.1.

(E)-9-(2-(9-(2-(2-methoxyethoxy)ethyl)-9H-carbazol-3-yl)vinyl)acridine (12)

To a solution of 3a (0.45 g, 1.5 mmol) and 11 (0.49 g, 1.5 mmol) in dry THF (45 mL), NaH (45 mg, 1.8 mmol) was added carefully in an ice-water bath. After complete addition, the solution mixture was warmed to room temperature and stirred overnight. After quenching by water, the resulting mixture was extracted with ethyl acetate for three times. The combined organic phase was washed with brine twice and dried over anhydrous sodium sulfate. After removing the solvent, the resulting crude product was purified by silica gel chromatography using DCM and petroleum ether (DCM:PE=1:10) to afford 12 (0.45 g) in 64% yield. $^1$H NMR (400 MHz, CDCl$_3$) δ 8.45 (d, J=8.8 Hz, 2H), 8.37 (s, 1H), 8.26 (d, J=8.8 Hz, 2H), 8.15 (d, J=8.0 Hz, 1H), 7.95 (d, J=8.4 Hz, 1H), 7.85 (d, J=8.8 Hz, 1H), 7.80 (t, J=8.0 Hz, 2H), 7.58-7.51 (m, 5H), 7.31-7.25 (m, 2H), 4.58 (t, J=6.4 Hz, 2H), 3.92 (t, J=6.4 Hz, 2H), 3.57-3.55 (m, 2H), 3.48-3.45 (m, 2H), 3.35 (s, 3H). $^{13}$C NMR (400 MHz, CDCl$_3$) δ 148.9, 143.8, 141.0, 140.6, 129.9, 127.9, 126.1, 125.4, 124.6, 123.4, 122.9, 120.4, 119.5, 119.2, 119.1, 109.4, 109.2, 71.9, 70.9, 69.3, 59.1, 43.3. HRMS (MALDI-TOF) m/z Calcd for C$_{32}$H$_{29}$N$_2$O$_2$ 473.2223. Found 473.2210 [M+H]$^+$.

(E)-9-(2-(9-(2-(2-methoxyethoxy)ethyl)-9H-carbazol-3-yl)vinyl)-10-methylacridinium iodide (SAM)

A solution of 12 (0.20 g, 0.4 mmol) and methyl iodide (0.57 g, 4 mmol) in acetonitrile (8 mL) was heated to 100° C. in sealed tube for 24 h. After cooling down to room temperature, the solvent was removed and the resulting mixture was purified by precipitation from methanol and ethyl acetate to afford SAM (0.15 g) in 61% yield. $^1$H NMR (400 MHz, CDCl$_3$) δ 8.74 (d, J=8.0 Hz, 2H), 8.49 (s, 1H), 8.46 (d, J=8.8 Hz, 2H), 8.31 (d, J=16 Hz, 1H), 8.26 (t, J=8.0 Hz, 2H), 8.10 (d, J=8.0 Hz, 1H), 7.93 (d, J=8.0 Hz, 1H), 7.83 (t, J=7.2 Hz, 2H), 7.51 (d, J=8.4 Hz, 1H), 7.46 (t, J=6.4 Hz, 2H), 7.44 (d, J=16 Hz, 1H), 7.20 (t, J=6.4 Hz, 1H), 4.82 (s, 3H), 4.46 (t, J=6.0 Hz, 2H), 3.88 (t, J=6.0 Hz, 2H), 3.55-3.53 (m, 2H), 3.44-3.42 (m, 2H), 3.30 (s, 3H). $^{13}$C NMR (400 MHz, CDCl$_3$) δ 157.9, 149.5, 141.8, 140.5, 140.1, 137.8, 129.3, 127.4, 126.9, 126.5, 126.2, 123.9, 123.2, 122.1, 121.2, 121.1, 119.9, 117.9, 117.4, 109.4, 109.0, 71.7, 70.6, 69.0, 58.9, 43.3, 39.5. HRMS (MALDI-TOF) m/z Calcd for C$_{33}$H$_{31}$N$_2$O$_2$$^+$ 487.2380. Found 487.2387 [M]$^+$.

(E)-10-(2-hydroxyethyl)-9-(2-(9-(2-(2-methoxy-ethoxy)ethyl)-9H-carbazol-3-yl)vinyl)-acridinium iodide (SAOH)

A solution of 12 (0.2 g, 0.4 mmol) and 2-iodoethanol (0.7 g, 4 mmol) in acetonitrile (10 mL) was heated to 120° C. in sealed tube for 24 h. After cooling down to room temperature, the solvent was removed and the resulting mixture was purified by precipitation from methanol and ethyl acetate to afford SAOH (0.13 g) in 52% yield. $^1$H NMR (400 MHz, CDCl$_3$) δ 8.98 (d, J=9.2 Hz, 2H), 8.77 (d, J=8.4 Hz, 2H), 8.44 (s, 1H), 8.36 (t, J=8.0 Hz, 2H), 8.18 (d, J=8.4 Hz, 1H), 8.17 (d, J=16 Hz, 1H), 7.91 (d, J=8.0 Hz, 1H), 7.86 (t, J=8.0 Hz, 2H), 7.62 (d, J=8.8 Hz, 1H), 7.55 (d, J=8.4 Hz, 1H), 7.52 (t, J=6.4 Hz, 2H), 7.48 (d, J=16 Hz, 1H), 7.33 (t, J=6.4 Hz, 1H), 5.63 (t, J=6.0 Hz, 2H), 4.75 (t, J=7.6 Hz, 1H), 4.59 (t, J=6.0 Hz, 2H), 4.51-4.47 (m, 2H), 3.94 (t, J=6.0 Hz, 2H), 3.57-3.55 (m, 2H), 3.47-3.44 (m, 2H), 3.33 (s, 3H). $^{13}$C NMR (400 MHz, CDCl$_3$) δ 158.2, 149.1, 141.9, 140.7, 140.6, 138.1, 129.1, 126.9, 126.5, 126.4, 124.3, 123.3, 122.4, 121.2, 120.9, 120.0, 119.0, 117.0, 109.6, 109.2, 71.8, 70.6, 69.1, 59.3, 58.9, 52.2, 43.3. HRMS (MALDI-TOF) m/z Calcd for $C_{34}H_{33}N_2O_3^+$ 517.2486. Found 517.2476 [M]$^+$.

Another general chemical structures of carbazole-based fluorophores representation, including S series are shown in FIG. 14.

In FIG. 14, Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;

R$_1$ is a radical selected from the group consisting of polyethylene glycol chain, alkyl, substituted alkyl, peptide chain, glycosidyl, and C(O)NHCH((CH$_2$CH$_2$O)$_2$CH$_3$)$_2$;

R$_2$ is selected from the group consisting of ethenyl, ethynyl, azo and azomethinyl.

R$_3$ is a radical selected from the group consisting of HO-alkyl, alkyl-COOalkyl, alkyl-CONH$_2$, alkyl-CON-Halkyl, polyethylene glycol chain;

X is an anion selected from the group consisting of F, Cl, Br, I, HSO$_4$, H$_2$PO$_4$, HCO$_3$, tosylate, and mesylate;

Y is selected from the group consisting of H, F, Cl, OH, and OCH$_3$.

Figure 15:
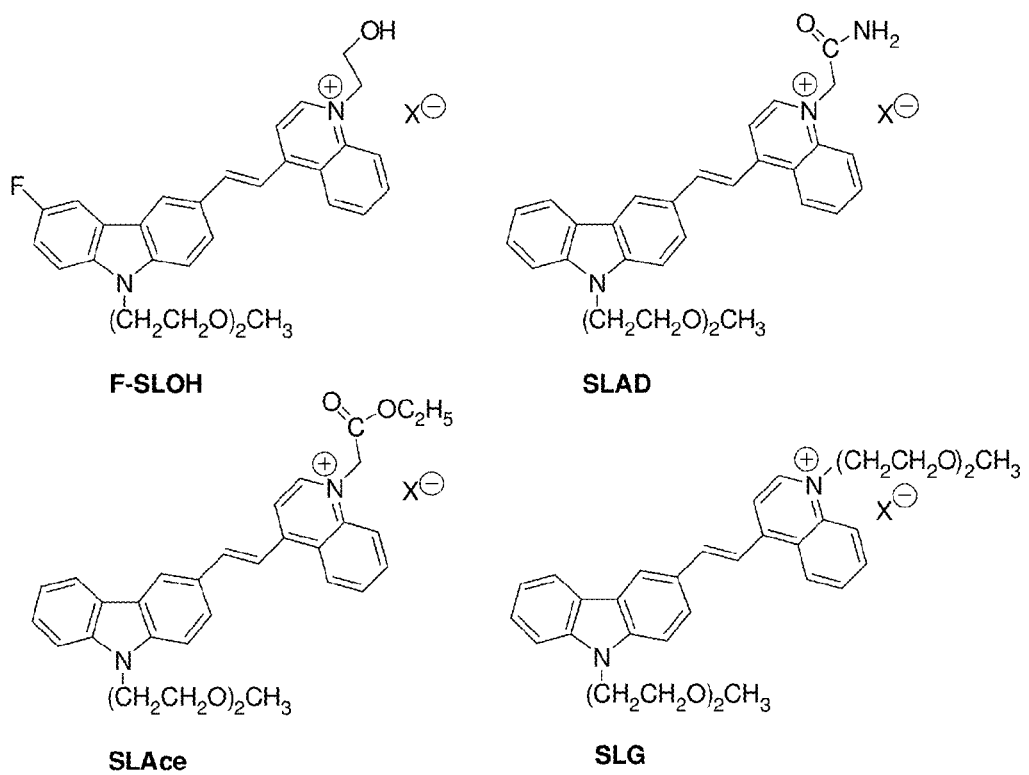
FIG. 15 shows the formula "F-SLOH", "SLAD", "SLAce", and "SLG", respectively.
Figures 16, 16C:
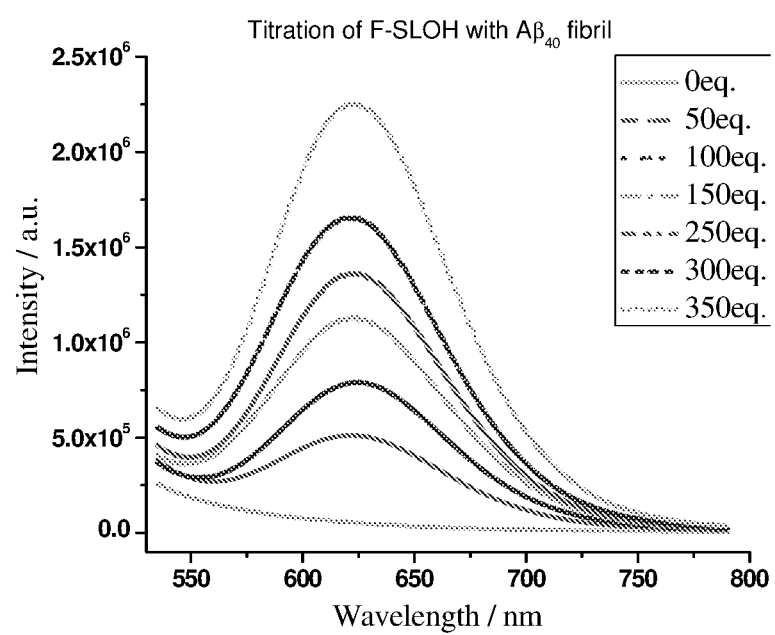
FIG. 16 shows the fluorescence spectra of F-SLOH (FIG. 16A-C), SLAD (FIG. 16D-F), SLAce (FIG. 16G-I), and SLG (FIG. 16J-L) in phosphate buffer (1 µM) upon addition of various concentrations of Aβ(1-42) monomer, Aβ(1-40) monomer and Aβ(1-40) fibril, respectively.
Figures 16, 16F:
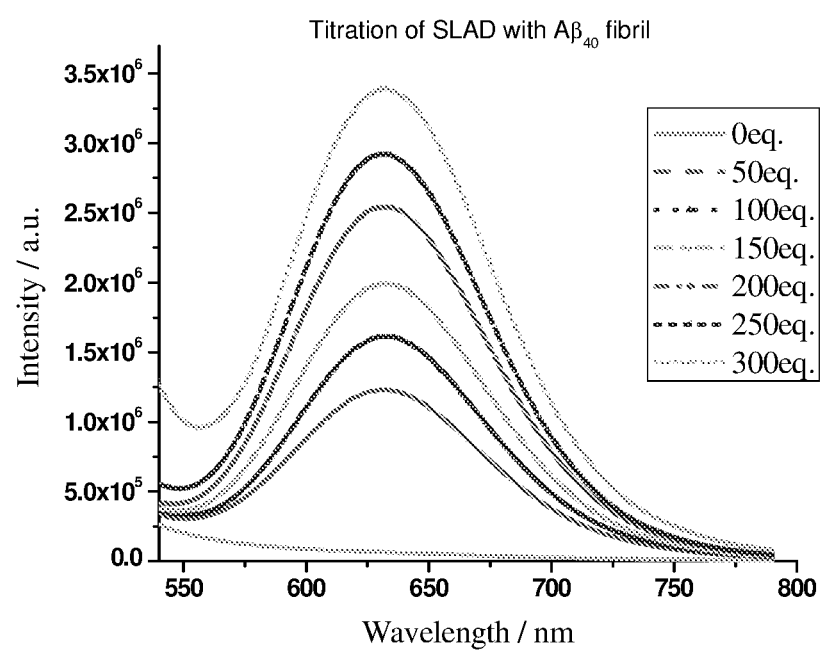
Figures 16, 16I:
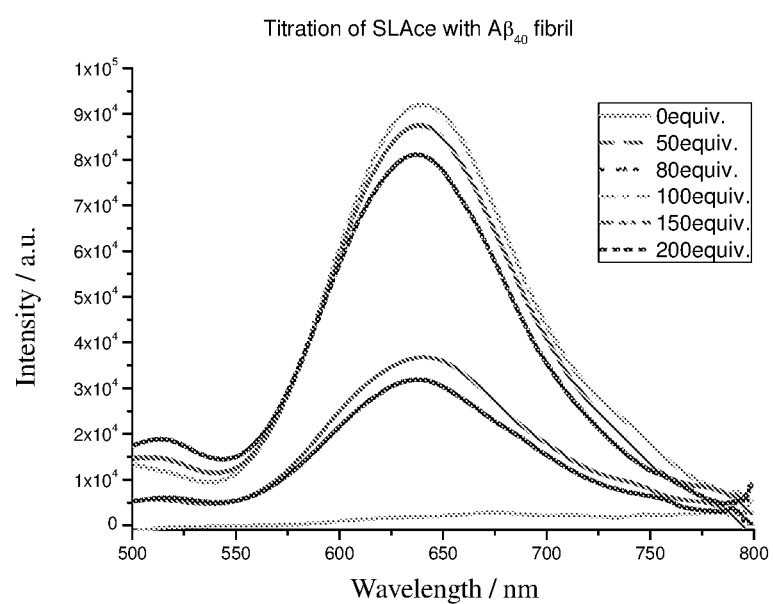
Figures 16, 16L:
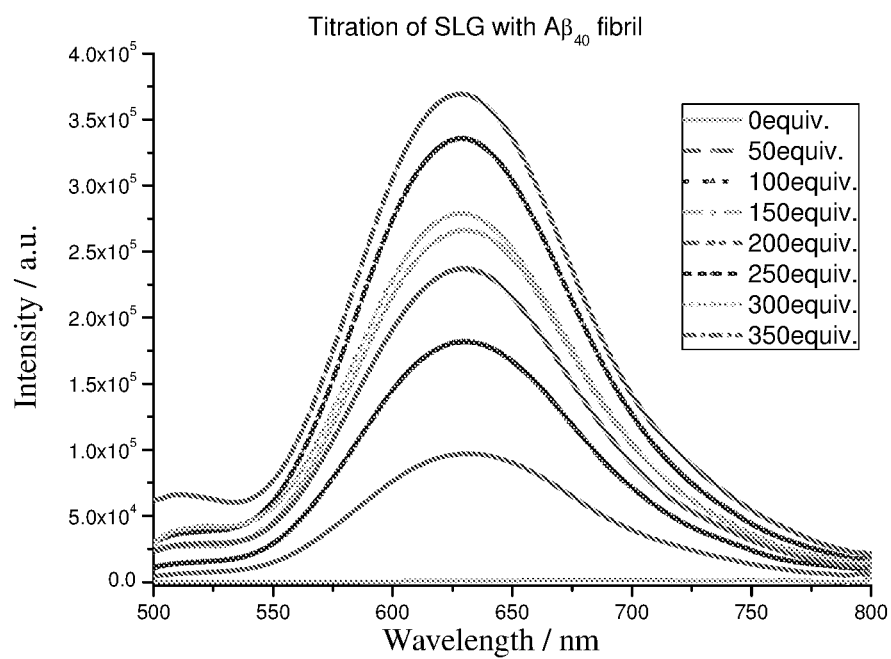

A novel series of water-soluble carbazole-based fluorophores has been designed and developed. These molecules were found to bind to Aβ(1-40) and Aβ(1-42) peptides and, more importantly, their oligomers, and fibrils with strong fluorescence enhancement, therefore allowing direct imaging and detection for the Aβ peptides, oligomers and their fibrils. (FIG. 16) Upon binding with Aβ peptides, there is an increase in fluorescence intensity up to 160-fold enhancement concomitant with the substantial blue shifts in the emission spectra of the fluorophores. Remarkably, these molecules, including F-SLOH, SLAD, SLAce, and SLG were found to inhibit Aβ peptide aggregation and prevent fibril growth. In one embodiment of the present invention, Ar is a quinolinyl or substituted quinolinyl; R$_1$ is a 2-(2-methoxyethoxy)ethoxy; R$_2$ is an ethenyl; R$_3$ is a 2-hydroxyethyl or acetamide or acetate or 2-(2-methoxyethoxy)ethoxy; X is a chloride or iodide and Y is a H or F which are represented by the formula "F-SLOH", "SLAD", "SLAce", and "SLG", respectively, as shown in FIG. 15.

Figure 17:
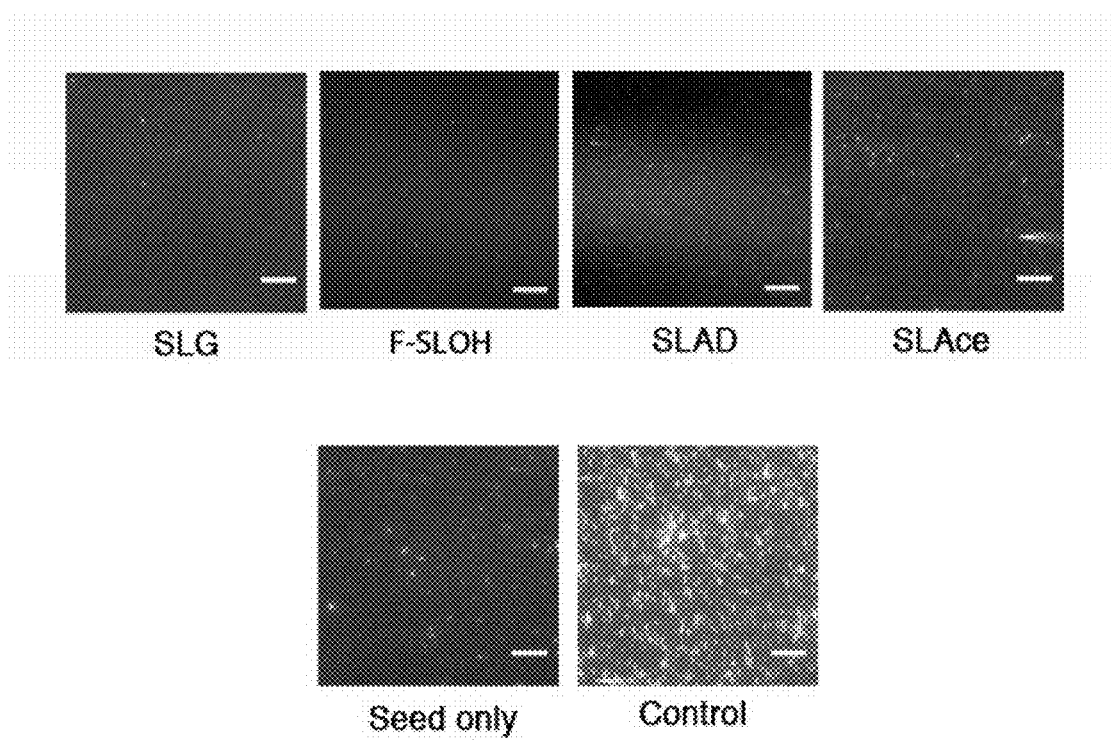
FIG. 17 shows the TIRFM images of Aβ monomer and seeds after incubation with the carbazole-based fluorophores, SLG, F-SLOH, SLAD and SLAce. The panels below show the images of seed only and Aβ fibril formation without the carbazole-based fluorophore for comparison. These images were obtained by an addition of ThT dye excited at 445 nm.

Total Internal Reflection Fluorescence Microscope (TIRFM) technique developed was used to investigate the inhibition effects of these functional fluorophores on Aβ (1-40) fibril formation (FIG. 17). Remarkably, some of these molecules, e.g., F-SLOH, SLAD, SLAce, and SLG were found to inhibit Aβ (1-40) peptide aggregation and prevent fibril growth (FIG. 17).

Figures 18, 18A:
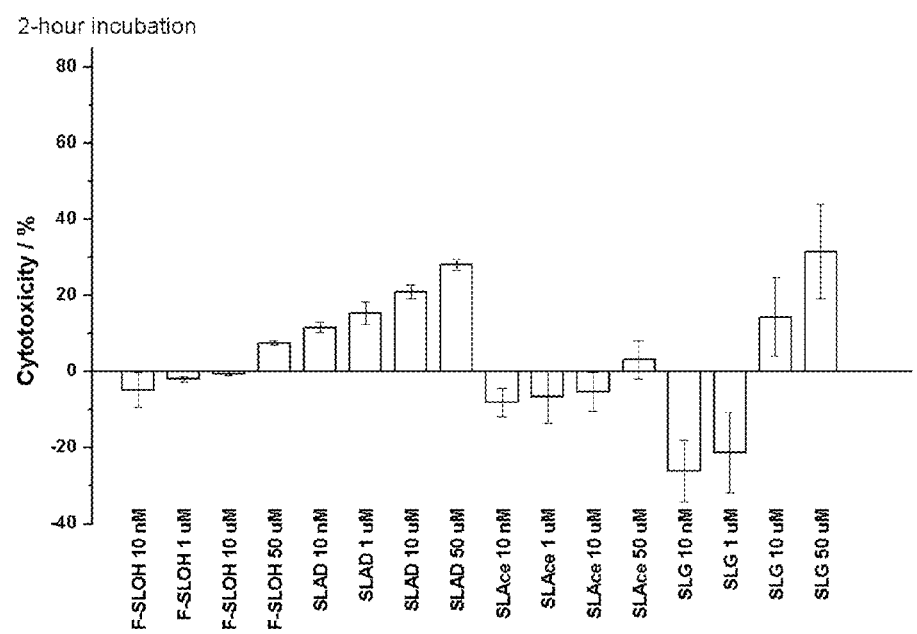
FIG. 18 shows the cytotoxicities of the carbazole-based cyanines, F-SLOH, SLAD, SLAce and SLG towards the SH-SY5Y neuronal cell with MTT assays at 2-hour (FIG. 18A), 6-hour (FIG. 18B) and 24-hour incubation (FIG. 18C).
Figures 21, 21A:
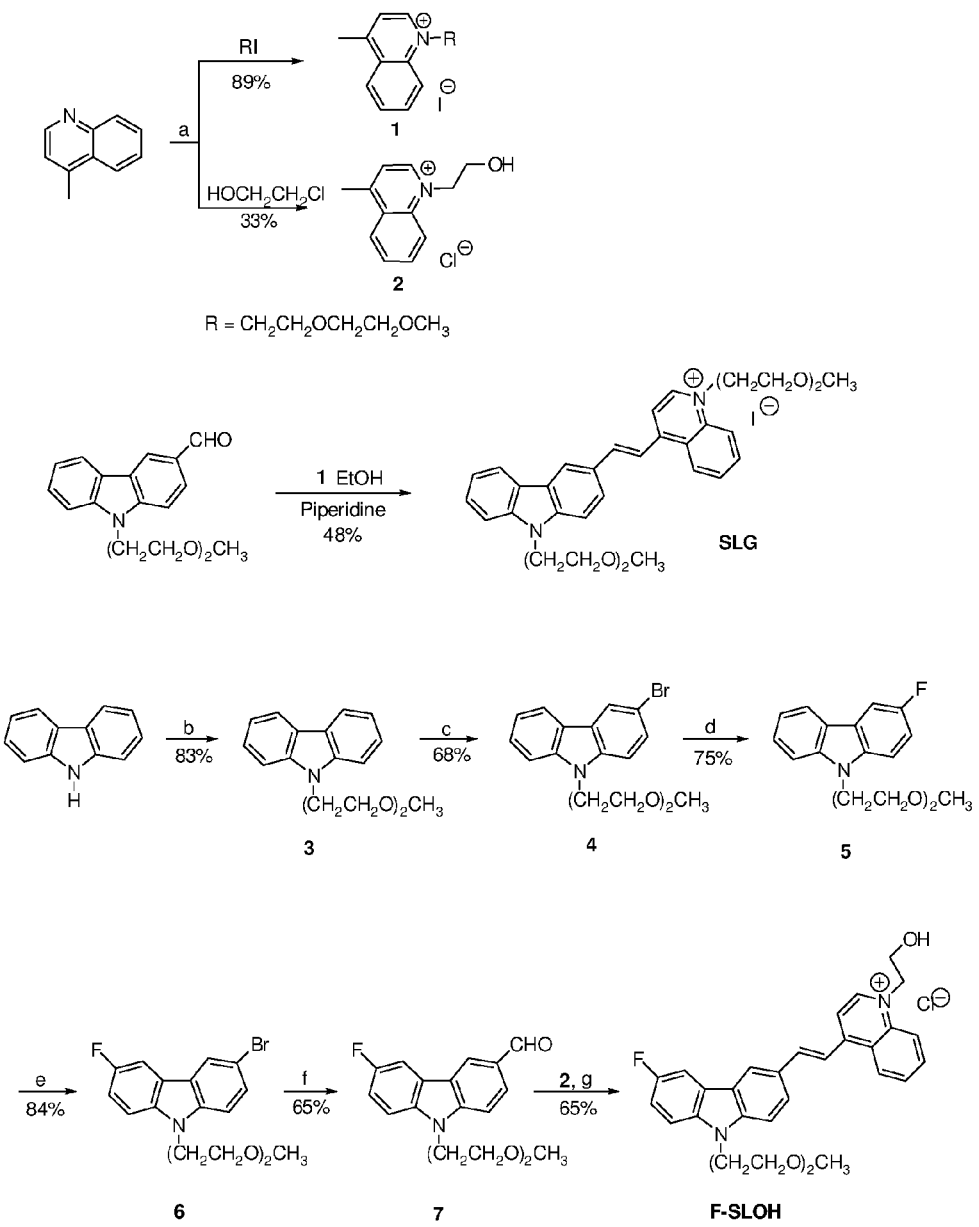
FIG. 21 shows the synthesis of carbazole-based fluorophores, F-SLOH and SLG (FIG. 21A), SLAD and SLAce (FIG. 21B). (Note: Reagents and Conditions: a, MeCN, reflux; b, ClCH$_2$CH$_2$OCH$_2$CH$_2$OCH$_3$, NaH, DMF, 75° C.; c, NBS, chloroform, 0° C. to r.t.; d, n-BuLi, NFSi, THF, −78° C. to r.t.; e, NBS, chloroform, 0° C. to r.t.; f, n-BuLi, DMF, THF, −78° C. to r.t.; g, MeOH, reflux; h, TMSCl, DMF, 100° C., sealed tube; i, CH$_3$CH$_2$OCOCH$_2$Br, ethanol, r.t.; j, NH$_2$COCH$_2$Br, MeCN, reflux.)
Figures 21, 21B:
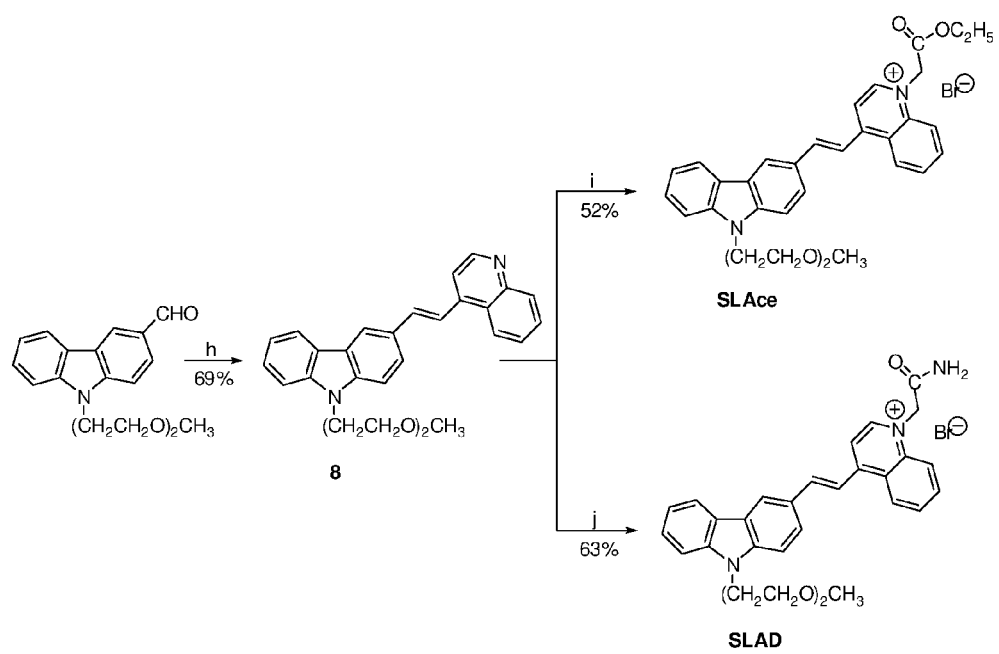

To confirm its clinical application, the cytotoxicities of these carbazole-based molecules towards the neuronal cell, i.e., SH-SY5Y cell line, are investigated by MTT [3-(4,5-dimethylthiazol-2-yl)-2,5-diphenyltetrazolium bromide] reduction assay. The results obtained (FIG. 18) show that these molecules are essentially non-toxic (20%) to the neuronal cell. The cytotoxicity of these molecules are low with $LC_{50}$=5-90 µM.

There is growing evidence showing that the soluble Aβ oligomers is the most neurotoxic form, further experiments with these carbazole-based molecules conducted in the presence of the Aβ monomer, Aβ oligomers and fibrils show that the primary cortical cells are protected from the neurotoxic effects of the Aβ species when incubated with the cyanine dyes, F-SLOH, and SLAD (FIG. 19). The reactive oxygen species (ROS) induced by the Aβ toxicity causes much damage in AD. Remarkably, F-SLOH, and SLAD reduce the ROS induced by the Aβ species in primary cortical cells.

However, in order for the observed neuroprotective effect to be clinically useful, these molecules need to be able to pass through the blood-brain barrier. The ability of these molecules to penetrate the blood-brain barrier was demonstrated in mice (FIG. 20). The binding of these molecules toward Aβ plaques in the brains of the Alzheimer's disease animal models are also demonstrated. Impressively, F-SLOH, SLAD, SLAce, and SLG show blood-brain permeability.

Further Synthesis Experiments (E)-1-(2-(2-methoxyethoxy)ethyl)-4-(2-(9-(2-(2-methoxyethoxy)ethyl)-9H-carbazol-3-yl)vinyl) quinolinium iodide (SLG)

A solution mixture of 1 (0.30 g, 0.8 mmol), 9-(2-(2-methoxyethoxy)ethyl)-9H-carbazole-3-carbaldehyde (0.33 g, 1.1 mmol) and piperidine (0.1 mL) in ethanol (40 mL) was heated to reflux overnight. After cooling down to room temperature, the organic solvent was removed. The residue was purified by precipitation from methanol and ethyl acetate to afford SLG (0.25 g) in 48% yield. $^1$H NMR (400 MHz, DMSO-d$_6$) δ 9.18 (d, J=6.8 Hz, 1H), 9.14 (d, J=8.0 Hz, 1H), 8.87 (s, 1H), 8.55 (d, J=8.8 Hz, 1H), 8.51 (d, J=6.8 Hz, 1H), 8.45 (d, J=16 Hz, 1H), 8.36 (d, J=16 Hz, 1H), 8.24 (d, J=7.2 Hz, 2H), 8.13 (d, J=7.6 Hz, 1H), 8.05 (t, J=7.6 Hz, 1H), 7.77 (d, J=8.4 Hz, 1H), 7.69 (d, J=8.0 Hz, 1H), 7.52 (t, J=7.2 Hz, 1H), 7.31 (t, J=7.2 Hz, 1H), 5.15 (t, J=5.2 Hz, 2H), 4.63 (t, J=4.8 Hz, 2H), 3.97 (t, J=5.2 Hz, 2H), 3.84 (t, J=4.8 Hz, 2H), 3.53 (t, J=4.8 Hz, 2H), 3.48 (t, J=4.8 Hz, 2H), 3.32-3.29 (m, 4H), 3.11 (s, 3H), 3.06 (s, 3H). $^{13}$C NMR (100 MHz, DMSO-d$_6$) δ 153.5, 147.7, 145.3, 142.2, 140.9, 138.1, 134.8, 128.8, 127.4, 126.7, 126.4, 122.8, 122.2, 121.8, 120.4, 119.8, 119.2, 116.2, 114.8, 110.4, 110.3, 71.2, 71.1, 69.8, 69.6, 68.8, 67.8, 58.1, 58.0, 55.9, 42.9. HRMS (MALDI-TOF) m/z Calcd for $C_{33}H_{37}N_2O_4$ 525.2747. Found 525.2747 [M]$^+$.

3-Fluoro-9-(2-(2-methoxyethoxy)ethyl)-9H-carbazole (5)

To a solution of 3-bromo-9-(2-(2-methoxyethoxy)ethyl)-9H-carbazole (3.23 g, 9.3 mmol) in dry THF (50 ml) was added n-BuLi (1.6 M, 8.7 ml, 13.9 mmol) at −78° C. The resulting mixture was stirred for 50 min at −78° C. and then added with N-fluorobenzenesulfonimide (5.6 g, 18.6 mmol). The reaction mixture was allowed to warm to rt and stirred for 2 h before quenched with ammonia chloride solution. The organic layer was separated, dried over anhydrous sodium sulfate and evaporated under vacuum. The residue was purified by silica gel column chromatography eluting with 3:1 petroleum ether/ethyl acetate to give compound 5 in 75% yield. $^1$H NMR (400 MHz, CDCl$_3$) δ 8.03 (d, J=7.6 Hz, 1H), 7.73 (dd, J=2.4 Hz, J=8.8 Hz 1H), 7.50-7.44 (m, 2H), 7.39 (dd, J=4.4 Hz, J=8.8 Hz, 1H), 7.25-7.17 (m, 2H), 4.49 (t, J=6.4 Hz, 2H), 3.86 (t, J=6.4 Hz, 2H), 3.52-3.50 (m, 2H), 3.43-3.41 (m, 2H), 3.32 (s, 3H). $^{13}$C NMR (100 MHz, CDCl$_3$) δ 158.6, 156.2, 141.4, 137.1, 126.3, 123.4, 123.3, 122.6, 122.6, 120.6, 119.1, 113.6, 113.3, 109.7, 109.6, 109.2, 106.1, 105.9, 72.1, 71.0, 69.4, 59.2, 43.4. HRMS (MALDI-TOF) m/z Calcd for C$_{17}$H$_{18}$FNO$_2$ 287.1316. Found 287.1314[M]$^+$.

3-Bromo-6-fluoro-9-(2-(2-methoxyethoxy)ethyl)-9H-carbazole (6)

To a solution of 3-fluoro-9-(2-(2-methoxyethoxy)ethyl)-9H-carbazole (1.06 g, 3.71 mmol) in chloroform (20 ml) was added NBS (0.66 g, 3.71 mmol) batch-wise in an ice-water bath. After complete addition, the reaction mixture was allowed to warm to room temperature slowly and stirred overnight. The reaction mixture was washed with water and brine. The organic layer was dried over anhydrous sodium sulfate and evaporated under reduced pressure to give compound 6 in 84% yield. $^1$H NMR (400 MHz, CDCl$_3$) δ 8.09-8.06 (m, 1H), 7.63-7.60 (m, 1H), 7.52-7.50 (m, 1H), 7.36-7.26 (m, 2H), 7.21-7.16 (m, 1H), 4.40 (d, J=5.6 Hz, 2H), 3.82-3.80 (m, 2H), 3.49-3.46 (m, 2H), 3.40-3.38 (m, 2H), 3.29 (s, 3H). $^{13}$C NMR (100 MHz, CDCl$_3$) δ 158.7, 156.3, 140.1, 137.4, 128.9, 124.2, 124.2, 123.2, 122.3, 122.2, 114.4, 114.1, 111.8, 110.8, 110.0, 109.9, 106.2, 106.0. HRMS (MALDI-TOF) m/z Calcd for C$_{17}$H$_{17}$BrFNO$_2$ 366.0499. Found 366.0502[M]$^+$.

6-Bromo-9-(2-(2-methoxyethoxy)ethyl)-9H-carbazole-3-carbaldehyde (7)

To a solution of 3-bromo-6-fluoro-9-(2-(2-methoxyethoxy)ethyl)-9H-carbazole (3.4 g, 9.3 mmol) in dry THF (50 ml) was added n-BuLi (1.6 M, 8.7 ml, 13.9 mmol) at −78° C. The resulting mixture was stirred for 50 min at −78° C. and then added with N-formylmorpholine (1.86 ml, 18.6 mmol). The reaction mixture was allowed to warm to rt and stirred for 2 h before quenched with ammonia chloride solution. The organic layer was separated, dried over anhydrous sodium sulfate and evaporated under vacuum. The residue was purified by silica gel column chromatography eluting with 2:1 petroleum ether/ethyl acetate to give compound 7 in 65% yield. $^1$H NMR (400 MHz, CDCl$_3$) δ 10.08 (s, 1H), 8.53 (s, 1H), 8.02-8.00 (m, 1H), 7.80-7.77 (m, 1H), 7.54 (d, J=8.8 Hz, 1H), 7.45 (dd, J=4.0 Hz, J=9.2 Hz 1H), 7.28-7.23 (m, 1H), 4.52 (t, J=5.6 Hz, 2H), 3.88 (t, J=5.6 Hz, 2H), 3.52-3.50 (m, 2H), 3.40 (d, J=2.8 Hz, 2H), 3.28 (s, 3H). $^{13}$C NMR (100 MHz, CDCl$_3$) δ 191.8, 159.3, 156.9, 145.2, 137.8, 128.8, 127.5, 124.4, 123.7, 123.7, 123.7, 122.8, 114.8, 114.5, 110.6, 110.5, 109.8, 106.7, 106.4, 72.1, 71.0, 69.5, 59.2, 43.9. HRMS (MALDI-TOF) m/z Calcd for C$_{18}$H$_{18}$FNO$_3$ 316.1343. Found 316.1340[M]+.

(E)-4-(2-(6-Fluoro-9-(2-(2-methoxyethoxy)ethyl)-9H-carbazol-3-yl)vinyl)-1-(2-hydroxyethyl)quinolin-1-ium chloride (F-SLOH)

A solution mixture of 2 (0.21 g, 1.2 mmol), 6-bromo-9-(2-(2-methoxyethoxy)ethyl)-9H-carbazole-3-carbaldehyde (0.50 g, 1.6 mmol) and piperidine (0.1 ml) in methanol (40 ml) was heated to reflux overnight. After being cooled down to room temperature, the organic solvent was removed. The residue was purified by precipitation from methanol and ethyl acetate to afford F-SLOH in 65% yield. $^1$H NMR (400 MHz, DMSO-d$_6$) δ 9.22 (d, J=6.8 Hz, 1H), 9.15 (d, J=8.4 Hz, 1H), 8.91 (s, 1H), 8.58 (d, J=9.2 Hz, 1H), 8.53 (d, J=6.8 Hz, 1H), 8.40 (d, J=3.6 Hz, 1H), 8.24 (t, J=7.6 Hz 1H), 8.15-8.13 (m, 1H), 8.08-8.03 (m, 2H), 7.78 (d, J=8.8 Hz, 1H), 7.74-7.71 (m, 1H), 7.40-7.35 (m, 1H), 5.34 (s, 1H), 5.08-5.05 (m, 2H), 4.65-4.62 (m, 2H), 3.94-3.92 (m, 2H), 3.84-3.91 (m, 2H), 3.46-3.45 (m, 2H), 3.31-3.29 (m, 2H), 3.10 (s, 3H). $^{13}$C NMR (100 MHz, DMSO-d$_6$) δ 168.6, 154.3, 145.2, 143.4, 142.1, 142.0, 140.9, 126.5, 126.3, 122.9, 122.8, 122.7, 122.1, 121.4, 120.4, 119.9, 110.6, 110.3, 71.3, 69.9, 68.9, 58.1. HRMS (MALDI-TOF) m/z Calcd for C$_{30}$H$_{30}$FN$_2$O$_3$ 485.2235. Found 485.2211 [M]$^+$.

(E)-1-(2-Ethoxy-2-oxoethyl)-4-(2-(9-(2-(2-methoxyethoxy)ethyl)-9H-carbazol-3-yl)vinyl)quinolin-1-ium bromide (SLAce)

A solution of 8 (0.21 g, 0.5 mmol) and ethyl 2-bromoacetate (0.33 g, 2.0 mmol) in ethanol was stirred overnight at room temperature. After solvent removal, the residue was precipitated from methanol and ethyl acetate to afford SLAce (0.15 g) in 52% yield. $^1$H NMR (400 MHz, DMSO-d$_6$) δ 9.24 (d, J=6.8 Hz, 1H), 9.18 (d, J=8.4 Hz, 1H), 8.89 (s, 1H), 8.61 (d, J=6.8 Hz, 1H), 8.53 (d, J=16 Hz, 1H), 8.42 (d, J=16 Hz, 1H), 8.31 (d, J=8.8 Hz, 1H), 8.26-8.23 (m, 2H), 8.15 (d, J=8.4 Hz, 1H), 8.06 (t, J=7.6 Hz, 1H), 7.80 (d, J=8.4 Hz, 1H), 7.72 (d, J=8.0 Hz, 1H), 7.53 (t, J=8.0 Hz, 1H), 7.33 (t, J=7.2 Hz, 1H), 5.99 (s, 2H), 4.64 (t, J=5.2 Hz, 2H), 4.25 (tr, J=7.2 Hz, 2H), 3.84 (t, J=5.2 Hz, 2H), 3.47 (m, 2H), 3.31 (m, 2H), 3.11 (s, 3H), 1.26 (t, J=5.2 Hz, 3H). $^{13}$C NMR (100 MHz, DMSO-d$_6$) δ 166.5, 154.6, 147.9, 146.5, 142.4, 140.9, 138.7, 128.9, 127.6, 126.7, 126.6, 126.0, 122.8, 122.2, 122.1, 120.4, 119.9, 118.9, 116.2, 115.0, 110.5, 110.4, 71.3, 69.8, 68.8, 62.3, 58.1, 56.4, 42.9, 13.9. HRMS (MALDI-TOF) m/z Calcd for C$_{32}$H$_{33}$N$_2$O$_4$ 509.2446. Found 509.2427 [M]$^+$.

(E)-1-(2-Amino-2-oxoethyl)-4-(2-(9-(2-(2-methoxyethoxy)ethyl)-9H-carbazol-3-yl)vinyl)quinolin-1-ium bromide (SLAD)

A solution of 8 (0.21 g, 0.5 mmol) and 2-bromoacetamide (0.27 g, 2.0 mmol) in acetonitrile was heated to reflux overnight. After removing the solvent, the residue was precipitated from methanol and ethyl acetate to afford SLAD (0.15 g) in 63% yield. $^1$H NMR (400 MHz, DMSO-d$_6$) δ 9.24 (d, J=6.8 Hz, 1H), 9.17 (d, J=8.4 Hz, 1H), 8.89 (s, 1H), 8.58 (d, J=6.8 Hz, 1H), 8.45 (dd, J=33.6 Hz, J=18 Hz, 2H), 8.28-8.25 (m, 2H), 8.18-8.14 (m, 3H), 8.08-8.04 (m, 1H), 7.80 (d, J=8.4 Hz, 2H), 7.72 (d, J=8.4 Hz, 1H), 7.55-7.51 (m, 1H), 7.34-7.31 (m, 1H), 5.68 (s, 2H), 4.66-4.63 (m, 2H), 3.86-3.83 (m, 2H), 3.49-3.47 (m, 2H), 3.31-3.29 (m, 2H), 3.11 (s, 3H). $^{13}$C NMR (100 MHz, DMSO-d$_6$) δ 166.3, 154.0, 148.2, 145.8, 142.3, 140.9, 138.7, 135.2, 128.8, 127.5, 126.7, 126.4, 126.1, 122.8, 122.2, 122.0, 120.4, 118.5, 116.2, 115.0, 110.5, 110.4, 71.3, 69.8, 68.8, 58.1, 57.8, 42.9. HRMS (MALDI-TOF) m/z Calcd for C$_{30}$H$_{30}$N$_3$O$_3$ 480.2281. Found 480.2301 [M]$^+$.

In summary, carbazole-based fluorophores bind to Aβ(1-40) and Aβ(1-42) as well as Aβ aggregates with strong fluorescence enhancement, thus allowing their direct imaging and labeling. TIRFM technique is used to study the effects of these molecules on Aβ aggregation/fibrillation. Some carbazole-based fluorophores, for instance, F-SLOH, and SLAD are non-toxic, potent Aβ aggregation inhibitors and exhibit a protective effect against the neurotoxic activities of the Aβ oligomers and fibrils towards neuronal cells. These properties of F-SLOH, and SLAD together with their ability to cross the blood-brain barrier and target the Aβ plaques, render their application for neuroprotective therapy and as therapeutic agent for Alzheimer's disease.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

The objective of the presently claimed invention is to provide methods for labeling, imaging and detecting the beta-amyloid (Aβ) peptides, oligomers, and fibrils in vitro by using carbazole-based fluorophores. A further aspect of the present invention relates to a method of reducing and preventing aggregation of beta-amyloid peptides for Alzheimer's disease (AD) as well as of treating and/or preventing Alzheimer's disease by using carbazole-based fluorophores.

What is claimed is:

1. A method for treating beta amyloid (Aβ) peptides aggregation-associated diseases and preventing development and progression of said diseases due to increased beta-amyloid aggregates-induced neurotoxicity by administering carbazole-based fluorophores comprising a formula S series:

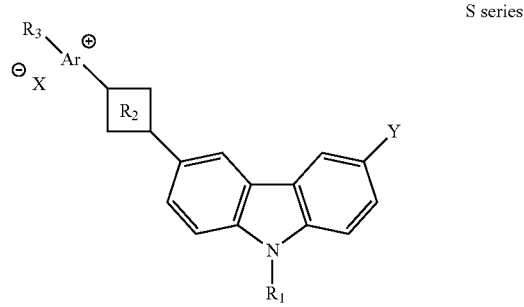

S series said method comprising:
binding said carbazole-based fluorophores to Aβ peptides, oligomers and/or fibrils thereof;
inhibiting the growth and/or aggregation of said Aβ peptides, oligomers and/or fibrils upon said binding; and
protecting neuronal cells against neurotoxic activities of the Aβ oligomers and/or fibrils;
wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;
$R_1$ is a radical selected from the group consisting of polyethylene glycol chain, alkyl, substituted alkyl, peptide chain, glycosidyl, and $C(O)NHCH((CH_2CH_2O)_2CH_3)_2$;
$R_2$ is selected from the group consisting of ethenyl, ethynyl, azo and azomethinyl, $R_3$ is a radical selected from the group consisting of HO-alkyl, alkyl-COOalkyl, alkyl-$CONH_2$, alkyl-CON-Halkyl, polyethylene glycol chain;
X is an anion selected from the group consisting of F, Cl, Br, I, $HSO_4$, $H_2PO_4$, $HCO_3$, tosylate, and mesylate;
Y is selected from the group consisting of H, F, Cl, OH, and $OCH_3$, and wherein when Y is H, $R_3$ cannot be HO-alkyl.

2. The method according to claim 1, wherein Ar is selected from a quinolinyl or substituted quinolinyl; said $R_1$ is a 2-(2-methoxyethoxy)ethoxy; said $R_2$ is an ethenyl; $R_3$ is a 2-hydroxyethyl or acetamide or acetate or 2-(2-methoxyethoxy)ethoxy; said X is a chloride or bromide or iodide and said Y is a H or F which are represented by the formula F-SLOH, SLAD, SLAce, and SLG:

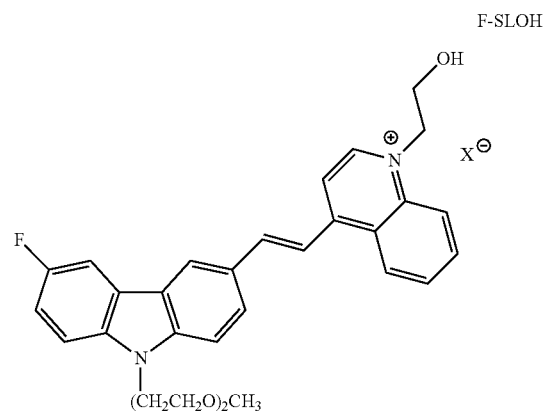

F-SLOH

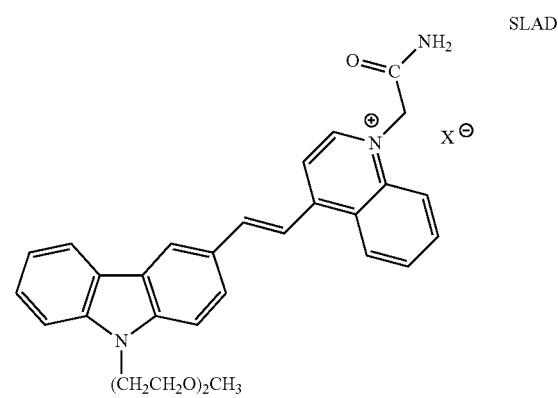

SLAD

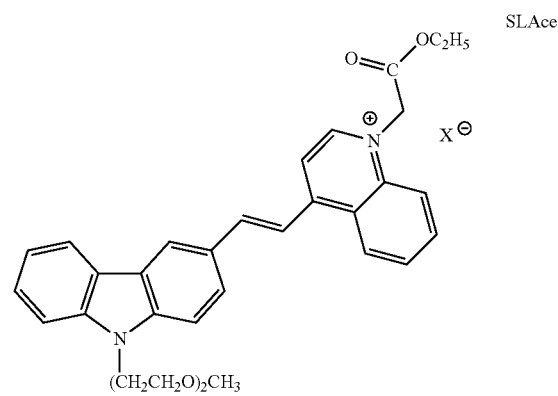

SLAce

-continued

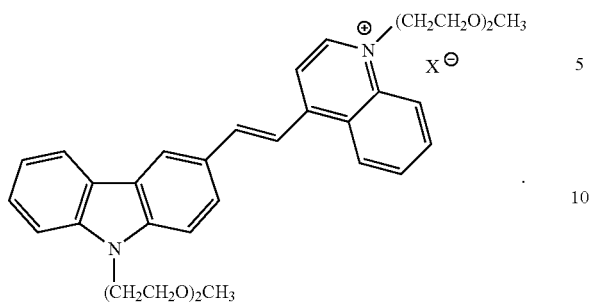

3. The method according to claim 1, wherein the carbazole-based fluorophores are non-toxic.

4. The method according to claim 1, wherein the carbazole-based fluorophores are able to pass through the blood-brain barrier.

5. The method according to claim 1, wherein the carbazole-based fluorophores are introduced to Aβ peptides, oligomers and/or fibrils thereof in vitro.

6. The method according to claim 1, the carbazole-based fluorophores are administered in vivo.

7. The method according to claim 1 wherein said beta-amyloid (Aβ) peptides aggregation-associated diseases is Alzheimer's disease.

* * * * *